US007238668B1

(12) United States Patent
Wayner

(10) Patent No.: US 7,238,668 B1
(45) Date of Patent: Jul. 3, 2007

(54) INHIBITION OF LYMPHOCYTE ADHERENCE WITH CS-1-PEPTIDES AND FRAGMENTS THEREOF

(75) Inventor: Elizabeth A. Wayner, St. Paul, MN (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 0 days.

(21) Appl. No.: 08/452,098

(22) Filed: May 26, 1995

Related U.S. Application Data

(60) Division of application No. 08/338,282, filed on Nov. 14, 1994, now Pat. No. 5,730,978, which is a continuation of application No. 07/814,873, filed on Dec. 24, 1991, now abandoned, which is a continuation-in-part of application No. 07/402,389, filed on Sep. 1, 1989, now abandoned.

(51) Int. Cl.
*A61K 38/00* (2006.01)
*A07K 7/00* (2006.01)

(52) U.S. Cl. .............................. 514/14; 514/2; 514/15; 514/16; 514/17; 514/18; 530/300; 530/327; 530/328; 530/329; 530/330; 530/331

(58) Field of Classification Search ................... 514/2; 530/300, 350, 353, 382
See application file for complete search history.

(56) References Cited

U.S. PATENT DOCUMENTS

| 4,412,990 | A | * | 11/1983 | Lundblad et al. | |
|---|---|---|---|---|---|
| 4,578,079 | A | | 3/1986 | Ruoslahti et al. | 623/11 |
| 4,879,237 | A | | 11/1989 | Rudslahti et al. | 435/240.2 |
| 5,217,870 | A | | 6/1993 | Hession et al. | 435/7.24 |
| 5,229,366 | A | * | 7/1993 | Tsukada et al. | 514/12 |
| 5,340,727 | A | * | 8/1994 | Ruggeri et al. | 435/69.6 |
| 5,403,919 | A | | 4/1995 | Butcher | 530/388.22 |

FOREIGN PATENT DOCUMENTS

| EP | 0 330 506 | 8/1989 |
|---|---|---|
| WO | WO 90/07321 | 7/1990 |
| WO | WO 90/08833 | 8/1990 |
| WO | WO 90/13300 | 11/1990 |
| WO | WO 91/03252 | 3/1991 |

OTHER PUBLICATIONS

Sherman-Gold et al. Genetic Engineering News 13(3) G, I, 14 (1993).*
Hamann et al. J. Immunol. 152: 3282-3293 (1994).*
Algel Da et al. Faseb J. 8: 504-512 (1994).*
Ager et al. Int. Immunol. 2: 921-938 (1990).*
Kogan et al. J Biol Chem. 270:14047-14055 (1995).*
Rozdzinski et al. J. Infect. Diseases 168:1422-1428 (1993).*
Ngo et al. In The Protein Folding Problem and Tertiary Structure Prediction. Merz and Le Grand(eds) Birkhauser Boston 1994, pp. 491-495.*
Kuntz Science 257: 1078-1082 (1992).*
Skolaack et al. Trends in Biotech 18:34-39 (2000).*
Wayner et al., J. Cell Biol. 116:489-497,1992.*
Dustin, M.L., et al., Lymphocyte Function-associated Antigen-1 (LFA-1) Interaction with Intracellular Adhesion Molecule 1 (ICAM1) is One of at Least Three Mechanisms for Lymphocyte Adhesion to Cultured Endothelial Cells, *J. Cell Biol.*, 107, pp. 321-333 (1988).
Harlan, Leukocyte-Endothelial Interactions, *Blood*, 65, pp. 513-525 (1985).
Knapp, Leukocyte Typing IV: White Cell Differentiation Antigens, 1989 Inst. for Immunology, University of Vienna 1087.
Marcantonio, E.E., et al., Antibodies to the Conserved Cytoplasmic Domain of the Integrin β-1 Subunit React With Proteins in Vertebrates, Invertebrates and Fungi, *J. Cell Biol.*, 106, pp. 1765-1772 (1988).
Osbørn, L. et al., Direct Expression Cloning of Vascular Cell Adhesion Molecule 1, a Cytokeine-Induced Endothelial Protein That Binds to Lymphocytes, *Cell*, 59, pp. 1203-1212 (1989).
Ruoslahti, Fibronectin and Its Receptors, *Am. Rev. Biochem.*, 57, pp. 375-413 (1988).
Takada, Y., et al., The Primary Structure of the VLA-2/Collagen Receptor $\alpha^2$ Subunit (Platelet GPIa): Humology to Other Integrins and the Presence of a Possible Collagen-binding Domain, *J. Cell Biol.*, pp. 397-407 (1989).
Lobb, R.R., et al., The Pathophysiologic Role of $\alpha^4$ Integrins In Vivo, *J. Clin. Invest.*, 94, pp. 1722-1728, 1994.
Carlos, T.M., et al., Leukocyte-Endothelial Adhesion Molecules, *Blood*, 84(7):2068-2101, 1994.
Holzmann, B., et al., Identification of a Murine Peyer's Patch-Specific Lymphocyte Homing Receptor as an Integrin Molecule with an α Chain Homologous to Human VLA-4α, *Cell*, 56:37-47, 1989.

(Continued)

*Primary Examiner*—Phillip Gambel
(74) *Attorney, Agent, or Firm*—Townsend and Townsend and Crew LLP

(57) ABSTRACT

The present invention relates to a method for inhibiting the adhesion of one cell to another comprising interfering with the interaction between the extracellular matrix receptor and its ligand.

Figure 1:
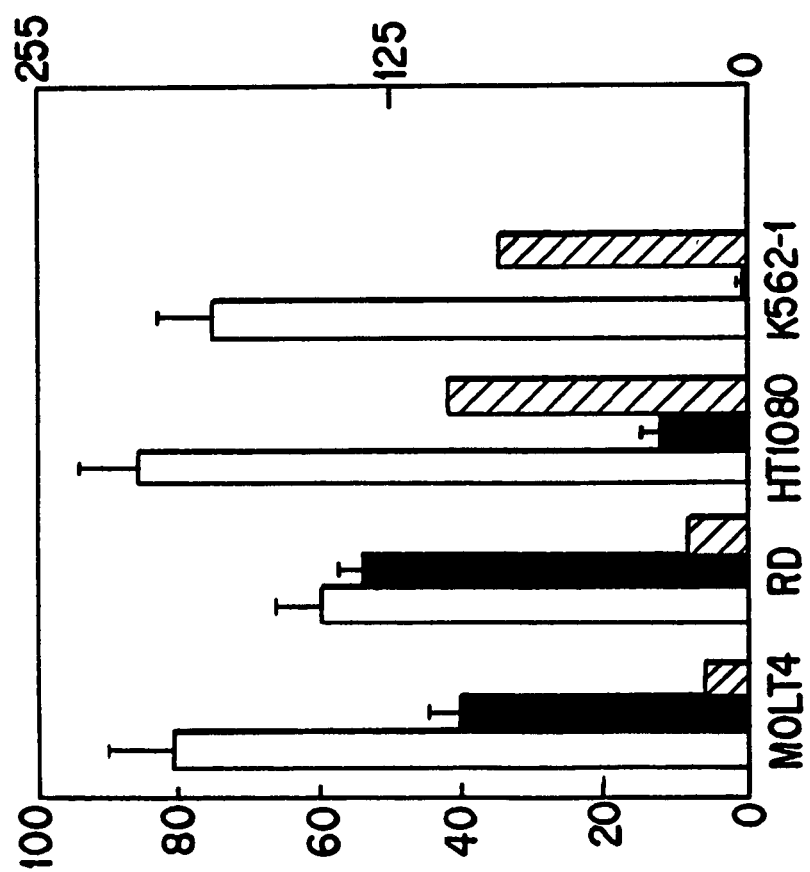

The invention is based upon the discovery that the α4β1 extracellular matrix receptor promotes adhesion of lymphocytes to endothelial cells via attachment to a defined peptide sequence. Prior to the present invention, the ligand of the α4β1 receptor had not been identified, nor had the function of the α4β1 receptor in lymphocyte attachment been known. By preventing the interaction between the α4β1 receptor and its ligands using antibodies or defined peptide sequences, the present invention enables, for the first time, specific intervention in the migration of lymphocytes through the vascular endothelium and into tissues. The present invention, therefore, has particular clinical utility in suppression of the immune response; in various specific embodiments of the invention, the adherence of lymphocytes to endothelium may be inhibited systemically, or may, alternatively, be localized to particular tissues or circumscribed areas. Accordingly, the present invention provides for treatment of diseases involving autoimmune responses as well as other chronic or relapsing activations of the immune system, including allergy, asthma, and chronic inflammatory skin conditions.

16 Claims, 17 Drawing Sheets

OTHER PUBLICATIONS

Liao et al., Exp. Cell Res. 181:348-361, 1989.
Wayner et al., J. Cell Biol. 107:1881-1891, 1988.
Humphries et al., J. Cell Biol. 106:1289-1297, 1988.
Wayner and Carter, J. Cell Biol. 105:1873-1884, 1987.
Hemler et al., J. Biol. Chem 262:11478-11485, 1987.
Bernardi et al., J. Cell Biol. 105:489-498, 1987.
Humphries et al., J. Biol. Chem. 262:6886-6892, 1987.
Haynes, Cell 48:549-554, 1987.
Humphries et al., J. Cell Biol. 103:2637-2647, 1986.
Giancotti et al., J. Cell Biol. 103:429-437, 1986.
Kornblihtt et al., EMBO J. 4:1755-1759, 1985.
Pierschbacher and Ruoslahti, Nature 309:30-33, 1984.
Jalkanen, S., et al., Homing receptors and the control of lymphocyte migration, Immunological Reviews 91:39-60, 1986.
Gallatin, W.M., et al., A cell-surface molecule involved in organ-specific homing of lymphocytes, Nature 304:30-34, 1983.
Gallatin, W.M., et al., Lymphocyte homing receptors, Cell 44:673-680, 1986.
Woodruff, J.J., et al., Specific cell-adhesion mechanisms determining migration pathways of recirculating lymphocytes, Annual Review of Immunology 5:201-222, 1987.
Springer, T.A., et al., The lymphocyte function-associated LFA-1, CD2 and LFA-3, molecules: cell adhesion receptors of the immune system, Annual Review of Immunology 5:223-252, 1987.
Butcher, E.C., et al., Organ specificity of lymphocyte migration: mediation by highly selective lymphocyte interaction with organ-specific determinants on high endothelial venules, Journal of Immunology 10:556-561, 1980.
Jalkanen, S., et al. Biochemical properties of glycoproteins involved in lymphocyte recognition of high endothelial venules in man, Journal of Immunology 141:1615-1623, 1988.
Carter, W.G., and E.A. Wayner, Characterization of the class III collagen receptor, a phosphorylated, transmembrane glycoprotein expressed in nucleated human cells, Journal of Biological Chemistry 263:4193-4201, 1988.
Haskard, D., et al. T lymphocyte adhesion to endothelial cells: mechanisms demonstrated by anti-LFA-1 monoclonal antibodies, Journal of Immunology 137:2901-2906, 1986.
Hamann, A., et al., Evidence for an accessory role of LFA-1 in lymphocyte-high endothelium interaction during homing, Journal of Immunology 140:693-699, 1988.
Kupper, T.S., et al., The integrin-binding peptides GRGDSP and GPEILDVPST abrogate T cell mediated immune responses in vivo, Abstract of poster at FASEB meeting, Apr. 23-25, 1991.
Springer, T.A., Adhesion receptors of the immune system, Nature 346:425-434, Aug. 2, 1990.
Bochner, B.S., et al., "Adhesion of Human Basophils, Eosinophils, and Neutrophils to Interleukin 1-activated Human Vascular Endothelial Cells: Contributions of Endothelial Cell Adhesion Molecules," J. Exp. Med., 173, pp. 1553-1556 (1991).
Burkly, L., et al., "Signaling by Vascular Cell Adhesion Molecule-1 (VCAM-1) Through VLA-4 Promotes CD3-dependent T Cell Proliferation," Eur. J. Immunol., 21, pp. 2871-2875 (1991).
Damle, N., et al., "Vascular Cell Adhesion Molecule 1 Induces T-cell Antigen Receptor-dependent Activation of CD4+ T Lymphocytes," Proc. Natl. Acad. Sci. USA, 88, pp. 6403-6407 (1991).
Dobrina, A., et al., "Mechanisms of Eosinophil Adherence to Cultured Vascular Endothelial Cells," J. Clin. Invest., 88, pp. 20-26 (1991).
Elices, M. J., et al., "VCAM-1 on Activated Endothelium Interacts with the Leukocyte Integrin VLA-4 at a Site Distinct from the VLA-4/Fibronectin Binding Site," Cell, 60, pp. 577-584 (1990).
Freeman, A., et al., "Adhesion of Human B Cells to Germinal Centers in Vitro Involves VLA-4 and INCAM-110," Science, 249, pp. 1030-1033 (1990).
Hemler, M. E., et al., "The VLA Protein Family," J. Biol. Chem., 262(7), pp. 3300-3309 (1987).
Holzmann, B., et al., "Identification of a Murine Peyer's Patch-Specific Lymphocyte Homing Receptor as an Integrin Molecule with an α Chain Homologous to Human VLA-4α," Cell, 56, pp. 37-46 (1989).
Issekutz, T., "Inhibition of In Vivo Lymphocyte Migration to Inflammation and Homing to Lymphoid Tissues by the TA-2 Monoclonal Antibody," J. Immunol., 147, pp. 4178-4184 (1991).

Kilshaw, P., et al., "Expression and Regulation of $β_7(βp)$ Integrins on Mouse Lymphocytes: Relevance to the Mucosal Immune Systems," Eur. J. Immunol., 21, pp. 2591-2597 (1991).
Kohler and Milstein, "Continuous Cultures of Fused Cells Secreting Antibody of Predefined Specificity," Nature, 256, pp. 495-497 (1975).
Lerner, E. A., "How To Make A Hybridoma," Yale J. Biol. Med., 54, pp. 387-402 (1981).
Lobb, R., et al., "Expression and Functional Characterization of a Soluble Form of Vascular Cell Adhesion Molecule 1," Biochem. Biophys. Res. Commun., 178(3), pp. 1498-1504 (1991).
Lobb, R., et al., "Vascular Cell Adhesion Molecule-1," Cellular and Molecular Mechanisms of Inflammation, 2, pp. 151-169 (1991).
Moller, G., "Integrin Molecules Involved in Lymphocyte Homing to Peyer's Patches," Immunological Reviews, 108, pp. 43-61 (1989).
Pulido, R., et al., "Functional Evidence for Three Distinct and Independently Inhibitable Adhesion Activities Mediated by the Human Integrin VLA-4," J. Biol. Chem., 266(16), pp. 10241-10245 (1991).
Rice, G. E., et al., "Vascular and Nonvascular Expression of INCAM-110," Amer. J. Pathology, 138(2), pp. 385-393 (1991).
Sanchez-Madrid, F., et al., "VLA-3: A Novel Polypeptide Association Within the VLA Molecular Complex: Cell Distribution and Biochemical Characterization," Eur. J. Immunol., 16, pp. 1343-1349 (1986).
Taichman, D., et al., "Tumor Cell Surface $α^4β_1$ Integrin Mediates Adhesion to Vascular Endothelium: Demonstration of an Interaction with the N-Terminal Domains of INCAM-110/VCAM-1," Cell Regulation, 2, pp. 347-355 (1991).
van Seventer, G., et al., "Analysis of T Cell Stimulation by Superantigen Plus Major Histocompatibility Complex Class II Molecules or by CD3 Monoclonal Antibody: Costimulation by Purified Adhesion Ligands VCAM-1, ICAM-1, but Not ELAM-1," J. Exp. Medicine, 174, pp. 901-913 (1991).
Walsh, G. M., et al., "Human Eosinophil, But Not Neutrophil, Adherence to IL-1-Stimulated Human Umbilical Vascular Endothelial Cells Is $α_4β_1$ (Very Late Antigen-4) Dependent," J. Immunol., 146, pp. 3419-3423 (1991).
Yuan, Q., et al., "Cloning and Sequence Analysis of a Novel $β_2$-Related Integrin Transcript from T Lymphocytes: Homology of Integrin Cysteine-Rich Repeats to Domain III of Laminin-B Chains," International Immunology, 2(11), pp. 1097-1108 (1990).
Wayner, E.A., et al., Identification and characterization of the T lymphocyte adhesion receptor for an alternative cell attachment domain (CS-1) in plasma fibronectin, The Journal of Cell Biology 109:1321-1330, Sep. 1989.
Guan, J-L., et al., Lymphoid cells recognized an alternatively spliced segment of fibronectin via the integrin receptor $α_4β_1$, Cell 60:53-61, Jan. 12, 1990.
Williams, D.A., et al., Fibronectin and VLA-4 in haematopoietic stem cell-microenvironment interactions, Nature 352:438-441, Aug. 1, 1991.
Mould, A.P., et al., The CS5 peptide is a second site in the IIICS region of fibronectin recognized by the integrin $α_4β_1$, The Journal of Biological Chemistry 266(6):3579-3585, Feb. 25, 1991.
Ferguson, T.A., et al., Two integrin-binding peptides abrogate T cell-mediated immune responses in vivo, Proc. Natl. Acad. Sci. USA 88:8072-8076, Sep. 1991.
Wayner, E.A. and N.L. Kovach, Activation-dependent recognition by hematopoietic cells of the LDV sequence in the V region of fibronectin, The Journal of Cell Biology 116(2):489-497, Jan. 1992.
Takada, Y., et al., The primary structure of the $α^4$ subunit of VLA-4: homology to other integrins and a possible cell-cell adhesion function, The EMBO Journal 8(5):1361-1368, 1989.
Komoriya, A., et al., The minimal essential sequence for a major cell type-specific adhesion site (CS1) within the alternatively spliced type III connecting segment domain of fibronectin is leucine-aspartic acid-valine, The Journal of Biological Chemistry 266(23):15075-15079, Aug. 15, 1991.
Komoriya, A., et al., The minimal essential sequence for a major cell type-specific adhesion site (CS1) within the alternatively spliced IIICS domain of fibronectin is Leu-Asp-Val, 75th Annual Meeting of the Federation of American Societies for Experimental Biology, Atlanta, Georgia, Apr. 21-25, 1991, FASEB Journal 5(6):A1617, Abstract No. 7236, 1991.
Harris et al., TIB Tech 11:42-44 (1993).

Waldmann, *Science* 252:1657-1662 (1991).

Shimizo et al., *Immunological Reviews* 114:109-143 (1990).

Carlos et al., *Immunological Reviews* 114:5-25 (1990).

Wayner, E.A., et al., "Identification and characterization of the T lymphocyte adhesion receptor for an alternative cell attachment domain (CS-1) in plasma fibronectin," *The Journal of Cell Biology* 109:1321-1330, Sep. 1989. [Same as B24].

Carter et al., *J. Cell Biology* 110:1387-1404 (1990).

Stoolman, *Cell* 56:907-910 (1989).

Hemler, *Immunol. Today* 9:109-113 (1988).

Pitzalis et al., *Eur. J. Immunol.* 8:1292 (1988).

Thorpe, "Monoclonal Antibodies: Clinical and Regulatory Issues", *Trends in Biotechnology*, 11, pp. 40-42 (1993).

Dufour et al., "Attachment, Spreading and Locomotion of Avian Neural Crest Cells are Mediated by Multiple Adhesion Sites on Fibronectin Molecules", *EMBO J.*, vol. 7, pp. 2661-2671 (1988).

Yednock, T.A., et al., "Prevention of Experimental Autoimmune Encephalomyelitis by Antibodies Against $\alpha 4\beta 1$ Integrin," *Nature*, 356, pp. 63-66 (1992).

Ebers, G.C., Treatment of multiple sclerosis, *Lancet*, 343:275-279, 1994.

Brennan, F.M., Role of cytokines in experimental arthritis, *Clin. Exp. Immunol.*, 97:1-3, 1994.

Kahan, B.D., Immunosuppressive therapy, *Current Opinion in Immunology*, 4:553-560, 1992.

Jolliffe, L.K. Humanized Antibodies: Enhancing therapeutic utility through engineering, *Intern. Rev. Immunol.*, 10:241-250, 1993.

Edgington, S.M., How sweet it is: Selectin-mediating drugs, *Bio/Technology*, 10:383-389, 1992.

Shaffer, M., Drugs giants, start-ups target adhesion molecules key to inflammatory disease, *Biotechnology Newswatch*, 10:9, 1993.

Ward, P.A., et al., Blocking of adhesion molecules in vivo as anti-inflammatory therapy, Therapeutic Immunology 1:165-171, 1994.

Mountain, A., et al., Engineering antibodies for therapy, Biotechnology & Genetic Engineering Reviews 10(1):10-13, 1992.

Takada, Y., et al., Fibronectin receptor structures in the VLA family of heterodimers, Nature 362:607-609, 1987.

Holzmann, B., et al., Integrin molecules involved in lymphocyte homing to Peyer's patches, Immunological Reviews 108:45-61, 1989.

Stamper, H.B., Jr. et al., Lymphocyte homing into lymph nodes: in vitro demonstration of the selective affinity of recirculating lymphocytes for high-endothelial venules, The Journal of Experimental Medicine 144:828-833, 1976.

Erickson, H.P., et al., Fibronectin molecule visualized in electron microscopy: a long, thin flexible strand, The Journal of Cell Biology 91:673-678, 1981.

Berlin, C., et al., $\alpha 4\beta 7$ integrin mediates lymphocyte binding to the mucosal vascular addressin MAdCAM-1, Cell 74:185-195, 1993.

Abraham et al., *Am. J. Respir. Crit. Care Med.* A Small-Molecule, Tight-Binding Inhibitor of the Integrin $\alpha 4\beta 1$ Blocks Antigen-Induced Airway Responses and Inflammation in Experimental Asthma in Sheep 162: 603-611 (2000).

Viles et al., *Eur. J. Biochem.* Multiple Solution Conformations of the Integrin-Binding Cyclic Pentapeptide Cyclo-(-Ser-D-Leu-Asp-Val-Pro-) Analysis of the Space Available to Cyclic Pentapeptides 242:352-362 (1996).

Kanehiro et al., *Timing of Administration of Anti-VLA-4 Differentiates Airway Hyperresponsiveness in the Central and Peripheral Airways in Mice* 162:1132-1139 (2000).

Brown D., et al., "Synthesis and expression of the fibroblast fibronectin receptor in human monocytes," *J. Clin. Invest.*, 84(1):366-370 (Jul. 1989).

Chan P. and Aruffo A., "VLA-4 integrin mediates lymphocyte migration on the inducible endothelial cell ligand VCAM-1 and the extracellular matrix ligand fibronectin," *J. Biol. Chem.*, 268(33):24655-24664 (Nov. 25, 1993).

Duijvestijn A., et al., "High endothelial differentiation in human lymphoid and inflammatory tissues defined by monoclonal antibody HECA-452," *Am. J. Pathol.*, 130(1):147-155 (Jan. 1988).

Enders G., et al., "Role of Peyer's patch in the intestinal immune response to cholera toxin in enterically immunized rats," *Infect. Immun.*, 55(9):1997-1999 (Sep. 1987).

Freemont A., et al., "Changes in vascular endothelium related to lymphocyte collections in diseased synovia," *Arthritis Rheum.*, 26(12): 1427-1433 (Dec. 1983).

Garcia-Bernal D., et al., "Vav1 and Rac control chemokine-promoted T lymphocyte adhesion mediated by the integrin $\alpha 4\beta 1$," *Mol. Biol. Cell*, 16(7):3223-35 (Jul. 2005).

Gowans J. and Knight E., "The route of re-circulation of lymphocytes in the rat," *Proc. R. Soc. Lond. B. Biol. Sci.*, 159:257-82 (Jan. 14, 1964).

Hemler M., et al., "Characterization of the cell surface heterodimer VLA-4 and related peptides," *J. Biol. Chem.*, 262(24):11478-11485 (Aug. 25, 1987).

Hemler M., et al., "Adhesive protein receptors on hematopoietic cells," *Immunol. Today*, 9(4):109-13 (Apr. 1988).

Holzmann B., et al., "Peyer's patch-specific lymphocyte homing receptors consist of a VLA-4-like $\alpha$ chain associated with either of two integrin $\beta$ chains, one of which is novel," *EMBO J.*, 8(6):1735-1741 (Jun. 1989).

Idzerda R., et al., "Isolation and DNA sequence of a cDNA clone encoding a lymphocyte adhesion receptor for high endothelium," *Proc. Natl. Acad. Sci. USA*, 86(12):4659-4663 (Jun. 1989).

Jalkanen S., et al., "Human lymphocyte and lymphoma homing receptors," *Annu. Rev. Med.*, 38:467-476 (1987).

Jalkanen S., et al., "A distinct endothelial cell recognition system that controls lymphocyte traffic into inflamed synovium," *Science*, 233(4763):556-8 (Aug. 1, 1986).

Johnston B., et al., "$\alpha_4$ Integrin-Dependent Leukocyte Recruitment Does Not Require VCAM-1 in a Chronic Model of Inflammation," *J. Immunol.*, 164(6):3337-3344 (Mar. 15, 2000).

Kamata T., et al., "Identification of putative ligand-binding sites of the integrin alpha 4 beta 1 (VLA-4 CD49d/CD29)," *Biochem. J.*, 305:945-951 (Feb. 1, 1995).

Kovach N., et al., "A monoclonal antibody to $\beta_1$ integrin (CD29) stimulates VLA-dependant adherence of leukocytes to human umbilical vein endothelial cells and matrix components," *J. Cell Biol.*, 116(2):499-509 (Jan. 1992).

Lockhart-Mummery H. and Morson B., "Crohn's disease (regional enteritis) of the large intestine and its distinction from ulcerative colitis," *Gut*, 1:87-105 (Jun. 1960).

Marchesi V. and Gowans J., "The migration of lymphocytes through the endothelium of venules in lymph nodes: an electron microscope study," *Proc. R. Soc. Lond. B. Biol. Sci.*, 159:283-90 (Jan. 14, 1964).

Palecanda A., et al., "Rat mast cell lines bind to the vascular cell ahesion molecule-1 (VCAM-1) and the mucosal addressin cell adhesion molecule-1 (MAdCAM-1)," *J. Immunol.*, 158(6):2904-2910 (Mar. 15, 1997).

Pals S., et al., "Mechanisms of human lymphocyte migration and their role in the pathogenesis of disease," *Immunol. Rev.*, 108:111-133 (Apr. 1989).

Stamper H. and Woodruff J., "Lymphocyte homing into lymph nodes: in vitro demonstration of the selective affinity of recirculating lymphocytes for high-endothelial venules," *J. Exp. Med.*, 144(3):828-33 (Sep. 1, 1976).

Stevens S., et al., "Differences in the migration of B and T lymphocytes: organ-selective localization in vivo and the role of lymphocyte-endothelial cell recognition," *J. Immunol.*, 128(2):844-851 (Feb. 1982).

Takada Y. and Puzon W., "Identification of a regulatory region of integrin $\beta_1$ subunit using activating and inhibiting antibodies," *J. Biol. Chem.*, 268(23):17597-17601 (Aug. 15, 1993).

Weissman, I., et al., U.S. Appl. No. 07/289,201, filed Dec. 23, 1988, for "Homing Sequences and Their Uses".

Weissman, I., et al., U.S. Appl. No. 07/315,736, filed Feb. 24, 1989, for "Homing Sequences and Their Uses".

Wu N., et al., "Evolutionary conservation of tissue-specific lymphocyte-endothelial cell recognition mechanisms involved in lymphocyte homing," *J. Cell Biol.*, 107(5):1845-1851 (Nov. 1988).

\* cited by examiner

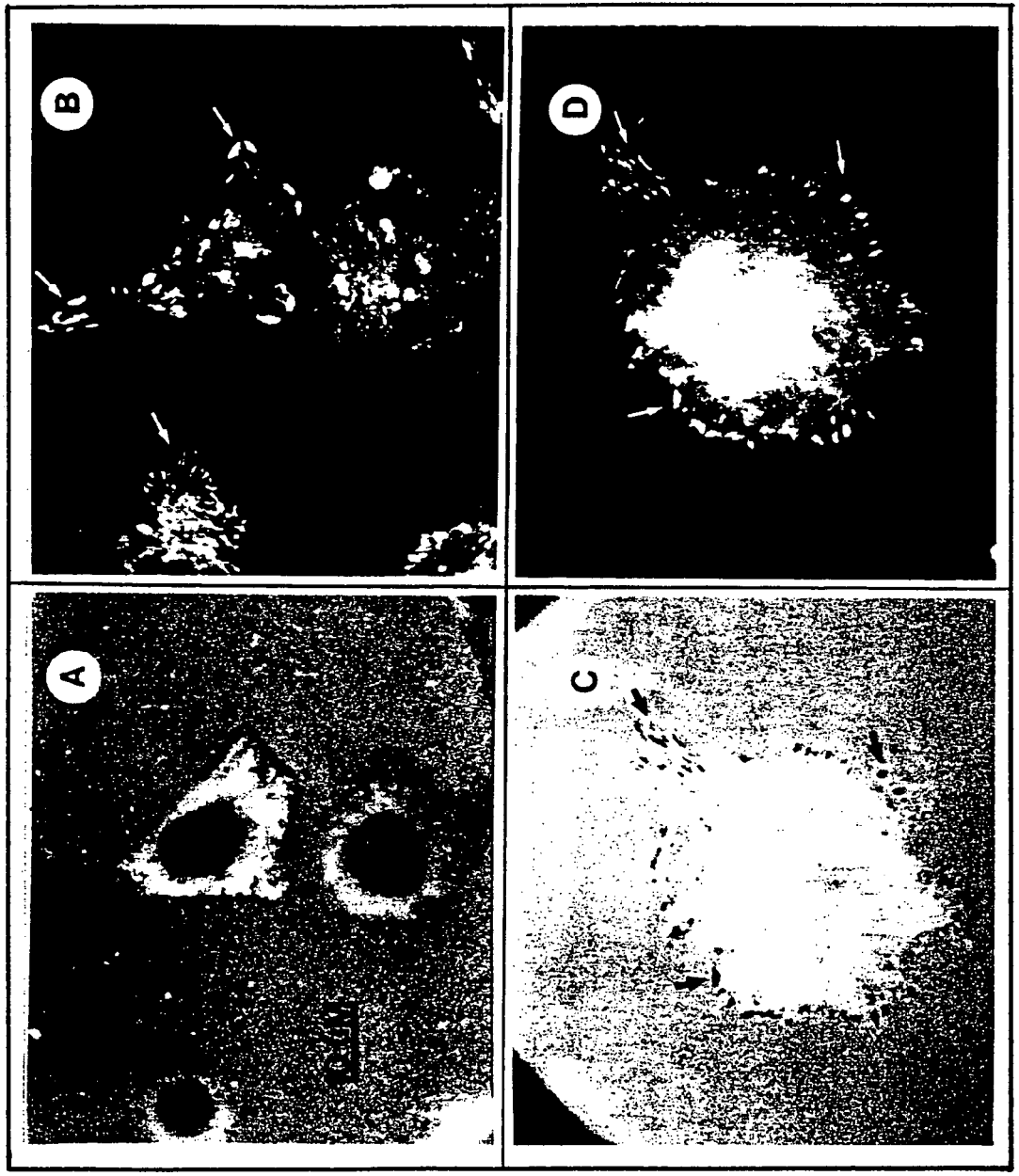

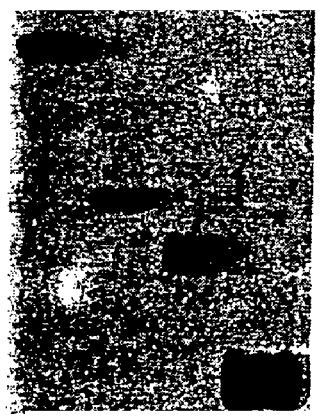
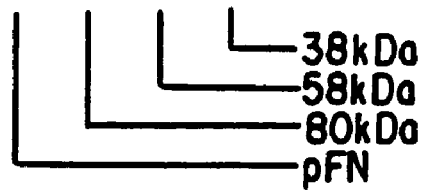

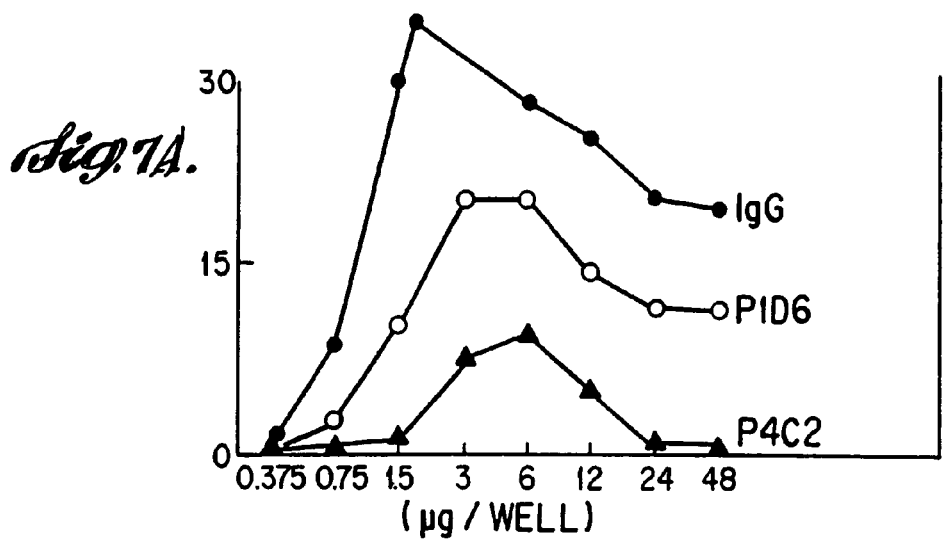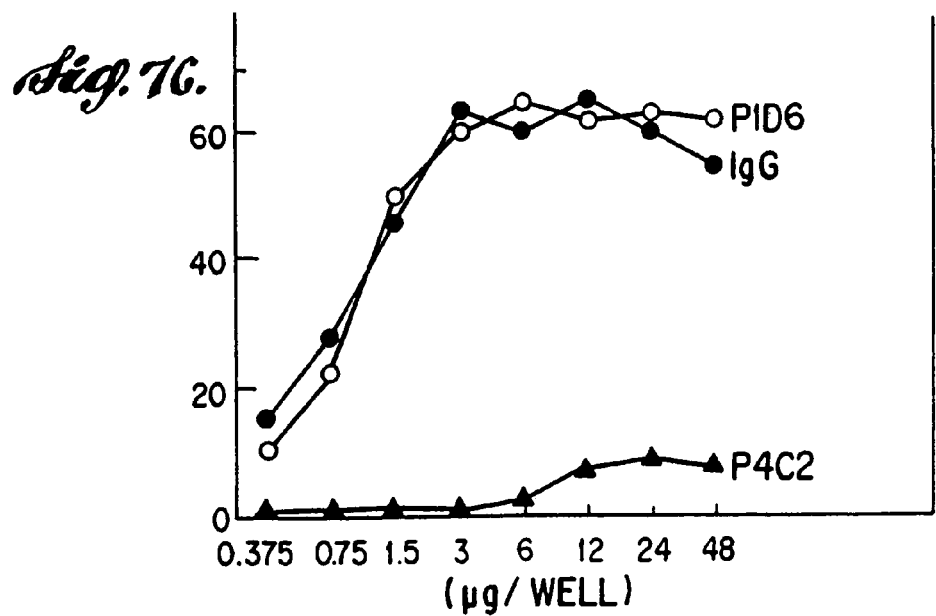

INHIBITION OF LYMPHOCYTE ADHERENCE WITH CS-1-PEPTIDES AND FRAGMENTS THEREOF

This is a divisional of Ser. No. 08/338,282, filed Nov. 14, 1994, now U.S. Pat. No. 5,730,978, which is a continuation of Ser. No. 07/814,873, filed Dec. 24, 1991 (abandoned), which is a continuation-n-part of Ser. No. 07/402,389, filed Sep. 1, 1989 (abandoned).

This invention was made with government support under grant RO1 CA49259 awarded by the National Institutes of Health. The government has certain rights in the invention.

1. INTRODUCTION

The present invention relates to a method for inhibiting the adhesion of one cell to another. It is based on the discovery that the $\alpha 4\beta 1$ extracellular matrix receptor promotes adhesion of lymphocytes to endothelial cells via attachment to a defined peptide sequence. In particular embodiments of the invention, monoclonal antibodies or peptides may be used to inhibit binding of lymphocytes to endothelial cells, thereby preventing lymphocyte entrance into tissue and suppressing the immune response.

2. BACKGROUND OF THE INVENTION

2.1. Extracellular Matrix Receptors

Specific cell surface receptors (R) for extracellular matrix (ECM) components such as collagen, fibronectin and laminin have been described (reviewed by Hynes, 1987, Cell, 48:549–554; Hemler, 1988, Immunol. Today, 9:109). The functions of the extracellular matrix receptors (ECMRs I, II and VI) have been defined by affinity chromatography (Wayner and Carter, 1987, J. Cell Biol., 105:1873–1884; Staatz et al., 1989, J. Cell Biol., 198:1917–1924) and by preparing monoclonal antibodies that specifically inhibited the interaction of cells with purified ligands (Wayner and Carter, 1987, J. Cell Biol. 105:1873–1884) or ECM (Wayner et al., 1988, J. Cell Biol. 107:1881–1891).

A variety of ECMRs have been identified using these techniques. Using monoclonal antibodies, Wayner and Carter (1987, J. Cell Biol. 105:1873–1884) identified two classes of cell surface receptors for native collagen in human fibrosarcoma cells; class I was involved in cell adhesion to collagen, fibronectin and laminin, whereas class II was involved in cell adhesion only to native collagen. Wayner et al. (1988, J. Cell Biol. 107:1881–1891) identified monoclonal antibodies that inhibit human cell adhesion to collagen (P1H5), fibronectin (P1F8 or P1D6) and both collagen and fibronectin (P1B5); P1F8 and P1D6 were found to react with a 140 kD surface receptor known as ECMR VI. Kunicki et al. (1988, J. Biol. Chem. 263:4516–4519) reported that P1H5 (supra) also specifically inhibited adhesion of unactivated human platelets to collagen types I and III, but not to fibronectin. A complex comprising at least three glycoproteins was isolated from chicken embryo fibroblasts, using monoclonal antibodies which block cell adhesion to fibronectin (Knudsen et al., 1985, Exp. Cell Res. 157: 218–226; Chen et al., 1985, J. Cell Biol. 100:1103–1114) whereas a complex of two glycoproteins was isolated from mammalian cells using vitronectin affinity chromatography (Pytela et al., 1985, Proc. Natl. Acad. Sci. U.S.A. 82:5766–5770; Pytela et al., 1986, Science 231:1559–1562). Major platelet surface glycoproteins IIb and IIIa have been found to exist as a noncovalent 1:1 complex in the platelet membrane (Jennings and Phillips, 1982, J. Biol. Chem. 257:10458–10463) and to serve as an ECMR for fibrinogen (Bennett et al., 1983, Proc. Natl. Acad. Sci. U.S.A. 80:2417–2421; Marguerie et al., 1984, Eur. J. Biochem. 139:5–11), fibronectin (Gardner and Hynes, 1985, Cell 42:439–448; Plow et al., 1985, Blood 66:724–727), von Willebrand factor (Ruggeri et al., 1982, Proc. Natl. Acad. Sci. U.S.A. 79:6038–6041) and vitronectin (Pytela et al., 1986, Science 231:1559–1562).

Structural homology is shared by the multitude of extracellular matrix receptors. The ECMRs are members of the integrin family of cell adhesion molecules and possess unique $\alpha$ subunits complexed to the integrin $\beta 1$ subunit (Hynes, 1987, Cell 48:549–554; Wayner and Carter, 1987, J. Cell Biol. 105:1873–1884; Wayner et al., 1988, J. Cell Biol., 107:1881–1891). Additional members of the integrin receptor family include leukocyte adhesion proteins and the VLA antigens. The leukocyte adhesion proteins include LFA-1, Mac-1, and P150/95, and are dimeric glycoproteins composed of different $\alpha$ chains and a common, 95 kDa $\beta$ chain, (Kishiomoto et al., 1987, Cell 48:681–690). VLA antigens are named for their very late appearance on cultured T lymphocytes (Hemler et al., 1983, J. Immunol. 131:334–340; Hemler et al., 1984, J. Immunol. 132:3011–3018; Hemler et al., 1985, Eur. J. Immunol. 15:502–50°). Antisera to the VLA-$\beta$ subunit were found to block cell adhesion to fibronectin or laminin (Takada et al., 1987, Nature 326:607–610).

Interrelationships between these ECMRs have been identified. ECMR VI is identical to the prototype fibronectin receptor (Pytela et al., 1985, Cell, 40:191–198), $\alpha 5\beta 1$, platelet glycoprotein (gp) Ic/IIa and VLA 5, ECMR II is identical to $\alpha 2\beta 1$, platelet glycoprotein Ia/IIa and VLA 2 (Hemler et al., 1987, J. Biol. Chem., 262:11478–11485), and ECMR I is identical to $\alpha 3\beta 1$ and VLA 3 (Kunicki et al., 1988, J. Biol. Chem., 263:4516–4519; Takada et al., 1988, J. Cellular Biochem., 37:385–393; Wayner et al., 1988, J. Cell Biol. 107:1881–1891). Monoclonal antibodies to $\alpha 2\beta 1$, $\alpha 3\beta 1$ and $\alpha 5\beta 1$ (P1H5, P1D6 and P1B5) inhibit fibroblast or platelet adhesion to collagen, fibronectin and laminin-coated surfaces (Kunicki et al., 1988, J. Cell Biol. 107:1881–1891; Wayner et al., 1988, supra). Table I lists some of the members of the integrin family described supra, and Table II lists a number of monoclonal antibodies that recognize various ECMRs.

TABLE I

THE INTEGRIN RECEPTOR FAMILY

| Receptor | Subunit Composition | Known Ligands | Known Functions |
|---|---|---|---|
| Chicken Integrin Complex | $\alpha_0\beta_1$ $\alpha_3\beta_1$ | FN, LM, VN | Cell adhesion, Cell migration, Cytoskeletal connection |
| Fibronectin receptor | $\alpha_5\beta_1$ | FN | Adhesion to Fibronectin |
| Vitronectin receptor | $\alpha_5\beta_1$ | VN | Adhesion to Vitronectin |
| Glycoprotein IIb/IIIa | $\alpha_{II}\beta_3$ | FN, FB, VN, VWF | Platelet adhesion and aggregation |
| LFA-1 | $\alpha_1\beta_2$ | ICAM-1, ICAM-2 | Leukocyte adhesion to Endothelium |
| MAC-1 | $\alpha_m\beta_2$ | C3bi | C3b receptor monocyte and leukocyte adhesion |
| p150/95 | $\alpha_{1-6}\beta_1$ | C3bi | Neutrophil adhesion |

TABLE I-continued

THE INTEGRIN RECEPTOR FAMILY

| Receptor | Subunit Composition | Known Ligands | Known Functions |
|---|---|---|---|
| VLAs 1–6 | $\alpha_{1-6}\beta_1$ | FN, COL, LAM | Cell adhesion, migration and Cytoskeletal connection |
| Epithelial | $\alpha_6\beta_4$ | LAM | Epithelial adhesion |
| Epithelial | $\alpha_v\beta_5$ | VN, FN | Epithelial Cell adhesion to VN, FN |
| ECMRs I, II, VI, V | $\alpha_2\beta_1$ | COL, LAM | Adhesion to COL, LM |
| | $\alpha_3\beta_1$ | COL, LM, FN | Adhesion to COL, LM, FN |
| | $\alpha_4\beta_1$ | FN | |
| | $\alpha_5\beta_1$ | | Previously unknown Adhesion to FN |

TABLE II

ANTI-ECMR ANTIBODIES

| Antibody | Receptor | Ligand | Reference |
|---|---|---|---|
| P1H5 | $\alpha_2\beta_1$ | Collagen Laminin | (Wayner et al., 1987, J. Cell Biol. 105:1873–1884; Wayner et al., 1988, J. Cell Biol. 107:1881–1891) |
| P1B5 | $\alpha_3\beta_1$ | Collagen Fibronectin | (Wayner et al., 1987 J. Cell Biol. 105:1873–1884) |
| P4C2 | $\alpha_4\beta_1$ | Fibronectin (CS-1) | |
| P1D6 | $\alpha_5\beta_1$ | Fibronectin (Arg-Gly-Asp-Ser) | (Wayner et al., 1988, J. Biol. 105:1873–1884) |
| Cell | | | |
| P4C10 | $\beta_1$ | FN, COL, LAM | |
| P4119 | $\beta_2$(CD18) | | |

The β1 integrins are differentially expressed in cultured cells and tissue, and demonstrate clear differences in activation dependent expression. For example, expression of α5β1 in hematopoietic cells is restricted to subpopulations of thymocytes and peripheral blood lymphocytes, monocytes, acute lymphocytic or myelogenous leukemias, activated T cells, migrating hemopoietic precursor cells, and some cultured T, B or erythroleukemia cell lines (Bernardi et al., 1987, J. Cell Biol., 105:489–498; Cardarelli et al., 1988, J. Cell Biol., 106:2183–2190; Garcia-Pardo et al., 1989 Garcia-Pardo et al., 1989, Exp. Cell Res., 181:420–431; Giancotti et al., 1986, J. Cell. Biol., 103:429–437; Liao et al., 1987, Exp. Cell Res., 171:306–320; Wayner et al., 1988, J. Cell Biol. 107:1881–1891.

2.2. Fibronectin

Fibronectin is a protein found in the extracellular matrix as well as in plasma and on the surface of certain types of cells (Akiyama and Yamada, 1987, Adv. Enzymol. 59:1–57). In plasma, fibronectin exists as a glycoprotein heterodimer consisting of two similar subunits (called A and B chains), each having a molecular weight of approximately 220 kDa (Aidyama and Yamada, 1987, Adv. Enzymol. 59:1–57; Erickson et al., 1981, J. Cell Biol. 91:673–678). Multiple specialized intramolecular domains (Ruoslahti et al., 1981, J. Biol. Chem. 256:7277–7281) of the fibronectin molecule may be cleaved into fragments which, in turn, are capable of interacting with collagen, fibrin, heparin, and cell surfaces in a manner analogous to that of the intact molecule (Hynes and Yamada, 1982, J. Cell Biol. 95:369–377).

Cellular and plasma fibronectin heterodimers comprise similar but not identical polypeptides. The variability in the structure of fibronectin subunits derives from variations in fibronectin mRNA primary sequence due to alternative splicing in at least 2 regions of the pre-fibronectin mRNA (the ED and IIICS regions).

Fibronectin is capable of promoting adhesion of a variety of cell types, such as fibroblasts (Grinell et al., 1977, Exp. Cell Res. 110:175–210), macrophages (Bevilacque et al., 1981, J. Exp. Med. 153:42–60), polymorphonuclear leukocytes (Marino et al., 1985, J. Lab. Clin. Med. 105:725–730), platelets (Koteliansky et al., 1981, Fed. Euro. Biochem. Soc. 123:59–62) and keratinocytes (Clark et al., 1985, J. Invest. Dermatol. 84:378–383), to name but a few (Liao et al., 1989, Exp. Cell Res. 181:348–361). Interaction between fibronectin and a cell surface protein having a molecular weight of approximately 140 kDa has been observed in fibroblasts (Brown and Juliano, 1985, Science 228:1448–1451; Aidyama et al., 1986, J. Cell Biol. 102:442–448; Brown and Juliano, 1986, J. Cell Biol. 103:1595–1603; Wylie et al., 1979, J. Cell Biol. 80:385–402), endothelial cells (Plow et al., 1986, Proc. Natl. Acad. Sci. U.S.A. 83:6002–6006), lymphoid cells (Brown and Juliano, 1986, J. Cell Biol. 103:1595–1603; platelets (Pytela et al., 1986, Science 228: 1559–1562; Gardner and Hynes, 1985, Cell 42:439–448), muscle cells (Horowitz et al., 1985, J. Cell Biol. 101: 2134–2144; Dambsky et al., 1985, J. Cell Biol. 100: 1528–1539; Chapman, 1984, J. Cell Biochem. 259:109–121), and osteosarcoma cells (Pytela et al., 1985, Cell 40:191–198).

The binding of fibronectin to cell surfaces may be competitively inhibited by fragments of fibronectin (Akiyama et al., 1985, J. Biol. Chem. 260:13256–13260). Using synthetic peptides, a sequence of what was thought to be the only minimal cell-recognition site was identified as the tetrapeptide Arg-Gly-Asp-Ser (RGDS) (SEQ ID NO: 1) Pierschbacher and Ruoslahti, 1984, Nature 309:30–33; Pierschbacher et al., 1982, Proc. Natl. Acad. Sci. U.S.A. 80:1224–1227; Pierschbacher et al., 1984, Proc. Natl. Acad. Sci. U.S.A. 81:5985–5988; Akiyama et al., 1985, J. Cell Biol. 102:442–448). The RGDS sequence present in the "cell binding" domain of fibronectin is the ligand for the prototype of fibronectin receptor described by Pytela et al. (1985, Cell 40:191–198).

Various observations suggested that regions other than RGDS may function in fibronectin binding (Humphries et al., 1986, J. Cell Biol. 103:2637–2647). For example, the binding affinity of synthetic peptides was found to be substantially lower than the binding affinity associated with larger fragments or intact fibronectin (Akiyama et al., 1985, J. Biol. Chem. 260:10402–10405; Akiyama et al., 1985, J. Biol. Chem. 260:13256–13260). McCarthy et al. (1986, J. Cell Biol. 102:179–188) reported binding affinity between a 33 kDa fragment of plasma fibronectin and B16-F10 melanoma tumor cells. Bernardi et al. (1987, J. Cell Biol. 105:489–498) reported that lymphoid precursor cells adhered to two different sites on fibronectin; the BaF3 cell line interacted with the RGD binding domain, whereas the PD31 cell line appeared to interact with a different domain located in the carboxy terminal segment and associated with a high affinity binding site for heparin.

Humphries et al. (1986, J. Cell Biol. 103:2637–2647) compared the ability of fibronectin fragments to form adhesive interactions with melanoma versus fibroblastic cells. Fibroblastic BHK cells were observed to spread rapidly on a 75 kDa fragment representing the RGDS containing cell-binding domain, whereas B16-F10 melanoma cells did not appear to spread on the 75 kDa fragment, but, instead were observed to spread on a 113 kDa fragment derived from the portion of fibronectin containing the type III connecting segment (CS) difference region, or V-region (in which alternative splicing of mRNA may occur). In this IIICS region, located near the fibronectin carboxyl terminus, the sequence Arg-Glu-Asp-Val (REDV) (SEQ ID NO: 2) appeared to have functional significance. Humphries et al. (1987, J. Biol. Chem. 262:6886–6892) of overlapping synthetic peptides spanning the IIICS region. Two nonadjacent peptides, CS1 and CS5, were found to be competitively inhibitory for adhesion of fibronectin to melanoma, but not to fibroblastic, cells, with CS1 showing greater inhibitory activity than CS5. Liao et al. (1989, Exp. Cell Res. 181: 348–361), reported that MOPC 315, IgA-secreting lymphoid cells, in addition to binding to the cell binding domain via an RGD interaction, bound preferentially to the carboxy-terminal heparin binding domain by an RGD-independent mechanism. However, the adhesion sequence(s) present in the carboxy terminal regions of fibronectin and the cell surface receptor(s) responsible for adhesion of cells to these adhesion sequences have not been identified.

2.3. Biological Functions of Cell Adhesion Molecules

Adhesive interactions between cells have been found to occur during many important biological events, including tissue differentiation, growth and development, and also appear to play a critical role in the pathogenesis of various diseases (Humphries et al., 1986, J. Cell Biol. 103:2637–2647; Grinnell, 1984, J. Cell Biochem. 26:107–116; Hynes, 1986, Sci. Am. 254:42–51).

For example, adhesive interactions are known to be extremely important in the immune system; in which the localization of immune mediator cells is likely to be due, at least in part, to adhesive interactions between cells. Recirculation of lymphoid cells is non-random (Male et al., in "Advanced Immunology", J. B. Lippincatt Co., Philadelphia, p. 14.4–14.5); lymphocytes demonstrate a preference for the type of secondary lymphoid organ that they will enter. In trafficing through a secondary lymphoid organ, lymphocytes must first bind to the vascular endothelium in the appropriate post-capillary venules, then open up the tight junctions between endothelial cells, and finally migrate into the underlying tissue. Migration of recirculating lymphocytes from blood into specific lymphoid tissues, called homing, has been associated with complementary adhesion molecules on the surface of the lymphocytes and on the endothelial cells of the high endothelial venules.

Likewise, the adherence of polymorphonuclear leukocytes to vascular endothelium is believed to be a key event in the development of an acute inflammatory response, and appears to be required for an effective chemotactic response as well as certain types of neutrophil-mediated vascular injury (Zimmerman and McIntyre, 1988, J. Clin. Invest. 81:531–537; Harlan et al., 1987, in "Leukocyte Emigration and its Sequelae", Movat, ed. S. Karger A G, Basel, pp. 94–104; Zimmerman et al., ibid., pp. 105–118). When stimulated by specific agonist substances, the polymorphonuclear leukocytes Tonnensen et al., 1984, J. Clin. Invest. 74:1581–1592), endothelial cells (Zimmerman et al., 1985, J. Clin. Invest. 76:2235–2246; Bevilacque et al., J. Clin. Invest. 76:2003–2011), or both (Gamble et al., 1985, Proc. Natl. Acad. Sci. U.S.A. 82:8667–8671) become adhesive; as a result, polymorphonuclear leukocytes accumulate on the endothelial cell surface.

In addition, studies with specific anti-glycoprotein antibodies in patients with immune deficits indicated that one or more components of the CD18 complex are required for effective neutrophil chemotaxis and other adhesion-related functions (Zimmerman and MacIntyre, 1988, J. Clin. Invest. 81:531–537). The CD18 complex is identical to the $\beta_2$ integrin subfamily (supra).

During maturation and differentiation, lymphocyte subpopulations localize in different anatomical sites; for example, immature T cells localize in the thymus. Similarly, IgA-producing B cells are observed to localize in the intestinal mucosa (Parrott, 1976, Clin. Gastroenterol. 5:211–228). In contrast, IgG-producing B cells localize primarily in lymph nodes, from which IgG is secreted into the systemic circulation (Parrott and deSousa, 1966, Nature 212:1316–1317). T cells appear to be more abundant in skin epidermis than in mucosal linings (Cahill et al., 1977, J. Exp. Med. 145:420–428).

The physiologic importance of leukocyte adhesion proteins (supra) is underscored by the existence of a human genetic disease, leukocyte adhesion deficiency (LAD; Anderson et al., 1985, J. Infect. Dis. 152:668; Arnaout et al., 1985, Fed. Proc. 44:2664). Various studies have indicated that the molecular defect associated with LAD results in either lack of synthesis of the common β chain or normal rate of synthesis followed by rapid degradation (Liowska-Grospierre et al., 1986, Eur. J. Immunol. 16:205; Diamanche et al., 1987, Eur. J. Immunol. 17:417). In the severe form of LAD, neither LFA-1, Mac-1, nor p150/95 are expressed on the leukocyte membrane; low levels of leukocyte membrane expression have been observed in patients suffering from the moderate form of the disease. This leads to a defective mobilization of polymorphonuclear leukocytes and monocytes from the vasculature to the issues during the inflammatory response, with consequent recurrant bacterial infections (Anderson et al., J. Infect. Dis. 152:668; Arnaout et al., 1985, Fed. Proc. 44:2664).

ECMRs have also been observed to be associated with functions outside of the immune system. Loss of the IIb/IIIa platelet surface glycoprotein complex appears to result in defective platelet function in a genetic disease known as Glanzmann's thrombasthenia, (Hynes, 1987, Cell 48:549–554). Humphries et al. (1988, J. Cell Biol. 106: 1289–1297) observed that neurons of the peripheral nervous system were able to extend neurites onto substrates bearing both the central cell-binding domain and the IIICS region of fibronectin. Furthermore, we have recently shown that neurite formation on laminin or fibronectin can be inhibited by antibodies to ECMRs.

3. SUMMARY OF THE INVENTION

The present invention relates to a method for inhibiting the adhesion of one cell to another comprising interfering with the interaction between the extracellular matrix receptor and its ligand.

The invention is based upon the discovery that the α4β1 extracellular matrix receptor promotes adhesion of lymphocytes to endothelial cells via attachment to a defined peptide sequence. Prior to the present invention, the ligand of the α4β1 receptor had not been identified, nor had the function of the α4β1 receptor in lymphocyte attachment been known. By preventing the interaction between the α4β1 receptor and its ligands using antibodies or defined peptide sequences, the present invention enables, for the first time, specific intervention in the migration of lymphocytes through the vascular endothelium and into tissues. The present invention, therefore, has particular clinical utility in suppression of the immune response; in various specific embodiments of the invention, the adherence of lymphocytes to endothelium may be inhibited systemically, or may, alternatively, be localized to particular tissues or circumscribed areas. Accordingly, the present invention provides for treatment of diseases involving autoimmune responses as well as other chronic or relapsing activations of the immune system, including allergy, asthma, and chronic inflammatory skin conditions.

The α4β1 integrin is a lymphocyte receptor for the carboxy terminal cell binding domain (CTCBD) of fibronectin which comprises adhesion sites in Hep 2 and a high affinity site, CS-1, in the type III connecting segment or V (for variable) region. Using a series of peptides derived from CS-1, the tripeptide leu-asp-val (LVD) (SEQ ID NO: 3) is identified herein, as a minimal peptide capable of supporting stable lymphocyte or melanoma cell adhesion. However, only cells that express an active high avidity form of the α4β1 receptor complex are capable of attaching to and spreading on the LDV minimal peptides. On a molar basis, LDV minimal peptides are either not active, or are 10–20 times less active than intact CS-1 in promoting the adhesion of lymphocytes that express a resting form of the α4β1 receptor. In cells that express the high avidity form of the receptor, LDV minimal peptides and CS-1 were equally effective in promoting cell adhesion and spreading. The avidity of the resting form of the α4β1 receptor complex could be altered by treating the cells with a specific class of monoclonal antibodies to β1 that specifically activated β1 dependent cell adhesion. The high avidity form of the α4β1 receptor complex could be induced on U937 cells, T and B lymphoblastoid cell lines, or PHA stimulated T cell blasts by treating with the specific monoclonal antibodies to β1. Resting PBL could not be induced with the antibodies to β1 to bind to the LDV minimal peptides implying that two signals are required for LDV recognition by resting T cells. Although numerous cell populations can interact with intact CS-1 only cells which express an active α4β1 receptor complex can bind the LDV sequence. This implies that cell interaction with the carboxy terminal cell binding domain of fibronectin is regulated at least by: i) α4β1 expression, ii) activation of the α4β1 receptor complex, and iii) alternate splicing of CS-1 into V+ isoforms of fibronectin containing the LDV sequence.

3.1. Abbreviations

Peptide sequences defined herein are represented by the one-letter symbols for amino acid residues as follows: A (alanine), R (arginine), N (asparagine), D (aspartic acid), C (cysteine), Q (glutamine), E (glutamic acid), G (glycine), H (histidine), I (isoleucine), L (leucine), K (lysine), M (methionine), F (phenylalanine), P (proline), S (serine), T (threonine), W (tryptophan), Y (tyrosine), V (valine).

4. DESCRIPTION OF THE FIGURES

FIG. 1. Adhesion of T lymphocytes (Molt 4), K562-1, RD or HT1080 cells to plasma fibronectin, inhibition with P1D6 monoclonal antibody and cell surface expression of α5β1.

$^{51}$Cr-labeled cells ($10^5$ cells/ml) were incubated with P1D6 monoclonal antibody (50 µg/ml) for 60 minutes at 4° C. and allowed to attach to fibronectin-coated (20 µg/ml) plastic surfaces in the presence of P1D6 (solid bars) or mouse IgG (open bars) for 30 min (HT1080 or RD) or 4 hr (Molt 4 or K562) at 37° C. Adhesion to plasma fibronectin (pFN) is expressed as $^{51}$Cr cpm bound to the plastic surfaces. Cell surface expression of α5β1 was determined by flow cytometry by staining of cells in suspension with P1D6 monoclonal antibody. Log P1D6 fluorescence (striped bars) is expressed as mean channel number (0–255) above background.

Figure 2:
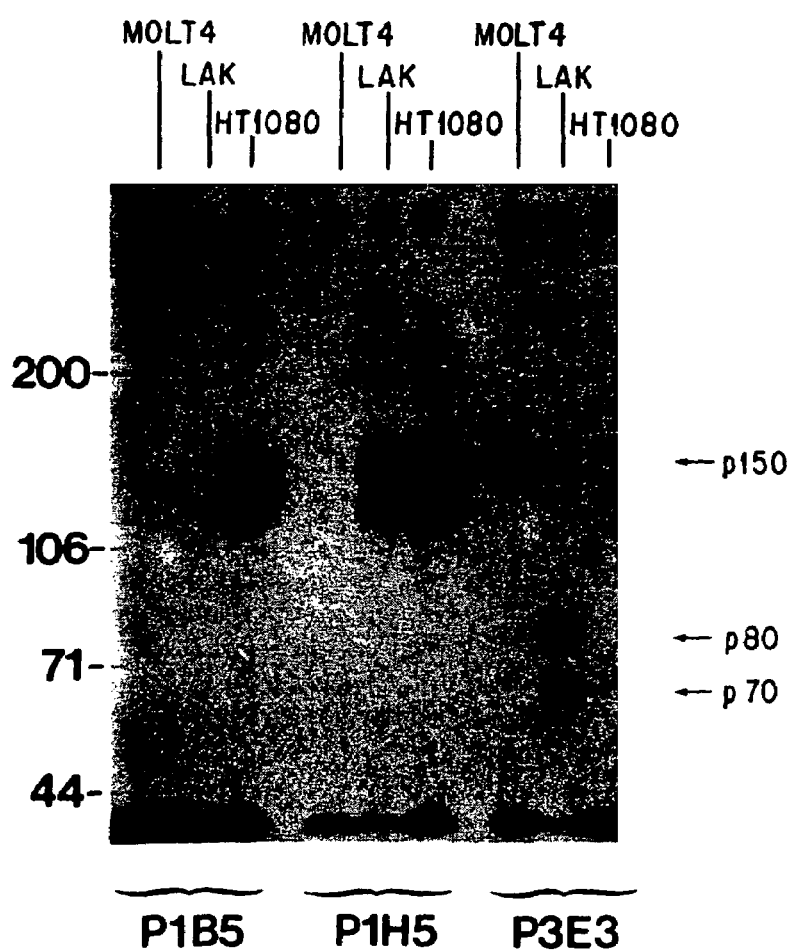

FIG. 2. Immune precipitation of lymphocyte fibronectin receptor from HT10890, Molt 4 or chronically activated CD8+ T (LAK) cell detergent extracts.

$^{125}$I-labeled Molt 4, LAK or HT1080 cells were extracted with 1% Triton X-100 in the presence of phenylmethyl sulfonyl fluoride (1 mM), N-ethylmaleimide (1 mM), leupeptin (1 µg/ml) and diisopropyl fluorophosphate (1 mM) as protease inhibitors. Aliquots of these extracts were immune precipitated with monoclonal antibodies directed to α3β1 (P1B5), α2β1 (P1H5) and α4β1 (P3E30. The immune precipitated antigens were run on 7.5% SDS-PAGE gels in the absence of 2-ME and visualized by autoradiography. The three bands immune precipitated with P3E3 from T lymphocytes are indicated (arrows).

Figure 3:
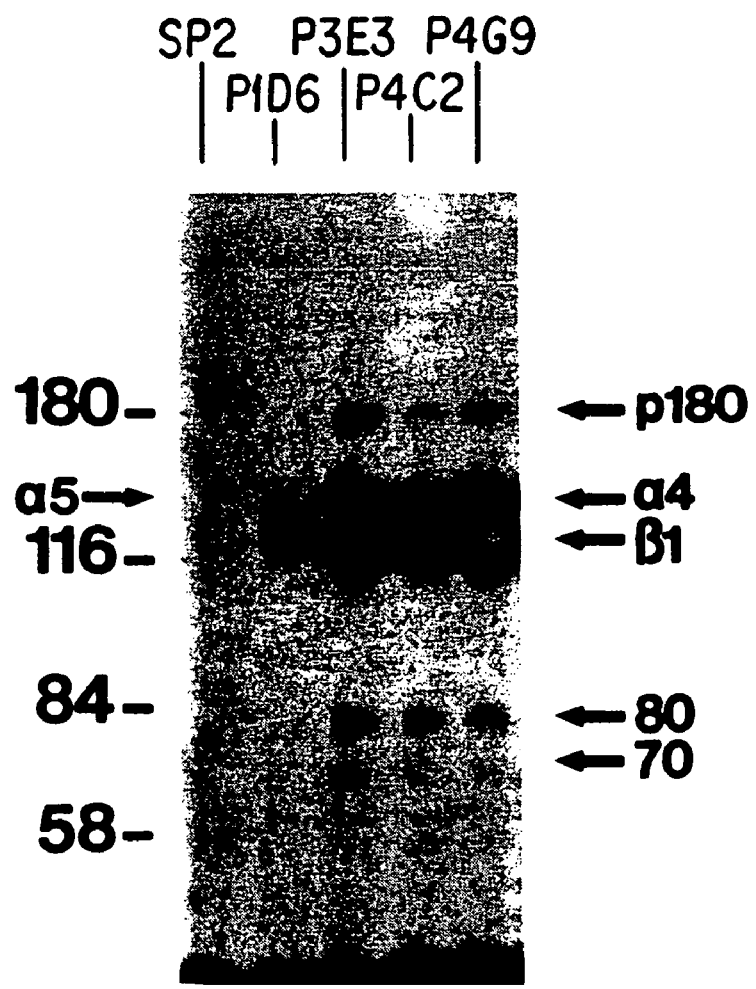

FIG. 3. Identification of lymphocyte specific fibronectin receptor as Integrin α4β1.

$^{125}$I-surface labeled Jurkat cells were extracted with 0.3% CHAPS in the presence of 1 mM $CaCl_2$, 1 mM diisopropylfluorophosphate, 1 mM phenylmethyl sulfonyl fluoride, 1 mM N-ethylmaleimide, 1 µg/ml leupetin and 2 µg/ml soybean trypsin inhibitor. Aliquots of the extracts were then immune precipitated with myeloma (SP2) culture supernatant or with monoclonal antibodies P3E3, P4C2, P4G9 or with P1D6 (anti-α5β1). The immune precipitates were run on 8% SDS-PAGE gels in the absence of reducing agent and visualized by autoradiography. Molecular weight markers are shown on the left-hand side. The α5 and β1 subunits are indicated as are the bands present in immune precipitates prepared with P3E3, P4C2 and P4G9 (arrows).

FIG. 4. Localization of α4β1 and α5β1 in focal adhesions on fibronectin-coated surfaces.

RD cells were trypsinized and allowed to adhere to silanized and fibronectin-coated (20 µg/ml) glass cover slips in the absence of serum for 1 hour at 37° C. At the end of this time the cells were prepared for localization of receptors in focal adhesions as described (Experimental Procedures). Panels A and C show focal adhesions (arrows) visualized by interference reflexion microscopy when RD cells are adhered to fibronectin. Panel B shows the reorganization of the RGD prototype fibronectin receptor α5β1 stained with antibody AB33 to the focal adhesions (arrows). Panel D shows the reorganization of α4β1 stained with P4G9 (FITC) also to the focal adhesions when RD cells are adhered to fibronectin (arrows). Panels A and B are the same field and Panels C and D are the same field.

Figure 5A:
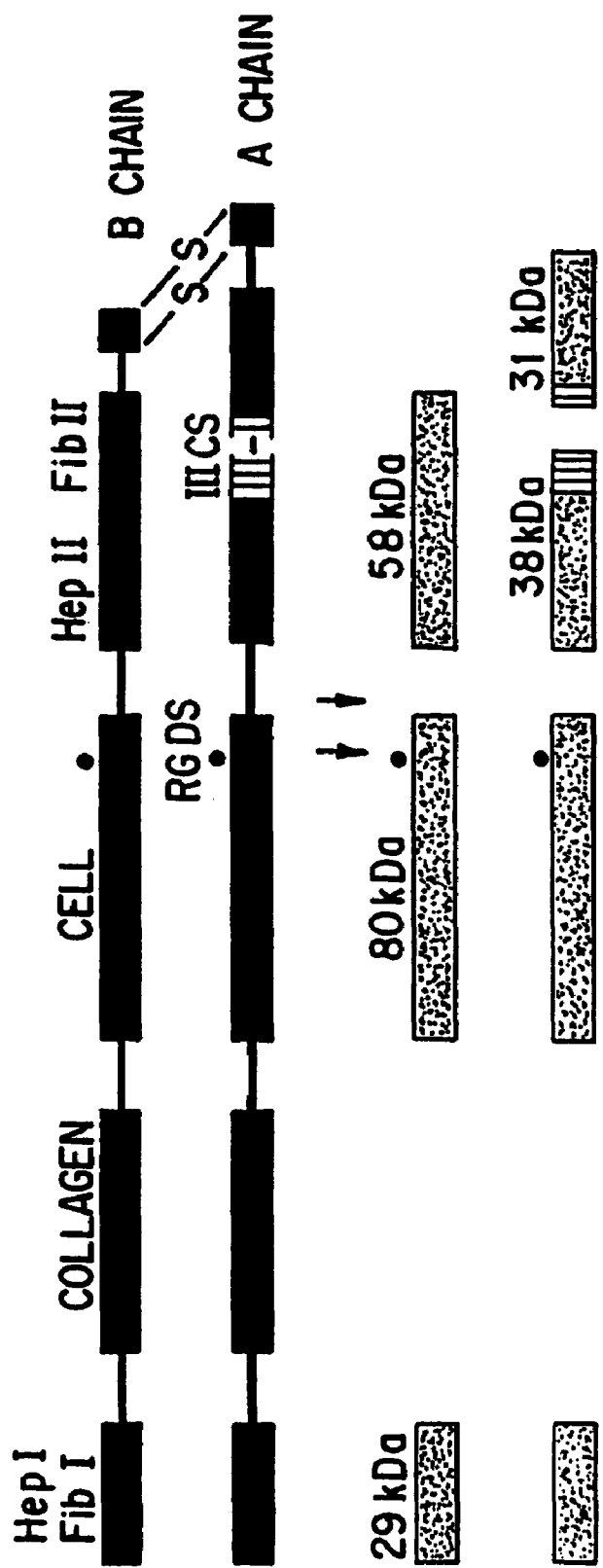

FIG. 5A. Domain structure of human plasma fibronectin (pFN) showing the origin of the fragments used in this study. B. SDS-PAGE gel analysis (10% acrylamide) demonstrating the purity of the fragments.

The 80 kDa fragment had the N-terminal amino acid sequence SD( )VPSPR( )LQF (SEQ ID NO:4), begins at position 874 of the fibronectin molecule (Kornblihtt et al., 1985, EMBO J. 4:1755–1759). This fragment contains the cell binding domain (Cell) and the RGDS sequence of fibronectin (*). The 58 kDa and 38 kDa fragments had the N-terminal amino acid sequence TAGPDQTEMTIEGLQ (SEQ ID NO:5). Both fragments contain the C-terminal Heparin binding domain (Hep II) and result from a different cleavage of the two fibronectin chains by trypsin. The 38 kDa fragment comprises the first 67 amino acid residues of the alternatively spliced connecting segment of fibronectin (IIICS) (Garcia-Pardo, 1987, Biochem. J., 241:923–928) and it is therefore derived from the A chain. The 38 kDa fragment does not contain the REDV adhesion site recognized by B16-F10 melanoma cells (Humphries et al., 1986, supra; Humphries et al., 1987, supra). The 58 kDa fragment is also derived from the B chain of fibronectin and lacks the IIICS region (Garcia-Pardo, et al., 1989, EMBO J., submitted). The 58 kDa fragment also contains the C-terminal fibrin binding domain of fibronectin (Fib II), and is similar to previously reported fragments from this region of plasma fibronectin (Click, E. M., and Balian, G. 1985, Biochem., 24:6685–6696). The bands are visualized by a silver strain.

Figure 6A:
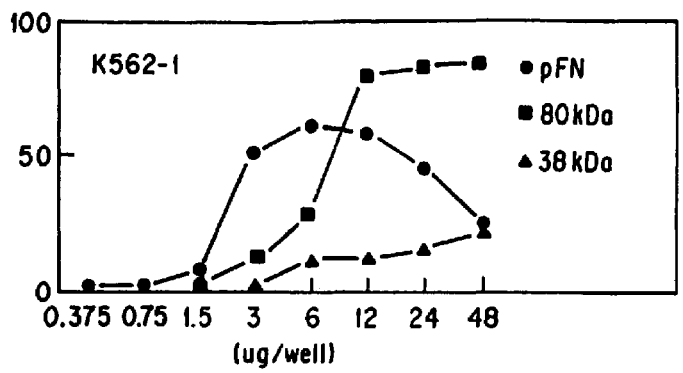
Figure 6B:
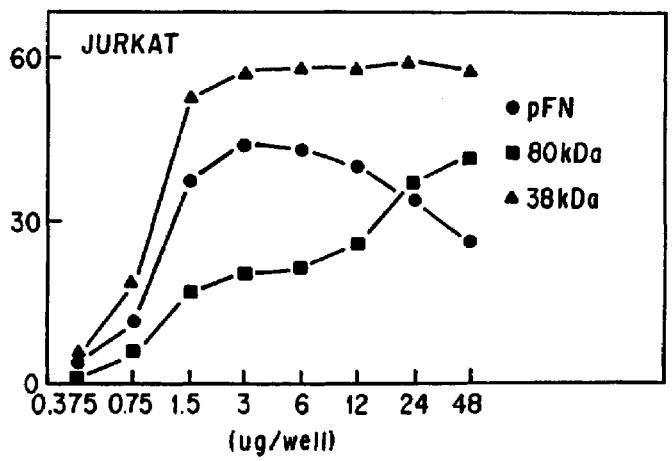
Figure 6C:
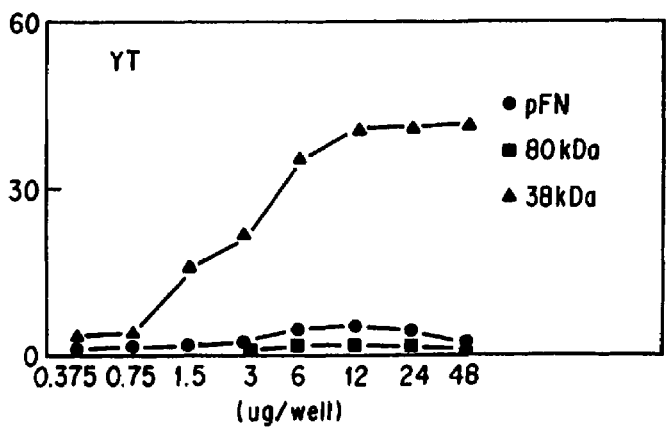

FIG. 6. Adhesion of hematopoietic cells to plasma fibronectin and the purified 38 kDa and 80 kDa tryptic fragments of plasma fibronectin.

$^{51}$Cr-labeled K562 (erythroleukemia), Jurkat (CD3+ T lymphocyte) and YT (CD3– T lymphocyte) cells ($10^5$/well) were allowed to adhere to plastic surfaces that had been coated with intact plasma fibronectin (pFN) or the purified 80 kDa and 38 kDa tryptic fragments at the indicate concentrations for 2 hours at 37° C. At the end of this time non-adherent cells were washed off and the bound cells were solubilized in SDS/NaOH and quantitated. The results are expressed as bound $^{51}$Cr cpm.

FIG. 7. Effect of the monoclonal antibodies P1D6 and P4C2 to the integrin receptors α5β1 and α4β1 (respectively) on adhesion of T lymphocytes to intact plasma fibronectin (pFN) or the purified 80 kDa and 38 kDa tryptic fragments.

$^{51}$Cr-labeled Molt 4 cells were incubated with purified P1D6 or P4C2 monoclonal antibodies (50 µg/ml) or purified mouse IgG (50 µg/ml) for 1 hour at 4° C. They were then allowed to adhere to plastic surfaces that had been coated with intact plasma fibronectin, or the 80 kDa and 38 kDa tryptic fragments at the indicated concentrations for 1 hour. At the end of this time the non-adherent cells were washed off and the adherent cells were solubilized and bound $^{51}$Cr cpm were quantitated in a gamma counter. The results are expressed as bound cpm.

Figure 8:
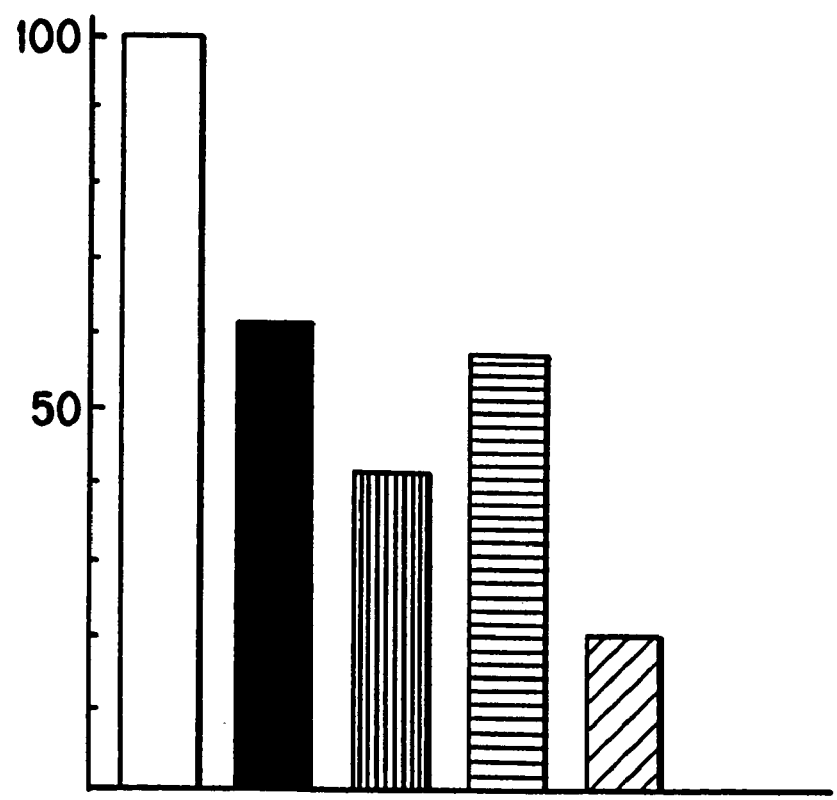

FIG. 8. Effect of CS-1 B12 peptide on T lymphocyte adhesion to IL-1β Activated HUVE cells.

Figure 9A:
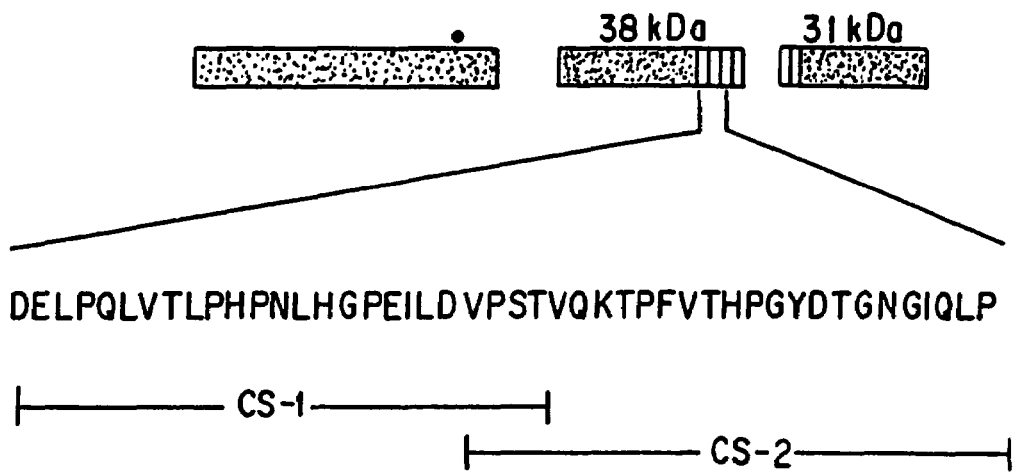
Figure 9B:
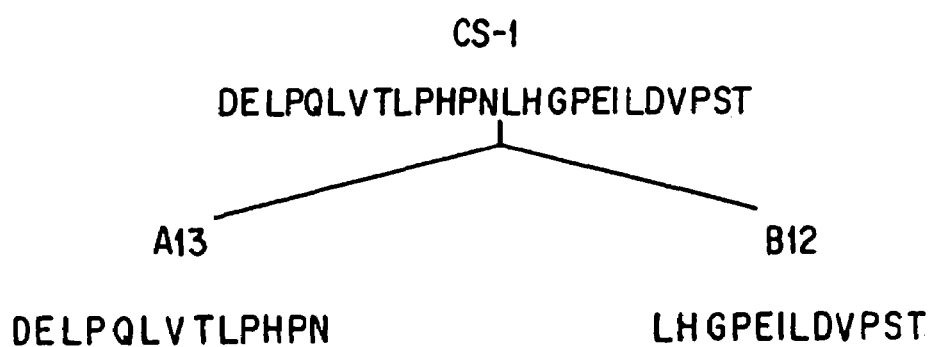

FIG. 9.
(a) Diagram of the III CS and CS-1 regions.
(b) Amino acid sequence of CS-1, A13, and B12.

Figure 10:
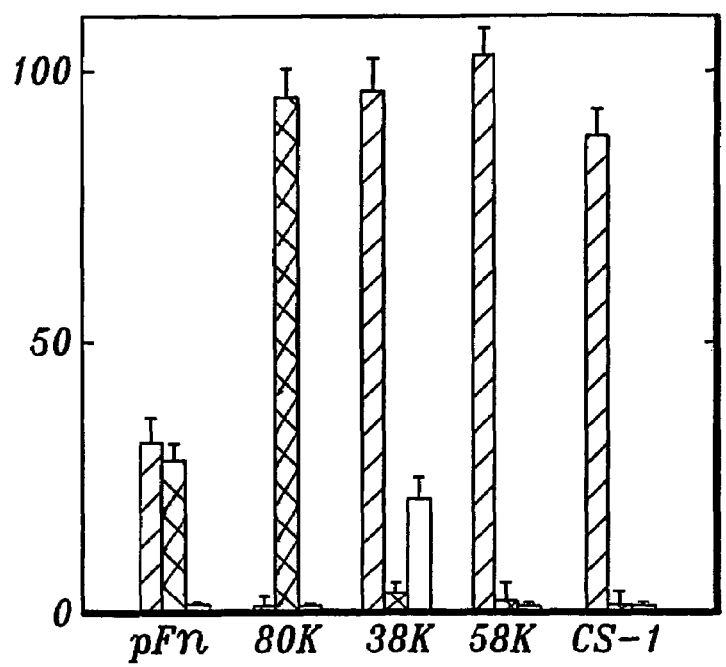

FIG. 10. Adhesion of Jurkat T lymphoblastoid cells to plasma fibronectin, fragments of plasma fibronectin, or CS-1-rsa peptide-coated surfaces in the presence of inhibitory anti-integrin monoclonal antibodies (Mabs).

Figure 11A:
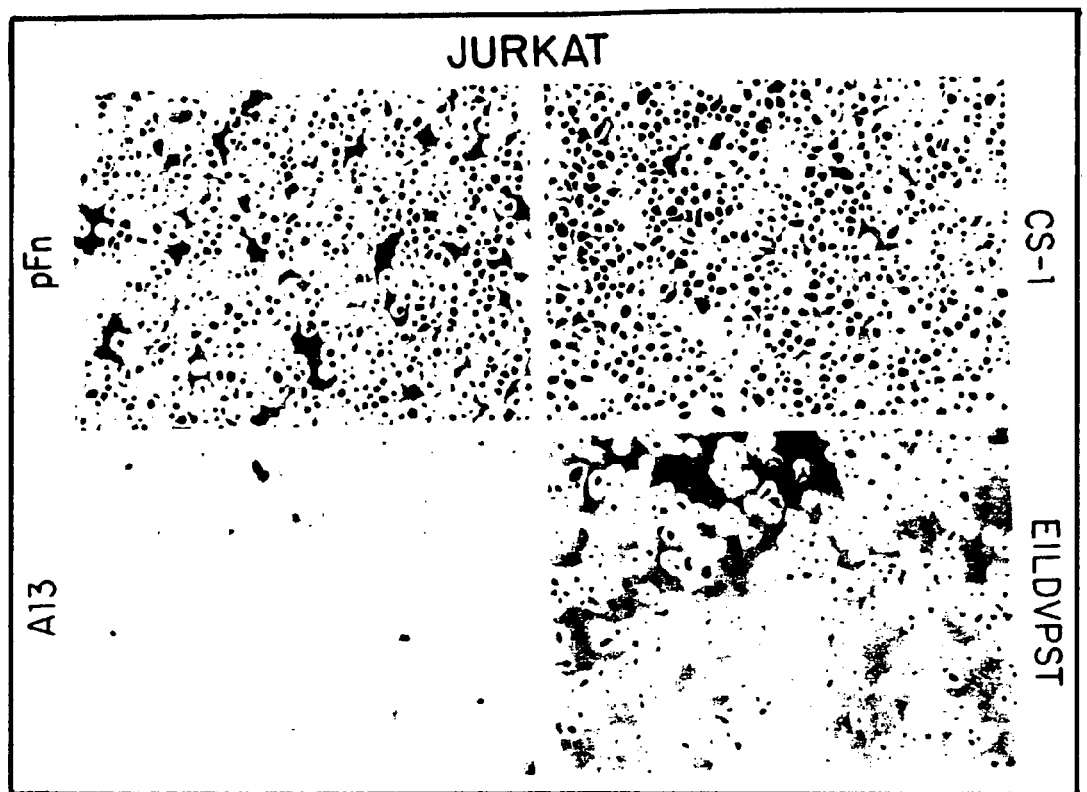
Figure 11B:
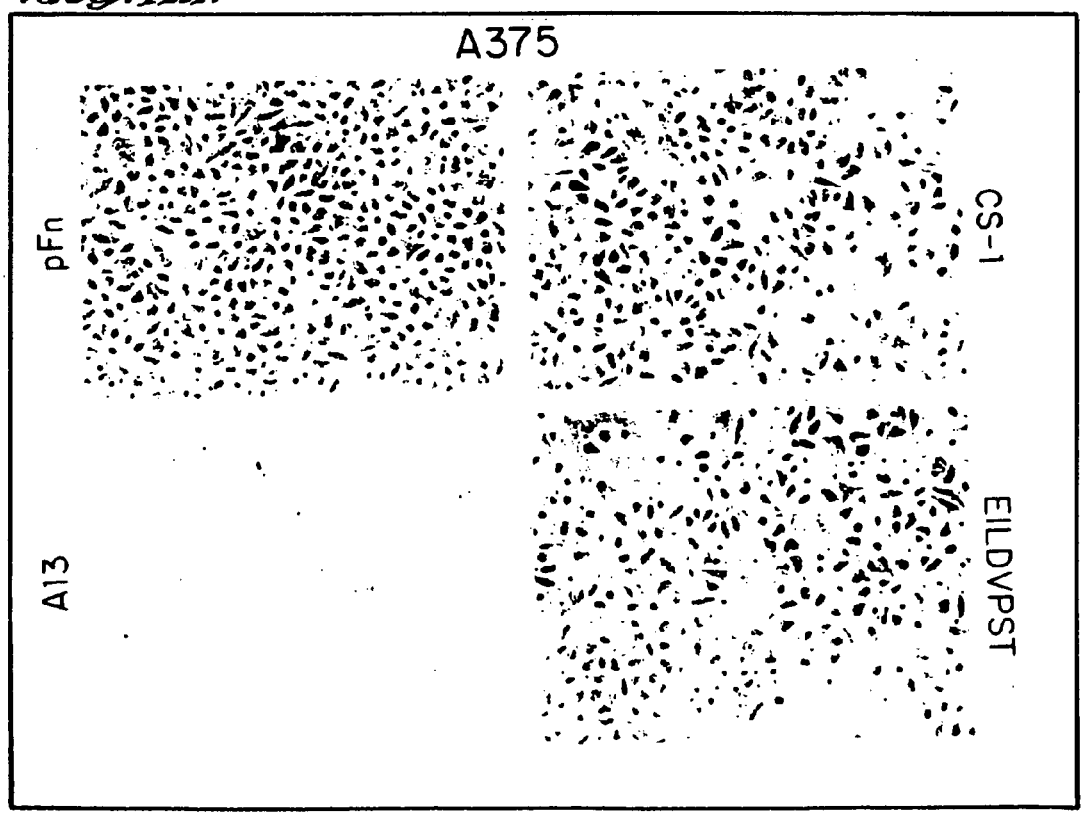

FIG. 11. Adhesion of Jurkat (Panel A) or A375 melanoma cells (Panel B) to plasma fibronectin (pFN), CS-1, A13, or EILDVPST (SEQ ID NO:6)-coated surfaces.

Figure 12:
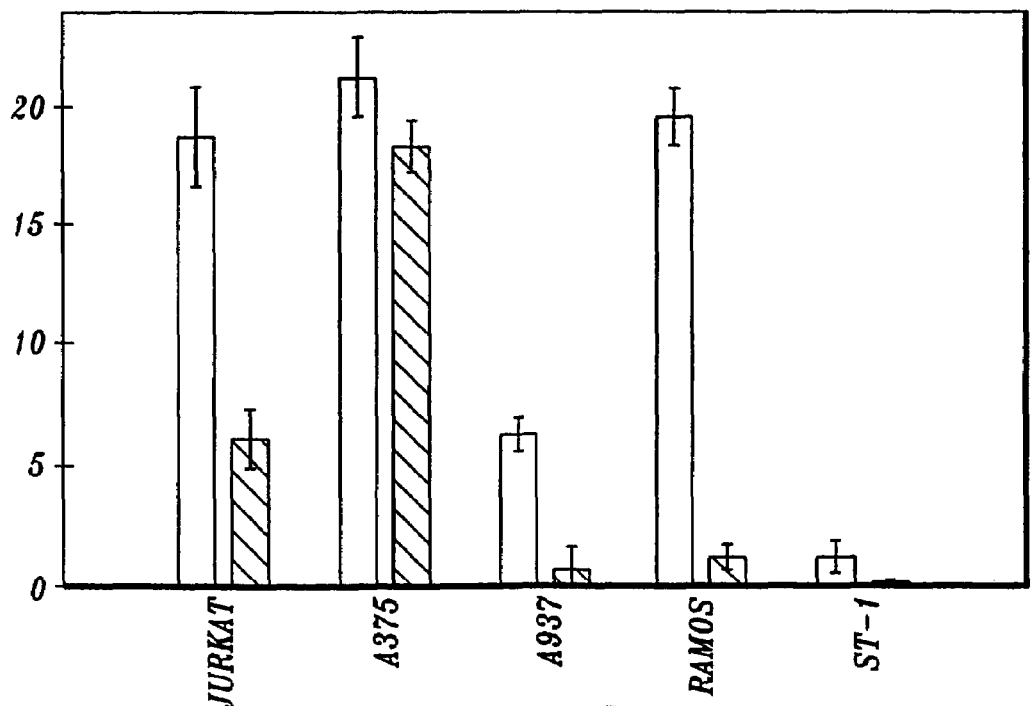

FIG. 12. Adhesion of various hematopoetic cell lines to CS-1 (open bars) or LDV (cross-hatched bars) coated surfaces.

Figure 13A:
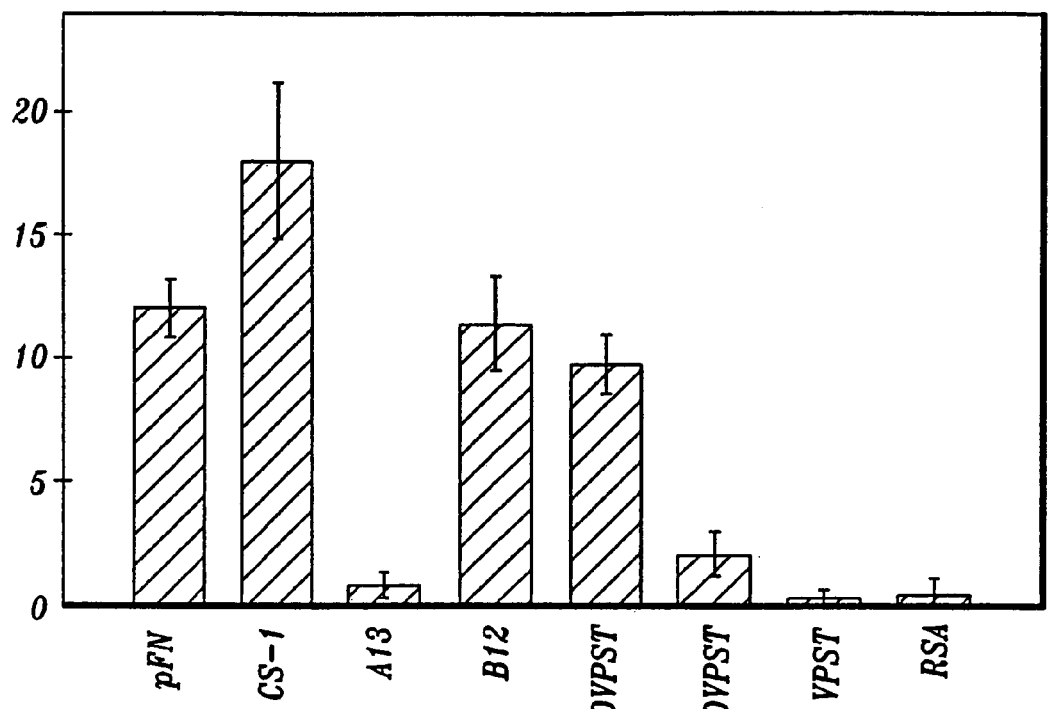

FIG. 13A. Adhesion of Jurkat cells to surfaces coated with pFN, CS-1, A13, or B12 derived peptide-rsa conjugates in the presence of monoclonal antibody 8A2; adhesion in the presence of purified non-immune mouse IgG (5 ug/ml).

Figure 13B:
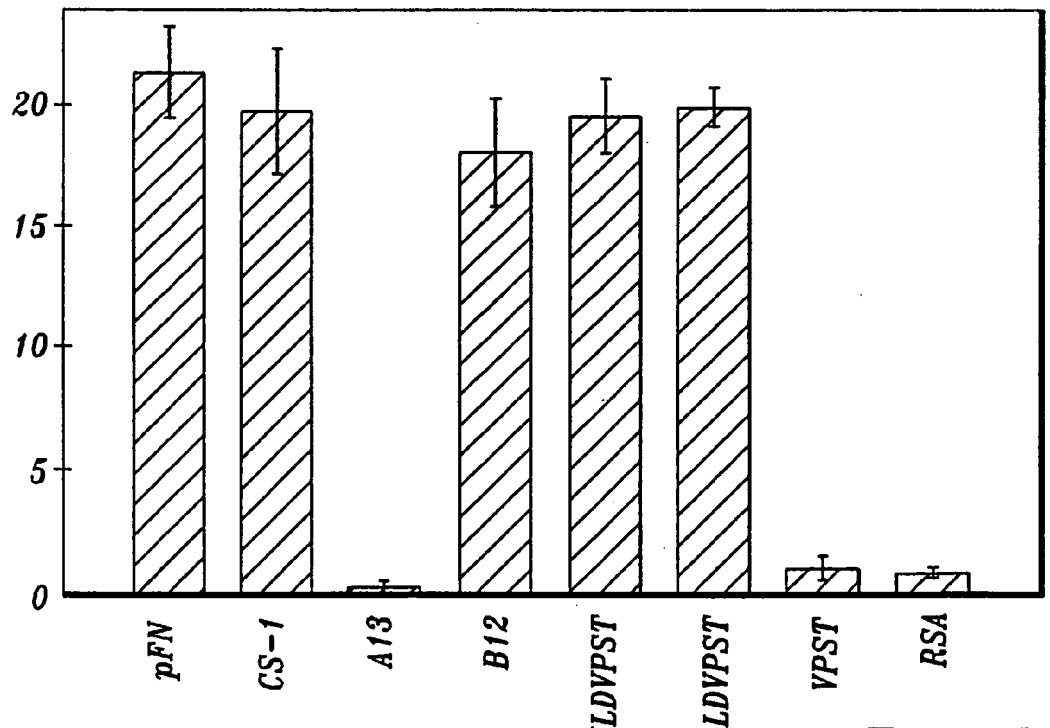

FIG. 13B. Adhesion of Jurkat cells to surfaces coated with pFN, CS-1, A13, or B12 derived peptide-rsa conjugates in the presence of monoclonal antibody 8A2; adhesion in the presence of Mab 8A2 (5 ug/ml).

Figure 14A:
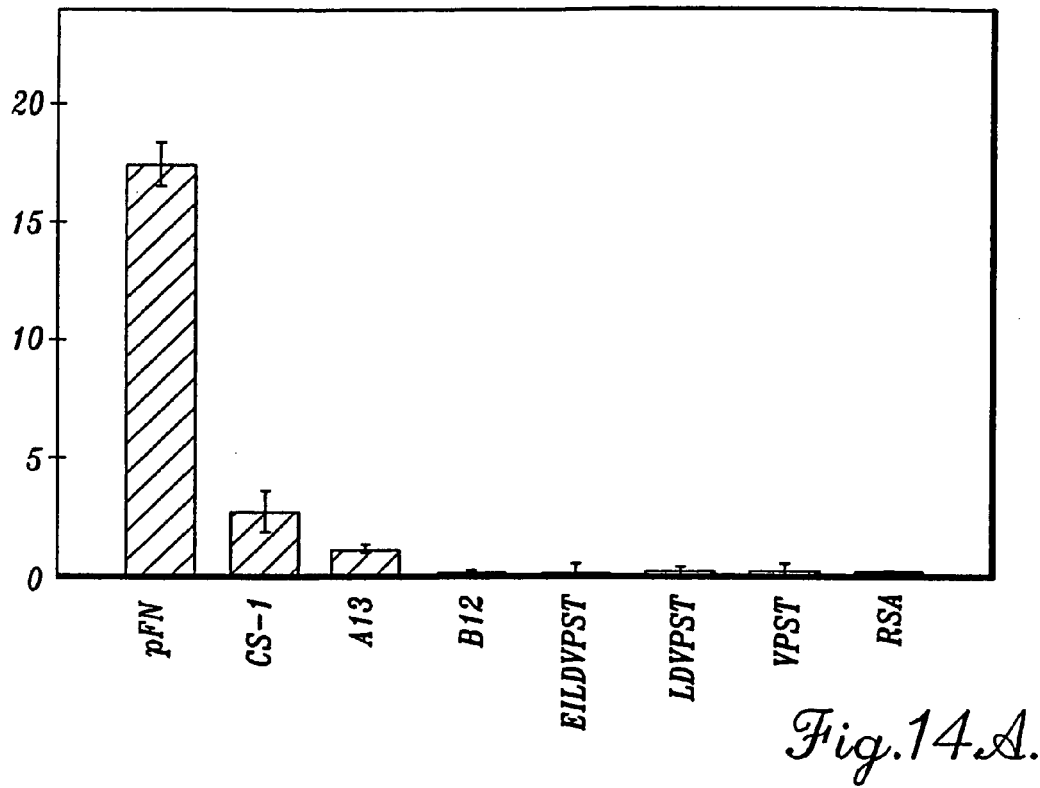

FIG. 14A. Adhesion of U937 cells to surfaces coated with pFN, CS-1, A13, or B12 derived peptide-rsa conjugates in the presence of monoclonal antibody 8A2; adhesion in the presence of purified non-immune mouse IgG (5 ug/ml).

Figure 14B:
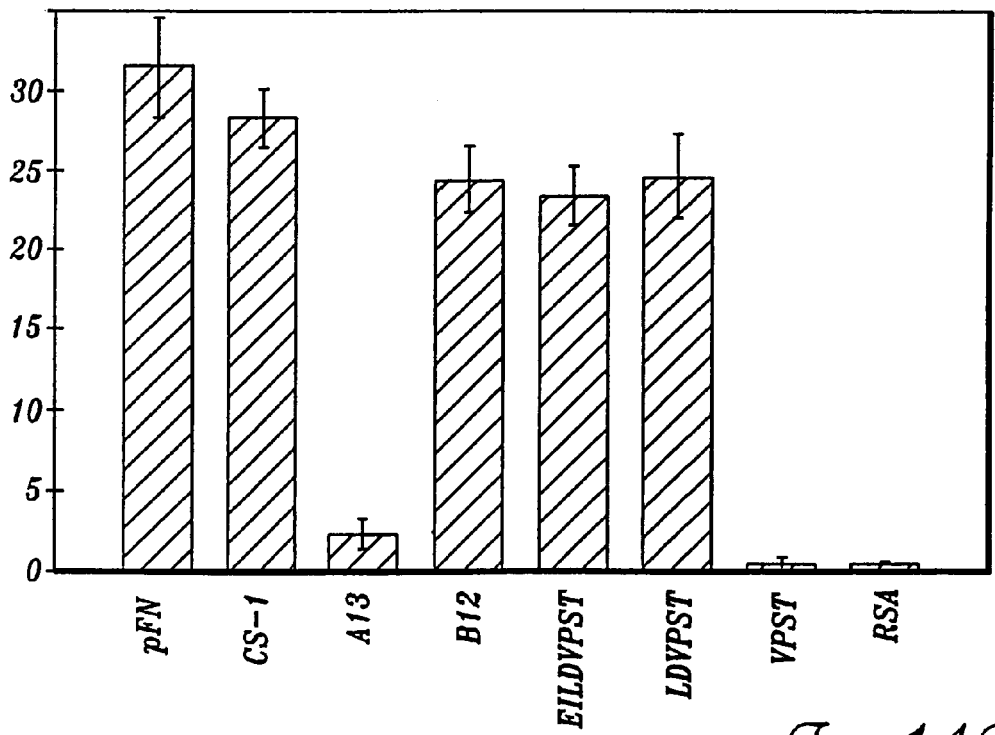

FIG. 14B. Adhesion of U937 cells to surfaces coated with pFN, CS-1, A13, or B12 derived peptide-rsa conjugates in the presence of monoclonal antibody 8A2; adhesion in the presence of Mab 8A2 (5 ug/ml).

Figure 15A:
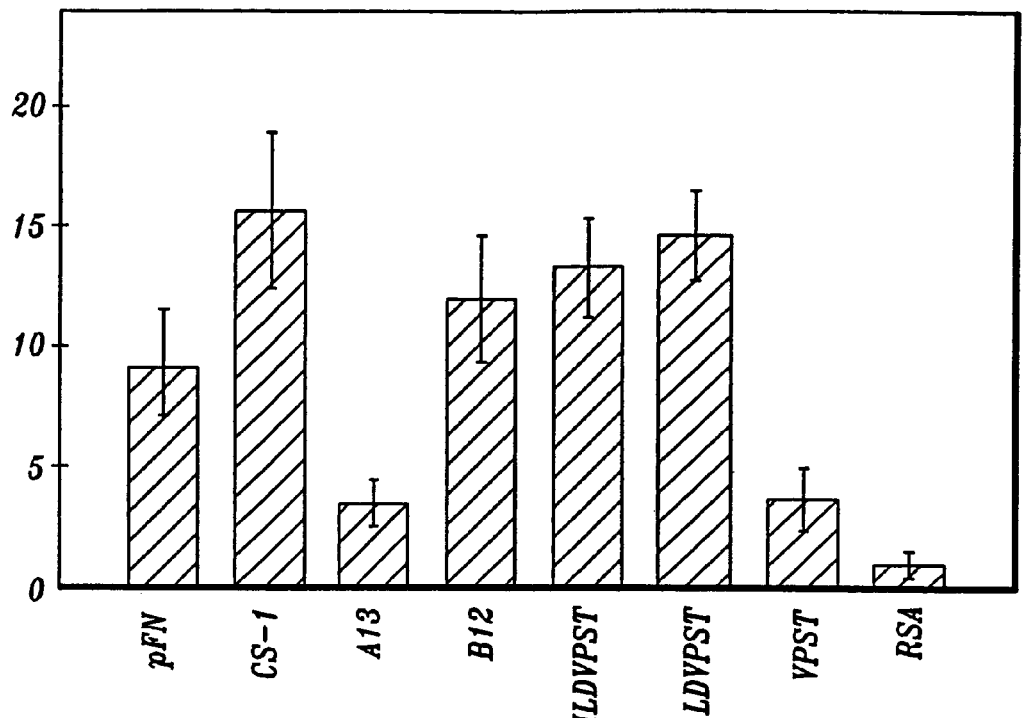

FIG. 15A. Adhesion of HUT 78 cells to surface coated with pFN, CS-1, A13, or B12 derived peptide-rsa conjugates in the presence of Mab 8A2; adhesion in the presence of purified non-immune mouse IgG (5 ug/ml).

Figure 15B:
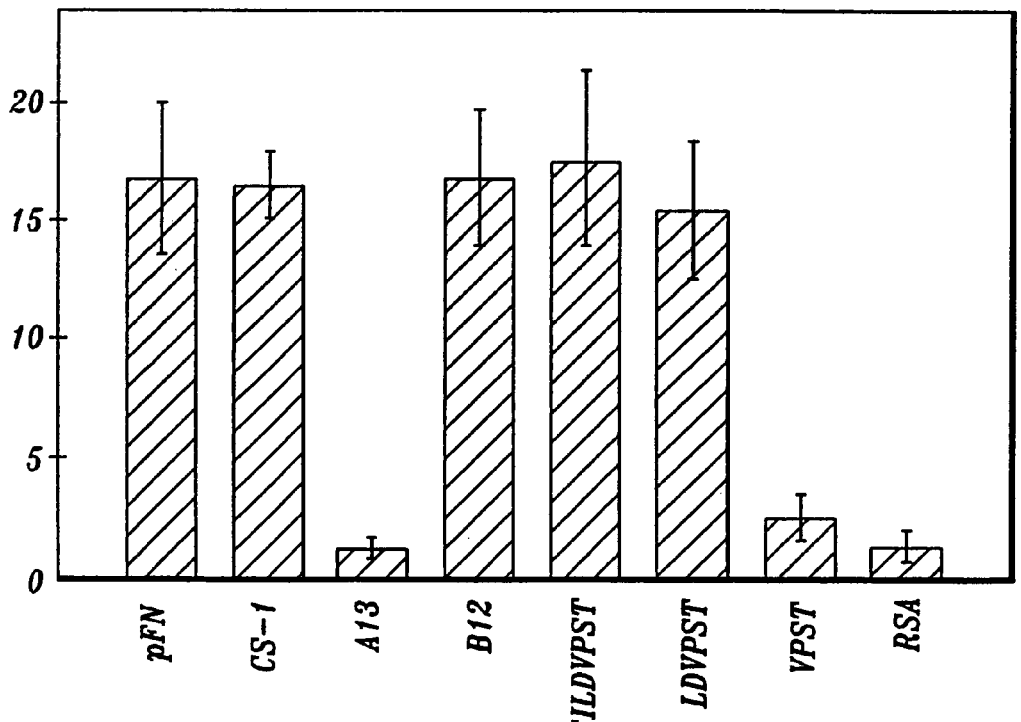

FIG. 15B. Adhesion of HUT 78 cells to surface coated with pFN, CS-1, A13, or B12 derived peptide-rsa conjugates in the presence of Mab 8A2; adhesion in the presence of Mab 8A2 (5 ug/ml).

Figure 16:
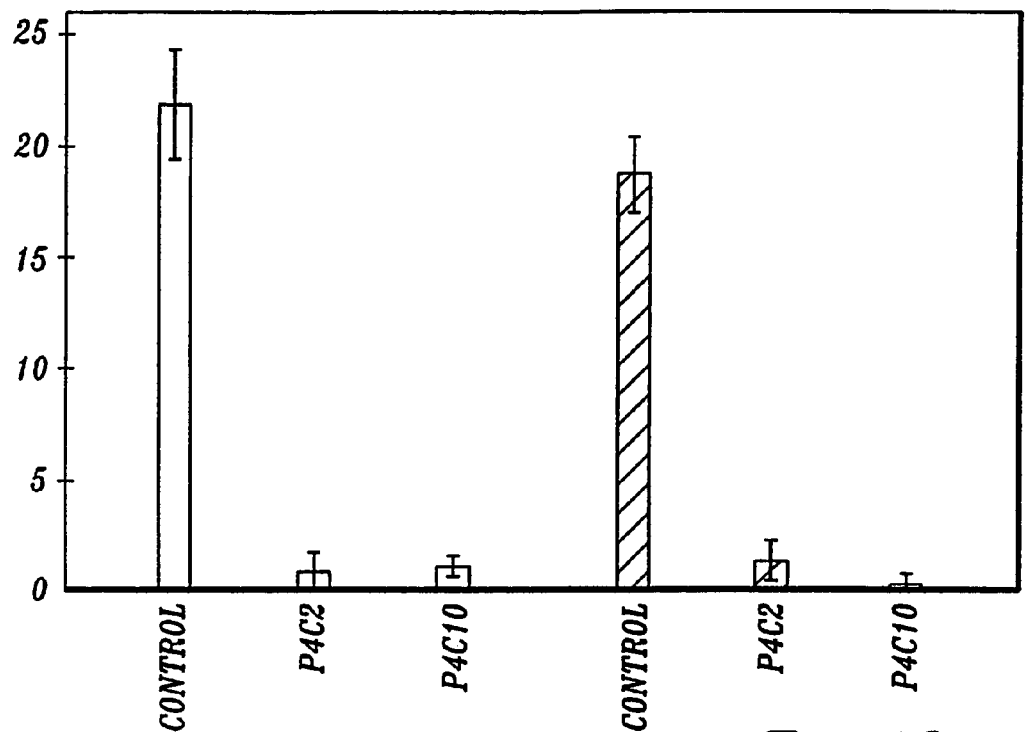

FIG. 16. Adhesion of β1 activated Jurkat or U937 cells to LDVPST-coated surfaces in the presence of inhibitory monoclonal antibodies to α4 (P4C2) or β1 (P4C10).

Figure 17:
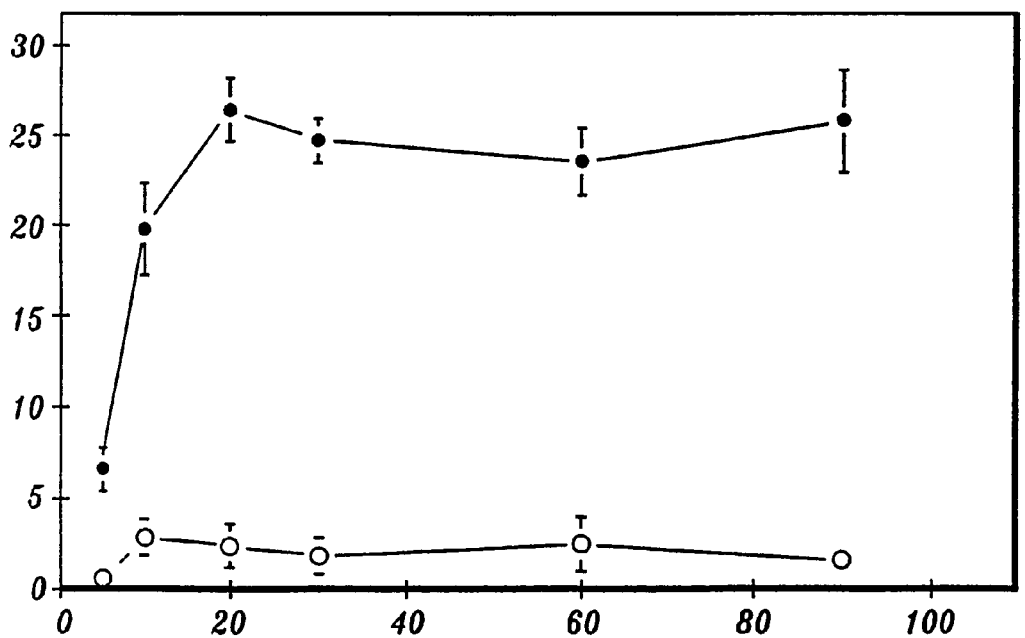

FIG. 17. Kinetic analysis of U937 cell adhesion to LDV-peptide coated surfaces in the presence of Mab 8A2.

Figure 18A:
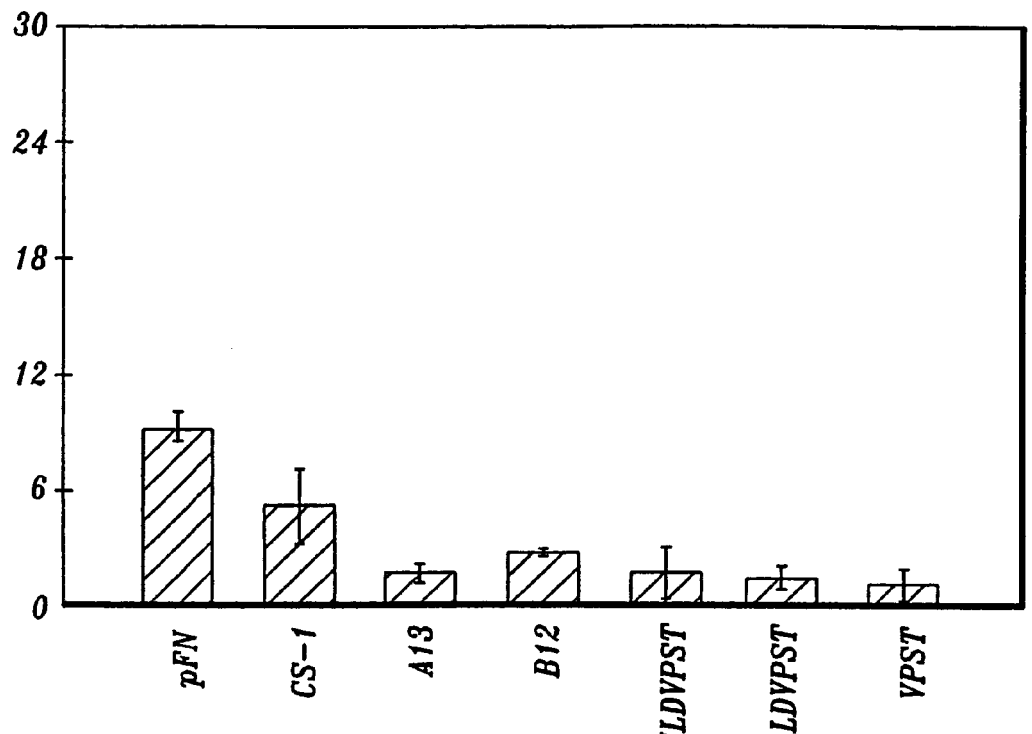

FIG. 18A. Adhesion of 72 hr PHA stimulated T cell blasts to pFN, CS-1, A13, or B12 and derivative peptide-coated surfaces; adhesion in the presence of purified non-immune mouse IgG (5 ug/ml).

Figure 18B:
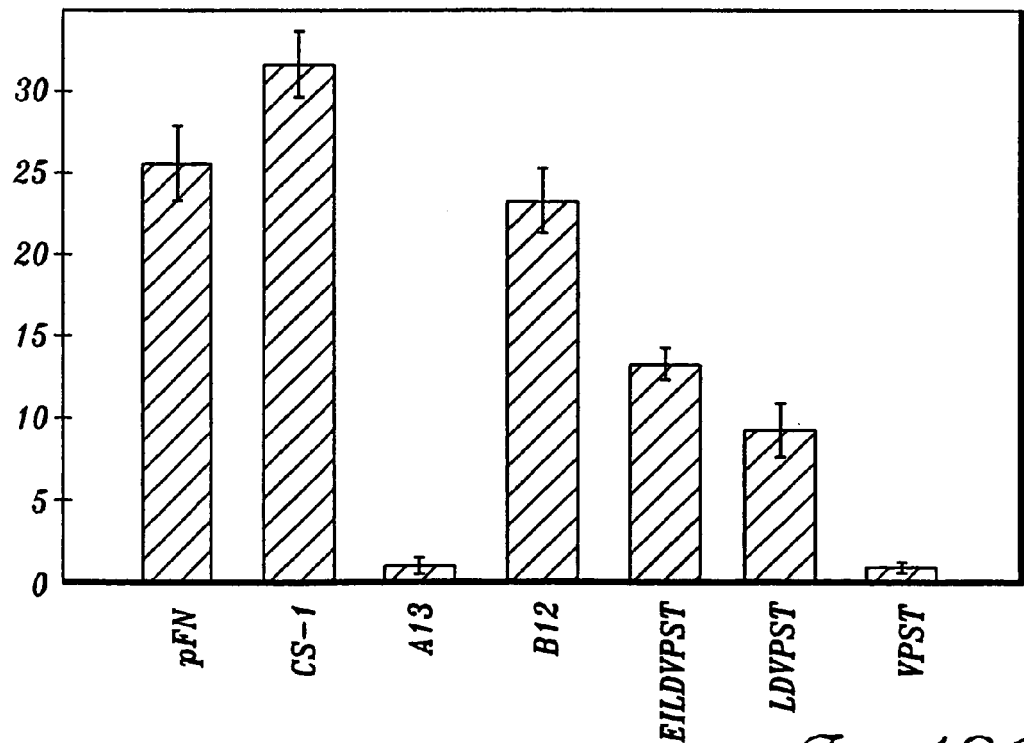

FIG. 18B. Adhesion of 72 hr PHA stimulated T cell blasts to pFN, CS-1, A13, or B12 and derivative peptide-coated surfaces; adhesion in the presence of Mab 8A2 (5 ug/ml).

5. DETAILED DESCRIPTION OF THE INVENTION

In experiments designed to examine the function of α5β1 in lymphocytes, it was observed that resting peripheral blood and cultured T lymphocytes (Molt 4 or Jurkat) expressed an affinity for fibronectin independent of the prototype fibronectin receptor, α5β1. Although these cells attached to fibronectin-coated surfaces they expressed low or undetectable levels of α5β1 recognized by the functionally defined monoclonal antibody, P1D6 (Wayner et al., 1988, J. Cell Biol. 107:1881–1891). Furthermore, T lymphocyte adhesion to fibronectin could only be partially inhibited by P1D6 or RGD (SEQ ID NO:7) containing peptides suggesting the involvement of other receptors for fibronectin in the adhesion process. Alternatively, adhesion of other cells to fibronectin, such as malignant or transformed fibroblasts and activated T lymphocytes (LAK cells) could be completely inhibited by P1D6. This suggested that resting peripheral blood T lymphocytes and cultured T cell leukemias express multiple independent and functional fibronectin receptors.

According to the present invention, an alternative fibronectin receptor was identified by preparing monoclonal antibodies that specifically inhibited the adhesion of T lymphocytes but not other cells to fibronectin. This receptor was identical to the integrin receptor, α4β1, and mediated the attachment of peripheral blood lymphocytes, cultured T cell lines and RD cells to plasma fibronectin. Furthermore, T lymphocytes expressed a clear preference for a 38 kDa tryptic fragment of plasma fibronectin (Garcia-Pardo et al., 1987, Biochem. J., 241:923–928) containing the Heparin II domain and 67 amino acid residues of the type III connecting segment (IIICS) spanning the CS-1, CS-2 and CS-3 regions defined by Humphries et al., 1986, J. Cell. Biol., 103:2637–2647; Humphries et al., 1987, J. Biol. Chem., 262:6886–6892). According to the present invention, T lymphocytes were found to attach only to CS-1 and monoclonal antibodies to α4β1 (P3E3. P4C2 P4G9) completely inhibited T lymphocyte adhesion to the 38 kDa fragment and to CS-1. T lymphocytes were also found to attach (with much lower affinity) to a site present in the Heparin II domain and monoclonal antibodies to α4β1 also inhibited this interaction. The functionally defined monoclonal antibodies to α4β1 did not inhibit T lymphocyte adhesion to an 80 kDa tryptic fragment of plasma fibronectin containing the RGD sequence, whereas antibodies to α5β1 (the prototype fibronectin receptor) completely inhibited this interaction.

In addition, the present invention relates to the discovery that the α4β1 receptor mediates the interaction between lymphocytes and endothelial cells. According to the invention, antibodies or peptides can be used to block the adhesion of lymphocytes to endothelial cells.

For purposes of clarity of disclosure, and not by way of limitation, the present invention will be described in the following subsections.

i) Preparation of antibodies to extracellular matrix receptors (ECMRs);
ii) Characterization of the ECMR-ligand interaction;
iii) Methods of intervening in cell adhesion;
iv) Utility of the invention; and
v) Peptides and antibodies of the invention.

5.1. Preparation of Antibodies to Extracellular Matrix Receptors

Preparation of antibodies to extracellular matrix receptors may be performed using any method for generating antibodies known in the art. Intact cells, or purified extracellular matrix receptor (ECMR) may be used as immunogen. Immunization of a host is preferably performed using immunogen obtained from a xenogenic source. Antibodies may be polyclonal or monoclonal.

Various procedures known in the art may be used for the production of polyclonal antibodies to epitopes of a given ECMR. For the production of antibody, various host animals can be immunized by injection with an ECMR protein, or a synthetic protein, or fragment thereof, or, alternatively, intact cells may be used. Various adjuvants may be utilized to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*Bacille Calmette-Guerin*) and *Corynebacterium parvum*.

A monoclonal antibody to an epitope of a ECMR can be prepared by using any technique which provides for the production of antibody molecules by continuous cell lines in culture. These include but are not limited to the hybridoma techniques originally described by Kohler and Milstein (1975, Nature 256:495–497) and Taggart and Samloff (1983, Science 219:1228–1230), and the more recent human B cell hybridoma technique (Kozbor et al., 1983, Immunology Today 4:72) and EBV-hybridoma technique (Cole et al., 1985, Monoclonal Antibodies and Cancer Therapy, Alan R. Liss, Inc., pp. 77–96).

The monoclonal antibodies for therapeutic use may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

A molecular clone of an antibody to an ECMR epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

Antibody molecules may be purified by known techniques, e.g., immunoabsorption or immunoaffinity chromatography, chromatographic methods such as HPLC (high performance liquid chromatography), or a combination thereof, etc.

Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the 2 Fab or Fab fragments which can be generated by treating the antibody molecule with papain and a reducing agent.

Likewise, antibodies which are reactive with ECMRs produced by the above methods may be identified and selected by any technique known in the art. For example, antibodies may be shown to bind to and/or immunoprecipitate a known ECMR which has been purified or otherwise separated from other proteins, as in a polyacrylamide gel. Alternatively, antibodies to ECMRs may be identified by their ability to compete with previously known ECMR antibodies for binding to ECMRs. Antibodies which bind to ECMRs may also be identified by their ability to block an ECMR/ligand interaction. For example, and not by way of limitation, cells bearing an ECMR receptor which binds to fibronectin (which need not, itself, have been identified or characterized, but merely functionally defined) may be shown to adhere to a substrate coated with fibronectin. If an antisera or hybridoma supernatant may be shown to inhibit the adherence of cells to the substrate, the antibodies contained in antisera or supernatant may recognize the ECMR receptor.

According to the invention, antibodies which recognize the $\alpha 4\beta 1$ receptor may be prepared by the methods outlined supra. In a preferred embodiment of the invention, monoclonal antibodies directed toward $\alpha 4\beta 1$ may be produced as follows: mice obtained from RBF/DN mice may be immunized with about 100 μl of packed T lymphocytes; their spleens may subsequently be removed and fused with myeloma cells, for example, NS-1/FOX-NY myeloma cells, as described by Oi and Herzenberg (1980, in "Selected Methods In Cellular Immunology," Mishell and Shiigi, eds, Freeman and Co., San Francisco, pp. 351–373) and Taggart and Samloff (1983, Science 219:1228–1230). Viable heterokaryons may then be selected in RPM1 1640 media supplemented with adenine/aminopterin/thymidine. Hybridomas producing antibody directed toward lymphocyte ECMRs may be screened by adhesion to fibronectin-coated surfaces and cloned by limiting dilution. In particular, antibodies directed toward $\alpha 4\beta 1$ may be identified, for example, by the ability to block adherence of lymphocytes to substrate coated with CS-1 peptide or its derivatives, or to endothelial cells. Antibodies which recognize $\alpha 4\beta 1$ will not, however, inhibit the binding of cells bearing the $\alpha 5\beta 1$ receptor to RGD-peptide coated substrate. Alternatively, antibodies directed toward $\alpha 4\beta 1$, may be identified by their ability to i) competitively inhibit the binding of known anti-$\alpha 4\beta 1$, antibodies (such as P4C2 or P4C10), or ii) bind to the same protein as known anti-$\alpha 4\beta 1$, antibodies (e.g. in a protein gel, Western blot, or in sequential immunoprecipitation experiments).

5.2. Characterization of the ECMR/Ligand Interaction

The interaction between an extracellular membrane receptor may be characterized, for example, and not by way of limitation, by the following methods:
i) Determination of receptor distribution and function;
ii) Intervention in receptor/ligand binding;

iii) Isolation and chemical characterization of receptor and/or ligand.

These methods will be described more fully in the three following subsections.

5.2.1. Determination of Receptor Distribution and Function

According to the methods of the invention, receptor distribution may be determined using any method known in the art. For example, and not by way of limitation, cell populations bearing the ECMR may be identified using monoclonal antibodies directed toward the ECMR of interest. Binding of antibody to the ECMR may be detected using immunohistochemical techniques such as immunofluorescence and immune peroxidase staining. Alternatively, populations of cells bearing the ECMR of interest may be collected using fluorescence-activated cell sorting techniques.

Because there appears to be a specific reorganization of cell surface adhesion receptors to the focal adhesions when cells are grown on the appropriate ligands (Burridge et al., 1988, Ann. Rev. Cell Biol. 4:487–525), one method for characterizing the functional interaction between a given receptor and a potential ligand involves determining whether the ECMR of interest distributes into the focal adhesions formed between cell and ligand substrate. For example, and not by way of limitation, $\alpha 4\beta 1$ may be shown to interact with fibronectin in a receptor/ligand relationship by the following method (see also section 6.2.3., infra). Lymphocytes may be allowed to adhere to a fibronectin substrate, and the focal adhesions between cells and substrate may be visualized by interference reflexion microscopy (Izzard et al., 1976, J. Cell Sci. 21:129–159). Antibodies which recognize $\alpha 4\beta 1$, such as P4G9 or P4C10, may be used to show, using standard immunohistochemical techniques, e.g. fluoro-iso thiocyanate, that in the absence of serum, $\alpha 4\beta 1$ redistributes into the focal adhesions.

Interaction between ECMR and ligand may also be characterized by testing for the ability of the ECMR to adhere to a variety of different substrates. For example, a cell type of interest or an ECMR of interest may be tested for the ability to bind to substrates consisting of purified components of the extracellular matrix, such as fibronectin, collagen, vitronectin or laminin. In a specific embodiment of the invention, cells bearing the $\alpha 4\beta 1$ may be shown to adhere to fibronectin, but not to collagen or laminin substrates as a result of the $\alpha 4\beta 1$/fibronectin interaction.

In further embodiments of the invention, in which an ECMR of interest is shown to bind to a particular protein ligand, substrates bearing subfragments of the protein ligand may be tested for the ability to bind to an ECMR on the surface of cells, thereby permitting the localization of the binding site between ECMR and ligand. In a specific embodiment of the invention, in which the receptor is $\alpha 4\beta 1$, which has been determined to bind to fibronectin (supra), substrates bearing subfragments of fibronectin may be tested for their ability to bind $\alpha 4\beta 1$-bearing cells, as exemplified in Section 6, infra. Although T lymphocytes attached to the 80 kDa cell binding domain of fibronectin bearing the $\alpha 4\beta 1$, receptor (FIG. 5A) they demonstrated a clear preference for an non-RGD containing region located on a 38 kDa tryptic fragment derived from the A (or heavy) chain of plasma fibronectin. T lymphocytes also recognized and bound to another Hep II containing 58 kDa fragment. However, the high affinity lymphocyte binding site was located on the 38 kDa fragment. On a molar basis, the 38 kDa fragment was three times more efficient than the 58 kDa fragment in mediating T lymphocyte adhesion. As shown in FIG. 5A the 38 kDa and 58 kDa fragments were derived from the A and B chains of plasma fibronectin, respectively. They therefore differ in the presence or absence of IIICS (Kornblihtt et al., 1985, supra; Garcia-Pardo, 1987, supra). Thus, it is possible that the 38 kDa and 58 kDa fragments used here share a common low affinity T lymphocyte binding site, located in the Hep II domain, and that additional high affinity T lymphocyte adhesion sites are present in the IIICS region unique to the 38 kDa fragment. In fact, T lymphocytes appear to specifically recognize and bind to CS-1, which has been defined as a high affinity adhesion site for B16 melanoma cells and avian neural crest cells (Humphries et al., 1987, supra; Humphries et al., 1988, J. Cell Biol., 106: 1289–1297; Dufour et al., 1988, EMBO J., 7:2661–2671). CS-1 is a region of molecular heterogeneity (generated by alternative splicing) present in the type III CS domain on the A chain of plasma fibronectin.

5.2.2. Intervention in Receptor/Ligand Binding

The ECMR/ligand relationship may be further characterized by identifying and evaluating agents which interfere with receptor/ligand binding.

For example, antibodies directed to an ECMR of interest may be used to inhibit ligand/receptor binding. Given the observation that a particular cell type adheres to a given ligand or cellular substrate, it may be of interest to identify the ECMR involved in the interaction. A panel of monoclonal antibodies, each directed toward a different ECMR, may be tested for the ability to block the adherence of cells to substrate. Inhibition of binding by a particular antibody would suggest that the ECMR recognized by that antibody is involved in the adhesive interaction. In a specific embodiment of the invention, lymphocyte adherence to endothelial cells in culture may be inhibited by antibodies directed toward $\alpha 4\beta 1$, but not by antibodies directed toward a variety of other ECMRs (see Section 7, below), indicating that $\alpha 4\beta 1$, is necessary for lymphocyte adhesion to endothelial cells. Additionally, monoclonal antibodies may be used to determine the relationship between ECMR and ligand substrate.

As exemplified in section 6, infra, T lymphocyte adhesion to the 38 and 58 kDa fragments could be completely inhibited by functionally defined monoclonal antibodies to $\alpha 4\beta 1$. Furthermore, T lymphocyte adhesion to CS-1 (IgG conjugate) coated surfaces could also be completely inhibited by P4C2, P3E3 or P4G9. These data show clearly that $\alpha 4\beta 1$ is the T lymphocyte receptor for CS-1. In contrast, these antibodies failed to inhibit adhesion of T cells to the 80 kDa fragment containing the prototype adhesion sequence arg-gly-asp (RGD) (SEQ ID NO. 7). Adhesion of T cells to the 80 kDa fragment could be completely inhibited by a monoclonal antibody to $\alpha 5\beta 1$ (P1D6) or by RGDS (SEQ ID NO: 8). P1D6 and RGDS failed to inhibit T lymphocyte adhesion to the 38 and 58 kDa fragments or to CS-1. Together, these data show that $\alpha 4\beta 1$ functions as the receptor for the carboxy terminal adhesion domain of plasma fibronectin receptor for alternative adhesion sequences in IIICS (CS-1) and possibly Hep II.

In further embodiments of the invention, the ECMR/ligand relationship may be characterized by determining the structure of the ligand. In particular, the ability of agents to compete with ligand in the ECMR/ligand interaction may be evaluated. For example, where the ligand is a protein, various fragments of the protein may be tested for their ability to competitively inhibit receptor/ligand binding. In a particular embodiment of the invention, in which lymphocytes are observed to bind to endothelial cells as well as to fibronectin, peptide fragments of fibronectin may be tested for the ability to competitively inhibit the binding of lymphocytes to endothelial cell substrate. As exemplified in Section 7, infra, CS-1 peptide, and, in particular, the peptide EILDVPST (SEQ ID NO: 6) was able to competitively inhibit the binding of lymphocytes to fibronectin and to endothelial cells, thereby localizing the binding site on the ligand to a region identical or homologous to EILDVPST (SEQ ID NO: 6).

5.3. Methods of Intervening in Cell Adhesion

According to the invention, adherence of one cell to another may be inhibited by intervening in the ECMR/ligand interaction. In a particular embodiment of the invention, the binding of lymphocytes to endothelial cells may be inhibited by interfering with the binding of α4β1 to its ligand. This may be accomplished by using antibodies directed toward the ECMR, or, alternatively, to its ligand (antibodies may be generated toward ligand in a manner analogous to that described in Section 5.1). In alternate embodiments of the invention, peptides which inhibit the binding of α4β1 to its ligand may be used to, in turn, inhibit adherence of lymphocytes to endothelial cells.

In a specific embodiment of the invention, anti-α4β1 antibody, or a fragment or derivative thereof, may be used to inhibit the binding of lymphocytes bearing α4β1 receptors to vascular endothelial cells. In preferred embodiments, the antibody is a monoclonal antibody, in particular antibody P4C2 (α4β1) or P4C10 (β1), or fragments or derivatives thereof, including chimeric antibodies with the same binding specificities.

In additional embodiments of the invention, peptides may be used to inhibit the binding of lymphocytes bearing α4β1 receptors to vascular endothelial cells. In a preferred embodiment, the peptide comprises at least a portion of the sequence of the IIICS variable region of fibronectin. In a more preferred embodiment, the peptide comprises at least a portion of the CS-1 peptide as defined by Humphries et al., (1987, J. Biol. Chem. 262:6886–6892), which is incorporated by reference in its entirety herein, or a peptide substantially homologous to it. In a most preferred embodiment, the peptide comprises at least a portion of the sequence EILDVPST (SEQ ID NO: 6), or a sequence substantially homologous thereto.

5.4. Utility of the Invention

According to the invention, the adherence of one cell to another may be inhibited by interfering in the binding between the ECMR and its ligand. In particular embodiments of the invention, the adherence of lymphocytes to endothelial cells may be inhibited by interfering with the binding of α4β1 on lymphocytes to its ligand on the endothelial cell surface. According to the invention, the interaction of additional ECMR with endothelial cell ligands, and the inhibition of adhesion of these cells to endothelium by interfering with the ECMR/endothelial cell interaction is envisioned. For example, the adhesion of macrophages to the endothelium may also be inhibited by intervention in the macrophage ECMR/endothelial cell interaction. Likewise, melanoma cells, which also recognize the CS-1 peptide, may be inhibited from metastasizing and entering tissues using the peptides or antibodies of the invention.

The method of the invention is therefore useful in preventing the egress of lymphocytes through the vascular endothelium and into tissue. Accordingly, the present invention provides for a method of suppressing the immune response in human patients in need of such treatment. In particular embodiments, the present invention provides for methods of treatment of diseases associated with chronic or relapsing activation of the immune system, including collagen vascular diseases and other autoimmune diseases (such as systemic lupus erythematosis and rheumatoid arthritis), multiple sclerosis, asthma, and allergy, to name but a few. The present invention also provides for methods of treatment of relatively acute activations of the immune system in patients in need of such treatment, including, for example, and not by way of limitation, graft versus host disease, allograft rejection, or transfusion reaction.

Depending on the nature of the patient's disorder, it may be desirable to inhibit lymphocyte migration into tissues systemically or, alternatively, locally. For example, in diseases involving multiple organ systems, such as systemic lupus erythematosis, it may be desirable to inhibit lymphocyte adhesion systemically during a clinical exacerbation. However, for a localized contact dermatitis, it may be preferable to restrict migration of lymphocytes only into those tissues affected.

Control of systemic versus localized use of the methods of the present invention may be achieved by modifying the compositions of antibodies or peptides administered or by altering the structure of these agents or their pharmacologic compositions. For example, the antibodies or peptides of the invention may be administered by any route, including subcutaneous, intramuscular, intravascular, intravenous, intraarterial, intranasal, oral, intraperitoneal, rectal, intratracheal, or intrathecal. However, to achieve local inhibition of lymphocyte adhesion to endothelium, it may be desirable to administer the antibodies or peptides of the invention, in therapeutic amounts and in a suitable pharmacologic carrier, subcutaneously or intramuscularly. Alternatively, to achieve systemic inhibition of lymphocyte adhesion, it may be desirable to administer the antibodies or peptides intravenously.

In various embodiments of the invention it is advantageous to use a pharmacologic carrier which facilities delivery of the antibodies, peptides, etc. of the invention. For example, when antibodies, peptides, etc. are to be delivered to the skin (e.g. for the treatment of chronic inflammatory dermatologic conditions), a pharmacologic carrier which aids in the penetration of the cuticle, epidermis, and dermis may be advantageous.

Dissemination of the peptides or antibodies of the invention may also be controlled by altering the half-life of the peptide or antibody, or its effective half-life. For example, the peptides of the invention may have a relatively short half life; if these peptides were administered in a sustained release implant, the area of tissue adjacent to the implant would be exposed to peptide, (e.g. a joint in a rheumatoid arthritis patient) whereas the peptide may be degraded before reaching more distant tissues. Alternatively, if the peptide is modified to achieve a longer half-life by chemical modifications to produce derivatives, including but not limited to amino acid substitutions, glycosylations, substitution of enantiomeric variants (i.e. D-enantiomers of constituent amino acids), additions, etc., the peptide is more likely to be widely distributed at sustained levels. As further examples the N-terminus or C-terminus of the peptides may be modified to result in greater stability.

In additional embodiments, the antibodies or peptides of the invention may be conjugated to antibodies or other ligands which might direct the antibodies or peptides to specific tissues. For example, and not by way of limitation, peptides of the invention may be conjugated to antibodies targeted toward endothelial cells. Furthermore, antibodies may be produced which mimic the ECMR, and thereby attach to endothelial cell ligands, blocking lymphocyte adhesion.

5.5. Peptides and Antibodies of the Invention

The peptides of the invention include any peptide which is capable of interacting with the ECMR of interest. In a specific embodiment of the invention, any peptide which is capable of interacting with the α4β1 receptor may be used to inhibit the binding of lymphocytes to endothelium. Preferably, these peptides may be shown to inhibit adhesion of lymphocytes to endothelium in vitro prior to in vivo use. In a preferred embodiment of the invention, the peptides comprise at least a portion of the fibronectin IIICS region. In a more preferred embodiment, the peptides comprise at least a portion of the CS-1 (SEQ ID NO: 15) peptide sequence, or a sequence substantially homologous to the CS-1 (SEQ ID NO: 15) sequence as presented in FIGS. 9(a) and (b). In a most preferred embodiment, the peptides of the invention comprise at least a portion of the sequence EILDVPST (SEQ ID NO: 6) or a peptide sequence substantially homologous thereto. "Substantially homologous" should be construed to mean that the peptides of the invention may be alterations of the specified sequence such that a functionally equivalent amino acid is substituted for one or more amino acids in the peptide sequence, thus producing a silent change. For example, one or more amino acid residues within the sequence can be substituted by another amino acid of a similar polarity which acts as a functional equivalent. Substitutes for an amino acid within the sequence may be selected from other members of the class to which the amino acid belongs. For example, the non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic and glutamic acid. In addition, as discussed in Section 5.3, the present invention also relates to derivatives of the above-mentioned peptides.

Antibodies of the invention, produced and defined as described supra, include monoclonal as well as polyclonal antibodies and fragments and derivatives thereof, including the F(ab')$_2$, Fab', and Fab fragments.

6. EXAMPLE

Identification and Characterization of the Lymphocyte Adhesion Receptor for an Alternative Cell Attachment Domain in Plasma Fibronectin The following experiments have described a new fibronectin receptor which appears to be identical to the integrin receptor α4β1 (Hemler et al., 1987, supra), preferentially expressed by nucleated hematopoietic cells. Identification of α4β1 as a specific fibronectin receptor was based on (i) inhibition of cell adhesion to fibronectin by monoclonal antibodies (P4C2, P3E3 and P4G9), and (ii) specific reorganization and concentration of α4β1 into fibronectin-dependent focal adhesions. These findings suggest that α4β1 and α5β1 the prototype fibronectin receptor function together as primary mediators of cell adhesion to fibronectin.

6.1. Materials and Methods

6.1.1. Reagents

Phenylmethyl sulfonyl fluoride, n-ethylmaleimide, leupeptin, diisopropyl fluorophosphate, 2-mercaptoethanol, bovine serum albumin (BSA), Triton X-100, Protein A-Agarose, soybean trypsin inhibitor, and V8 protease (from *Staphylococcus aureus*, strain V8, protease type XVII) were purchased from Sigma Chemical Co. (St. Louis, Mo.). Lactoperoxidase and glucose oxidase were from Calbiochem (San Diego, Calif.). TPCK-trypsin was from Cooper Biomedical, Malvern, Pa. Fluorescein-conjugated (goat) anti-mouse IgG and IgM (H and L chains) or rhodamine-conjugated (goat) anti-rabbit IgG and IgM (H and L chains) were obtained from Tago, Inc. (Burlingame, Calif.). R-phycoerythrin-conjugated strepavidin was from Biomeda (Foster City, Calif.). Rabbit anti-mouse IgG (H+L) antiserum was obtained from Cappel (Cooper Biomedical, Malvern, Pa.). $^{51}$Cr-sodium chromate was from New England Nuclear. $^{125}$I was from Amersham (Arlington Hts., IL). Human recombinant interleukin-2 (IL-2) was a generous gift from Dr. D. Urdal (Immunex Corp., Seattle, Wash.). Laminin was purchased from Collaborative Research, Inc. Bedford, Mass.) and purified plasma fibronectin and collagen Types I and III were prepared as previously described (Wayner, E. A. and Carter, W. G., 1987, supra and Wayner et al., 1988, supra).

6.1.2. Cells and Cell Culture

RD (Human rhabdomyosarcoma) and HT1080 (human fibrosarcoma) cells were obtained from the American Type Culture Collection (Rockville, Md.). Peripheral blood mononuclear cell (PBMC), platelet and granulocyte populations from normal human donors were prepared as described (Kunicki et al., 1988, supra; Wayner et al., 1988, supra). Peripheral blood cells from patients with acute lymphocytic, large granular lymphocyte (LGL) or myelogenous leukemia were obtained from Dr. I. Bernstein and Dr. T. Loughran (Fred Hutchinson Cancer Research Center). Human lymphokine (500 U/ml IL-2) activated killer (LAK) cells and the monoclonal HLA B7 specific human cytotoxic T lymphocyte (CTL) cell line, C1C4, were prepared according to standard protocols (Grimm et al., 1982, J. Exp. Med., 155:1923–1941; Glasebrook, A. L. and Fitch, F. W., 1980, J. Exp. Med., 151:876–895; Brooks, 1983, Nature, 305:155–158; Wayner, E. A. and Brooks, C. G., 1984, J. Immunol., 132:2135–2142; Wayner, E. A. and Carter, W. G., 1987, J. Cell Biol., 105:1873–1884). The EBV transformed B lymphocyte cell line (BLCL), ST-1, was derived from the donor spleen used in the production of the C1C4 CTL line. All other cell lines and cell culture conditions were as previously described (Wayner, E. A. and Carter, W. G., 1987, supra; Wayner et al., 1988, supra).

6.1.3. Antibodies

A rabbit polyclonal antibody, AB33, prepared against the cytoplasmic domain of the fibronectin receptor, α5β1, was used to detect α5β1 in focal adhesions. Monoclonal antibodies A1A5, against the common integrin (Hynes, R. O., 1987, supra) β1 subunit of the VLA family of receptors (Hemler, M. E., 1988, supra) and B5-G10 to the VLA 4 α subunit (Hemler et al., 1987, supra) were obtained from Dr. Martin Hemler of the Dana-Farber Cancer Inst., Boston, Mass.). Monoclonal antibodies to the integrin receptors α3β1 (P1B5), α2β1 (P1H5) and α5β1 (P1D6) have been described and were developed in this laboratory. P1H5 and P1D6 inhibit fibroblast and platelet adhesion to collagen and fibronectin-coated substrates, respectively (Wayner, E. A. and Carter, W. G., 1987, supra; Kunicki et al., 1988, supra; Wayner et al., 1988, supra).

Monoclonal antibodies to lymphocyte adhesion receptors were produced by the methods of Oi and Herzenberg (Oi, V. T. and Herzenberg, L. A. 1980, Immunoglobulin producing hybrid cell lines. In: *Selected Methods in Cellular Immunology*. Ed. by B. B. Mishell and S. M. Shiigi, W.H. Freeman and Co., San Francisco, pp. 351–373) and Taggart and Samloff (Taggart, R. T. and Samloff, I. M., 1983, Science, 219, 1228–1230) as described (Wayner and Carter, 1987; Wayner, et al., 1988). Spleens from RBF/DN mice immunized with 100 µl of packed T lymphocytes were removed and fused with NS-1/FOX-NY myeloma cells. Viable heterokaryons were selected in RPMI 1640 supplemented with adenine/aminopterin/thymidine (Taggart and Samloff, 1983). Hybridomas producing antibody directed to lymphocyte adhesion receptors were screened by specific inhibition of lymphocyte adhesion to fibronectin-coated surfaces and cloned by limiting dilution.

Although A1A5 (Hemler et al., 1987, J. Biol. Chem. 262:3300–3309) reacts specifically with the β1 subunit of the integrin receptors, and has been reported to inhibit cell adhesion, Takeda et al. (1988, J. Cell. Biochem. 37:385–393), this reagent has never been observed to inhibit adhesion of lymphocytes to any surface. Therefore a functionally defined anti-β1 monoclonal antibody, P4C10, was produced using the previously described techniques (supra) and by screening inhibition of cell adhesion to multiple ligands. P4C10 has been shown to inhibit adhesion of cells to fibronectin, CS-1, collagen and laminin coated surfaces and reacts with β1 by standard biochemical criterion.

6.1.4. Inhibition of Cell Adhesion to Intact Fibronectin and Fibronectin Fragments Antibodies that would alter cell adhesion to purified plasma fibronectin, tryptic fragments and CS peptides were identified as previously described (Wayner and Carter, 1987). Briefly, 48 well virgin styrene plates were coated with human plasma fibronectin (5 µl/ml). The plates were blocked with PBS supplemented with 10 mg/ml heat denatured BSA (HBSA). T lymphocyte or HT1080 cells were labeled with $Na_2$ $^{51}CrO_4$ (50 µlCi/ml for 2–4 hr), washed, and $5\times10^4$ HT1080 or cultured T cells or $5\times10^{10}$ PBL/well were incubated with hybridoma culture supernatants (1:2 dilution in PBS supplemented with 1 mg/ml heat denatured BSA) or control myeloma cell culture supernatant for 15 minutes at room temperature. The cells were allowed to adhere to the protein-coated surfaces in the presence of the hybridoma supernatants for 15–30 minutes (HT1080) or 2–4 hours (lymphocytes) at 37° C. Non-adherent cells were removed by washing with PBS, and the adherent cells were dissolved in SDS/NaOH and bound $^{51}$Cr-cpm were quantitated in a gamma counter.

6.1.5. Immune Precipitation, and Sequential Immune Precipitation, V8 Protease Peptide Mapping and Polyacrylamide Gel Electrophoresis Viable cells were surface labeled with 125-iodine as described (Wayner and Carter, 1987) followed by extraction with 1% v/v Triton X-100 detergent or 0.3% CHAPS detergent in 50 mM phosphate buffered saline pH 7.2. In some cases 1 mM $CaCl_2$ was added to the lysis buffer. 1 mM phenylmethyl sulfonal fluoride, 1 mM N-ethylmaleimide, 1 µl/ml leupeptin and 1 µg/ml trypsin soybean inhibitor were used as protease inhibitors. Immune precipitation and sequential immune precipitations were performed exactly as previously described (Wayner and Carter, 1987, supra). Peptide analysis followed the basic procedure of Cleveland et al. (1977, J. Biol. Chem. 252:1102–1106) with modifications as described (Wayner and Carter, 1987). Polyacrylamide slab gels containing sodium dodecyl sulfate (SDS-PAGE gels) were prepared following the basic stacking gel system of Laemmli (1970, Nature 227:680–685).

6.1.6. Preparation of Tryptic Fragments from Human Plasma Fibronectin and Synthesis of CS Peptides Human plasma fibronectin was a generous gift from Drs. Horowitz and R. Schulman (New York Blood Center, N.Y.).

Fibronectin was digested with TPCK-trypsin for 90 min at 37° C., and the digest was fractionated by affinity and ion-exchange chromatography as previously described (Garcia-Pardo et al., 1987, Biochem. J. 241:923–928; Garcia-Pardo et al., 1989, Exp. Cell Res. 181:426–431). Two overlapping peptides spanning the initial 48 residues of the IIICS region of human fibronectin (CS-1 and CS-2) were synthesized and coupled to rabbit IgG as described (Humphries et al., 1986, and Humphries et al., 1987, J. Biol. Chem. 262:6886–6892).

6.1.7. Fluorescence Analysis of Receptor Expression

Expression of ECMRs on cells in suspension was analyzed by one or two color flow cytometry on an EPICS 750 dual laser cell sorter (Coulter, Hialeah, Fla.). Positive fluorescence was determined; on a 3 decade log scale and fluorescence intensity (log FI) was expressed as mean channel number (0–255). Background fluorescence for a non-immune mouse IgG negative control was determined for each cell population and subtracted. Adherent cells were trypsinized and allowed to recover for 15 minutes at 37° C. in the presence of serum before use for flow cytometry. For one or two-color fluorescence measurements, $10^6$ cells in suspension were incubated for 30 minutes with protein G-SEPHAROSE (a beaded agarose matrix coupled to protein G) purified goat IgG (20 µg/ml) and then with first stage antibodies at 4° C. for 60 minutes, washed in Hanks Balanced Salt solution containing 10 mg/ml HBSA and 0.02% sodium azide (Hanks/BSA/SA) and incubated with FITC-conjugated rabbit anti-mouse IgG for 60 minutes at 4° C. in Hanks/BSA/SA. They were washed and fixed in cold 2% paraformaldehyde (prepared fresh) in PBS. For two-color fluorescence purified and biotinylated monoclonal antibody was then added to the FITC-stained and fixed cells to a final concentration of 1 ug/ml in Hanks/BSA/SA and incubated at 4° C. for 60 min. Prior fixation with 2% paraformaldehyde had little effect on expression of lymphocyte integrin receptors. The fixed cells were washed and incubated in 0.5 ml Hanks/BSA/SA containing phycoerythrin-conjugated strepavidin (Bionetics) at 1/50 dilution for 30 min at 4° C. Finally the stained cells were washed and fixed again in 2% paraformaldehyde in PBS and held at 4° C. in the dark for analysis on the EPICS flow cytometer.

6.1.8. Localization of Receptors in Focal Adhesions

Adherent cells were trypsinized, washed in RPMI supplemented with 1 µg/ml BSA plus 100 ug/ml soybean trypsin inhibitor and allowed to adhere to acid washed and silanized glass cover slips coated with fibronectin, laminin or collagen (20 ug/ml) in the absence of serum for 1–4 hour as described (Carter and Wayner, in preparation). At the end of the incubation non-adherent cells were removed and adherent cells were fixed in 100 mM sodium cacodylate, 100 mM sucrose, 4.5 mM $CaCl_2$, 2% formaldehyde for 20 min. They were permeabilized with 0.5% Triton X-100 for 5 minutes, then washed and blocked with 25% goat serum in PBS. The permeabilized cells were stained with antibodies to specific receptors (60 minutes at room temperature), washed and incubated with either FITC-conjugated goat anti-mouse or rhodamine-conjugated goat anti-rabbit IgG (45 minutes at room temperature) and washed again. The cover slips were inverted onto glass slides for fluorescence and interference reflexion microscopy (IRM) as described (Izzard, S. C. and Lochner, L. R., 1976, J. Cell. Sci., 21, 129–159).

6.1.9. Tissue Staining

The distribution of the integrin receptors in tissue was determined by fluorescence microscopy of cryostat sections. Cryostat sections (6 µm) were prepared from human skin, tonsil, or tumor samples embedded in OCT medium after snap freezing in isopentane/liquid nitrogen. All sections were fixed in 4% paraformaldehyde in PBS prior to incubation with primary antibodies and secondary fluorescent antibodies as described (Carter and Wayner, 1988, J. Biol. Chem. 263:4193–4201). In control experiments, no fluorescence of rhodamine was detected using the fluorescein filters or vice versa.

6.2. Results 6.2.1. Identification of an Alternative Fibronectin Receptor

Cultured T lymphocytes (Molt 4), K562, RD (rhabdomyosarcoma) and HT1080 (fibrosarcoma) cells and freshly derived PBL (not shown) adhered to fibronectin-coated surfaces (FIG. 1: open bars). However, Molt 4 and RD cells expressed low or undetectable levels of the prototype fibronectin receptor (integrin $\alpha 5\beta 1$) recognized by monoclonal antibody P1D6 (FIG. 1: striped bars). Consistent with this, adhesion of Molt 4 and RD cells to fibronectin could not be completely inhibited by P1D6 (FIG. 1: solid bars). Alternatively, adhesion of cells to fibronectin that expressed abundant $\alpha 5\beta 1$ (HT1080 and K562) could be effectively inhibited by P1D6. Furthermore, the synthetic peptide RGDS did not completely inhibit T lymphocyte adhesion to plasma fibronectin (50–70% for Molt 4 or Jurkat cells versus 80–90% for fibroblasts and 100% for K562-1 cells). Together, these data suggested that some cells, such as T lymphocytes, express fibronectin adhesion receptors other than $\alpha 5\beta 1$.

We attempted to identify other putative fibronectin receptors by preparing monoclonal antibodies to cultured T lymphocytes and screening them for their ability to specifically inhibit lymphocyte but not fibroblast adhesion to fibronectin-coated surfaces. Using this protocol several monoclonal antibodies (P4C2, P3E3, P4G9) were identified that inhibited cultured T lymphocyte but not HT1080 cell adhesion to fibronectin (Table III).

TABLE III

SPECIFIC INHIBITION OF LYMPHOCYTE ADHESION TO PLASMA FIBRONECTIN BY MONOCLONAL ANTIBODIES P3E3, P4C2 AND PPG49

| Cells | Fibronectin Adhesion (% Control) | | | | |
|---|---|---|---|---|---|
| | SP2 | P1D6 ($\alpha_5\beta_1$) | P3E3 | P4C2 | P4G9 |
| PBL | 100% | 43% | 38% | 10% | 52% |
| Jurkat | 100% | 22% | 33% | 12% | 48% |
| Molt 4 | 100% | 18% | 12% | 8% | 39% |
| HT1080 | 100% | 5% | 98% | 93% | 104% |

Immune precipitation from Triton X-100 detergent lysates prepared with $^{125}$I-surface labeled PBL (not shown), Molt 4 or HT1080 (FIG. 2) cells showed that the inhibitory monoclonal antibodies (data shown for P3E3) reacted with a single protein present in lymphocyte extracts that migrated at M 150,000 (p150) in the presence (not shown) or absence (FIG. 2) of reducing agent. Under these immune precipitation conditions p150 lacked an apparent $\alpha$-$\beta$ subunit structure and did not migrate with either the $\alpha$ or $\beta$ subunit of the integrin receptors $\alpha 2\beta 1$ or $\alpha 3\beta 1$ (FIG. 2). The antigen immune precipitated from Triton X-100 detergent extracts prepared with chronically activated CD8+ killer T lymphocytes (LAK) or CTL (not shown) contained, in addition to p150, relatively large quantities of two smaller proteins that migrated at M 80,000 and 70,000 in the presence (not shown) or absence of reducing agent. V8 protease peptide mapping revealed that p80 and p70 were proteolytic fragments of p150 (not shown). These lower molecular weight forms could be immune precipitated from chronically activated T cells even when detergent extracts were prepared in the presence of multiple protease inhibitors (FIG. 2 legend). p80 and p70 were virtually absent from extracts prepared with resting PBL, cultured T (Molt 4, Jurkat) or B cell leukemias and RD cells.

The biochemical characteristics of p150 suggested that it might be related to the VLA 4 antigen described by Hemler (Hemler et al., 1987). This was confirmed by sequential immune precipitation (not shown) with a VLA 4 specific monoclonal antibody, B5-G10. p150 was established as an a subunit of the integrin super family by its association with $\beta 1$ when immune precipitations were carried out after CHAPS detergent (0.3%) solubilization of $^{125}$I surface labeled T lymphocytes in the presence of 1 mM Ca$^{++}$ (FIG. 3). Under these conditions $\alpha 4$ was precipitated as a heterodimer with $\beta 1$. The identity of $\beta 1$ was confirmed by V8 protease peptide mapping (not shown). The $\alpha 4\beta 1$ heterodimer immune precipitated from T lymphocytes with the inhibitory monoclonal antibodies (P3E3, P4C2 and P4G9) was shown to be distinct from the prototype fibronectin receptor, $\alpha 5\beta 1$, immune precipitated with P1D6 by three criteria. 1) The relative quantities of $\alpha 4\beta 1$ and $\alpha 5\beta 1$ present in detergent extracts of T lymphocytes were distinct with higher levels of $\alpha 4\beta 1$ being present (FIG. 3). This was in agreement with the data we obtained using flow cytometry (FIG. 1). 2) In sequential immune precipitation experiments, monoclonal antibodies to $\alpha 4\beta 1$ did not preclear $\alpha 5\beta 1$ (now shown). 3) The V8 protease peptide maps derived from the $\alpha 4$ and $\alpha 5$ subunits precipitated with monoclonal antibodies P3E3 and P1D6 were clearly distinguishable (not shown). Furthermore, under the conditions (0.3% CHAPS and 1 mM CaCl$_2$) used to solubilize the conjugate of $\alpha 4\beta 1$ from Jurkat cells (FIG. 3) another protein of higher molecular weight (p180) also reacted with the monoclonal antibodies or co-precipitated with $\alpha 4\beta 1$. p180 was absent from extracts prepared with P1D6 monoclonal antibody (FIG. 3), non-lymphoid cells or Triton X-100 detergent extracts prepared in the absence of Ca$^{++}$. The relationship of p180 to other integrins is not known. Since $\alpha 4$ could be immune precipitated without $\beta 1$ after solubilization of T cells with Triton X-100 in the absence of Ca$^{++}$ this revealed that the inhibitory monoclonal antibodies recognized epitopes present on the $\alpha 4$ subunit (FIG. 2).

6.2.2. Distribution of $\alpha 4\beta 1$ and $\alpha 5\beta 1$ in Cultured Cells and Tissue As has been previously reported (Hemler, supra), $\alpha 4\beta 1$ was widely distributed on nucleated hematopoietic cells (Table IV).

TABLE IV

DISTRIBUTION OF THE FIBRONECTIN RECEPTORS $\alpha_4\beta_1$ AND $\alpha_5\beta_1$ ON HUMAN CELLS

| Cells | Relative Fluorescence Intensity | |
|---|---|---|
| | $\alpha_4\beta_1$ | $\alpha_5\beta_1$ |
| Hematopoietic Cells | | |
| PBL | +++ | +/− or − |
| LGL (CD3−, CD16+) | +++ | +/− or − |
| Monocytes (CD16+) | ++ | ++ |
| Granulocytes | − | + |
| Platelets | − | + |

TABLE IV-continued

DISTRIBUTION OF THE FIBRONECTIN
RECEPTORS $\alpha_4\beta_1$ AND $\alpha_5\beta_1$ ON HUMAN CELLS

| | Relative Fluorescence Intensity | |
|---|---|---|
| Cells | $\alpha_4\beta_1$ | $\alpha_5\beta_1$ |
| Spleen | +++ | + |
| Tonsil | +++ | + |
| ALL (T or B) | +++ | ++ |
| LGL Leukemia (CD3+, CD4+) | +++ | +/− |
| AML | +++ | ++ |
| BLCL | ++ | + |
| Molt 4 (CD3+, CD4+) | +++ | + |
| Jurkat (CD3+, CD4+) | +++ | ++ |
| YT (CD3−) | ++ | − |
| PHA blasts (CD4+) | ++++ | ++ |
| CTL (CD3+, CD8+) | ++++ | +++ |
| LAK (CD3+, CD8+) | ++++ | +++ |
| HL-60 | ++ | + |
| U937 | ++ | + |
| K562-1 | − | ++ |
| Fibroblasts | | |
| HFF (p5) | + | + |
| HT1080 | + | ++ |
| RD | ++ | + |
| VA13 | + | ++ |
| Epithelial Cells | | |
| OC-1 | − | − |
| OVCAR-4[7] | − | − |
| T47D | − | + |
| QG56 | − | + |

Two-color flow cytometry revealed that all lymphocyte subpopulations derived from spleen, tonsil and peripheral blood expressed abundant $\alpha_4\beta_1$. In addition, peripheral blood monocytes, freshly derived acute lymphocytic (T or B) leukemias, all large granular lymphocytic (LGL) and myelogenous leukemias and cultured T and B lymphocyte cell lines we examined expressed abundant a4b1 (Table IV). Normal human blood platelets and granulocytes were negative for a4b1 (Table IV). Normal human blood platelets and granulocytes were negative for a4b1. In contrast, the only hematopoietic cell populations that expressed $\alpha_5\beta_1$ were activated T cells, platelets, monocytes and granulocytes, acute lymphocytic (T or B) and myelogenous leukemias and cultured K562, HL-60 and U937 cells. Some cultured T (Molt 4 or Jurkat) and B (ST-1) cell lines expressed low levels of $\alpha_5\beta_1$ as detected by P1D6 monoclonal antibody. In some normal individuals, a subpopulation of PBL were positive for P1D6 fluorescence detected by flow cytometry. We are investigating the nature of this subpopulation of PBL which express $\alpha_5\beta_1$. TY cells, a CD3 T cell lymphoma, were completely negative for P1D6 by flow cytometry. These results show that the major fibronectin receptor constitutively expressed by resting T lymphocytes is $\alpha_4\beta_1$ and as we have previously reported (Wayner et al., 1988) expression of $\alpha_5\beta_1$ in T lymphocytes is restricted to leukemic or activated cultured cells. Interestingly, most fibroblast cell lines expressed low levels of $\alpha_4\beta_1$ while large vessel endothelial cells (HUVEs) and cultured epithelial cells were negative for $\alpha_4\beta_1$ by flow cytometry.

In tissue, $\alpha_4\beta_1$ was present in adult spleen, lymph node and tonsil and essentially absent from all other tissues we examined. In addition, the relative quantities of the fibronectin adhesion receptors expressed by cells in specific tissue domains varied dramatically. For example, PBL and lymphocytes in tonsil and cortex and germinal center areas expressed large quantities of $\alpha_4\beta_1$ but virtually no $\alpha_5\beta_1$. $\alpha_4\beta_1$ was also found in epithelial regions in adult lymphatic tissue, but whether this was the result of lymphocyte infiltration of these areas or expression of $\alpha_4\beta_1$ by lymphatic epithelial cells was unclear.

6.2.3. $\alpha_4\beta_1$ Localizes in Fibronectin-Dependent Focal Adhesions

There is a specific reorganization of cell surface adhesion receptors to the focal adhesions when cells are grown on the appropriate ligands in the absence of serum (reviewed by Burridge et al., 1988, Ann. Rev. Cell Biol., 4, 487–525). Since some fibroblasts express $\alpha_4\beta_1$ we investigated whether this receptor would distribute into focal adhesions when fibronectin was used as the adhesion substrate. As can be seen in FIG. 4 (A and C), the primary focal contact sites or focal adhesions could be visualized by interference reflexion microscopy (Izzard, S. C. and Lochner, L. R., 1976, J. Cell. Sci., 21, 129–159) when RD cells were grown in fibronectin. As we and others have reported (Roman, J., LaChance, R., Broekelmann, T. J., Roberts, C. J., Wayner, E. A., Carter, W. G., and Macdonald, J., 1988, J. Cell Biol. 108:2529–2543), in the absence of serum $\alpha_5\beta_1$ was concentrated at the focal adhesions when RD cells were grown on fibronectin (FIG. 4B, arrows) but not laminin-coated surfaces. Likewise, staining with monoclonal antibody P4G9 (FIG. 4D, arrows) revealed that $\alpha_4\beta_1$ was also concentrated in focal adhesions when cells were grown on fibronectin but not laminin-coated surfaces (not shown). These results demonstrate a specific interaction of $\alpha_4\beta_1$ with fibronectin present in focal adhesions, the primary adhesion structure of cultured cells.

The presence of both receptors in focal contacts suggested the possibility that $\alpha_4\beta_1$ and $\alpha_5\beta_1$ bind to distinct adhesion sequences in fibronectin. In fact, evidence for this was obtained when P4C2 and P1D6 were used simultaneously to inhibit cell adhesion to intact plasma fibronectin. P1D6 and P4C2 when used together completely inhibited adhesion of T lymphocytes and partially inhibited adhesion of RD cells to intact plasma fibronectin (Table V).

TABLE V

COMBINED EFFECT OF MONOCLONAL ANTIBODIES
P1D6 AND P4C2 ON T LYMPHOCYTE AND RD
CELL ADHESION TO FIBRONECTIN

| Cells | Antibody | Specificity | Adhesion (% of Control ± SD) |
|---|---|---|---|
| RD | IgG | — | 100% |
| | P1D6 | $\alpha_5\beta_1$ | 81 ± 11 |
| | P4C2 | $\alpha_4\beta_1$ | 99 ± 7 |
| | P1D6 + P4C2 | | 36 ± 8 |
| Jurkat | IGG | — | 100% |
| | P1D6 | $\alpha_5\beta_1$ | 26 ± 9 |
| | P4C2 | $\alpha_4\beta_1$ | 38 ± 14 |
| | P1D6 + P4C2 | | 0 |

Interestingly, unlike T lymphocytes, neither P1D6 nor P4C2 alone were good inhibitors of RD cell adhesion to intact plasma fibronectin. RD cell adhesion to fibronectin could be efficiently inhibited by P1D6 and P4C2 only when used together.

6.2.4. $\alpha_4\beta_1$ Functions as the Receptor for an RGD Independent Alternative Attachment Site in Fibronectin The preceding results (Table III, Table V, FIG. 1, FIG. 4) clearly indicated that attachment of some cells to plasma fibronectin was mediated by two independent cell surface receptors, $\alpha_4\beta_1$ and $\alpha_5\beta_1$. It has been well documented that the ligand for α5β1 in fibronectin is the 80 kDa cell-binding domain which contains the RGD sequence (Pytela, R., Pierschbacher, M. D., and Ruoslahti, E., 1985, Cell, 40:191–198). To determine the region of fibronectin that interacts with α4β1 we examined the adhesion of cultured T lymphocytes to various proteolytic fragments of plasma fibronectin (see FIGS. 5A and B), as well as the effect of monoclonal antibodies P1D6 and P4C2 on lymphocyte adhesion to these fragments. As shown in FIG. 6, Jurkat, YT and Molt 4 cells attach to a 38 kDa fragment containing the Heparin (Hep) II domain much more efficiently than to an RGD-containing fragment (80 kDa). Jurkat and Molt 4 cells also attach in a dose dependent manner to another Hep II domain containing fragment of 58 kDa. Maximum cell attachment to the 58 kDa fragment, however, reached only 30% of that achieved by the 38 kDa fibronectin fragment. This suggests that the 38 kDa fragment contains a high affinity attachment site for T lymphocytes. T lymphocytes did not adhere to the N-terminal 29 kDa fragment containing the Hep I domain of plasma fibronectin. In general, freshly derived PBL showed a similar pattern of attachment as Jurkat or Molt 4 cells and the ability of freshly derived PBL to bind to the 80 kDa fragment correlated with expression of α5β1. Other hematopoietic cell lines such as K562 cells (FIG. 6) exhibited a clear preference for the 80 kDa fragment of plasma fibronectin while RD cells expressed promiscuous adhesion to all the fragments of plasma fibronectin tested except the N-terminal 29 kDa fragment. RGDS (SEQ ID NO: 1) (1 mg/ml) partially inhibited (50%) Jurkat cell adhesion to intact fibronectin and completely (100%) inhibited their adhesion to the 80 kDa fragment. Jurkat cell adhesion to the 38 kDa fragment was unaffected by RGDS (up to 1 mg/ml).

As we have previously shown (Table 3 and FIG. 1), monoclonal antibodies to α4β1 and α5β2 partially inhibited T lymphocyte adhesion to intact plasma fibronectin (FIG. 7, top). As expected, P1D6 completely inhibited adhesion of T cells to the 80 kDa fragment which contains the RGD adhesion sequence (FIG. 7, middle). P1D6 did not inhibit T lymphocyte adhesion to the 38 kDa (FIG. 7, bottom) or 58 kDa fragments. In contrast, P4C2 completely inhibited T lymphocyte adhesion to the 38 kDa fragment and had no effect on adhesion to the 80 kDa fragment (FIG. 7). Furthermore, adhesion of T lymphocytes to the 58 kDa fragment which also contains Hep II could be inhibited by P4C2. In every case other T lymphocyte cell lines which express both α4β1 and α5β1 (such as Jurkat cells) behave exactly as Molt 4 cells (FIG. 7). As seen in Table 4, K562 cells express only α5β1. Adhesion of K562 cells to the 38 (FIG. 6) and 58 kDa fragments was greatly reduced when compared to their adhesion to the 80 kDa fragment (FIG. 6). Adhesion of these cells to intact plasma fibronectin (FIG. 1) or the 80 kDa fragment could be completely inhibited by P1D6. On the other hand, YT cells which do not express α5β1 (Table IV) adhere poorly to intact plasma fibronectin and the 80 kDa fragment (FIG. 6). These cells require 2–3 times longer to adhere to plasma fibronectin-coated surfaces than Jurkat or Molt 4 cells. YT cells, however, adhere efficiently and in a dose dependent manner to the 38 kDa fragment (FIG. 6) and adhesion of these cells to the 38 kDa fragment could be completely inhibited by P4C2. These data indicate a direct correlation between expression of α4β1 and the ability to attach to fragments of plasma fibronectin containing the Hep II and IIICS regions. Furthermore, these data show unequivocally that a4b1 functions as the receptor for this alternative cell adhesion domain.

6.2.5. α4β1 is the Lymphocyte Receptor for CS-1

The IIICS region present on the A chain of plasma fibronectin (FIG. 5) contains at least two sites responsible for mediating cell adhesion to fibronectin (Humphries et al., 1986, J. Cell Biol. 103:2637–2647; Humphries et al.; 1987, J. Biol. Chem. 262:6886–6892; Humphries et al.; 1988, J. Cell Biol. 106:1289–1297). Using a series of overlapping synthetic peptides spanning the entire IIICS region (CS peptides) Humphries and co-workers showed that the CS-1 (N-terminal) peptides contained adhesion sequences recognized by mouse melanoma cells (Humphries et al., 1986, 1987). We have shown here that the 38 kDa fragment contains a high affinity adhesion site recognized by human T lymphocytes and that α4β1 is the receptor which mediates T lymphocyte adhesion to 38 kDa. This fragment does not contain the CS-5 site but it does contain the entire CS-1 region (Garcia-Pardo et al., 1987, Biochem. J., 241:923–928) which was defined as a high affinity adhesion site for melanoma cells (Humphries et al., 1987, J. Biol. Chem. 262:6886–6892). Therefore it was of interest to determine if T lymphocytes would recognize and bind to CS-1 and if α4β1 was the receptor involved in this interaction.

T lymphocytes (Jurkat or Molt 4 cells) recognize and attach to CS-1 (rabbit IgG conjugate)-coated plastic surfaces (Table VI). T lymphocytes (Jurkat) do not attach to CS-2 (rabbit IgG conjugate) coated surfaces or to plastic surfaces coated with rabbit IgG alone. Furthermore, monoclonal antibodies to α4β1 (P4C2) completely inhibited T lymphocyte adhesion to CS-1 while antibodies to α5β1 (P1D6) had absolutely no effect (Table VI). As we have previously shown antibodies to α4β1 completely and specifically inhibited T lymphocyte adhesion to the 38 kDa fragment (Table VI) while antibodies to α5β1 specifically inhibited adhesion to the RGD (SEQ ID NO: 7) containing 80 kDa fragment.

TABLE VI

INHIBITION OF T LYMPHOCYTE ADHESION TO CS-1 PEPTIDE WITH MONOCLONAL ANTIBODIES TO α4β1

| Ligand | IgG | Antibody[1] P4C2 | P1D6 |
|---|---|---|---|
| 80 kDa | 8580 ± 214 | 7154 ± 398 | 202 ± 105 |
| 38 kDa | 22680 ± 1014 | 114 ± 78 | 24917 ± 352 |
| CS-1 | 44339 ± 513 | 841 ± 555 | 42897 ± 728 |
| CS-2 | 2576 + 214 | 535 ± 258 | 435 ± 168 |

6.3. Discussion

Using monoclonal antibody technology (Wayner, E. A., Carter, W. G., Piotrowicz, R. and T. J. Kunicki, 1988, J. Cell Biol., 10: 1881–1891) we have identified a new fibronectin receptor α4β1. Monoclonal antibodies P3E3, P4C2 and P4G9 recognized epitopes on the α4 subunit and completely inhibited the adhesion of peripheral blood and cultured T lymphocytes to a 38 kDa tryptic fragment of plasma fibronectin containing the carboxy terminal Heparin II domain and part of the type III connecting segment (IICS). The ligand in IIICS for α4β1 was the CS-1 region previously defined as an adhesion site for melanoma cells. The functionally defined monoclonal antibodies to α4 partially inhibited T lymphocyte adhesion to intact plasma fibronectin and had no effect on their attachment to an 80 kDa tryptic fragment containing the RGD adhesion sequence. Monoclonal antibodies (P1D6 and P1F8) to the previously described fibronectin receptor, α5β1, completely inhibited T lymphocyte adhesion to the 80 kDa fragment but had no effect on their attachment to the 38 kDa fragment or to CS-1. Both α4β1 and α5β1 localized to focal adhesions when fibroblasts which express these receptors were grown on fibronectin-coated surfaces. These findings demonstrated a specific interaction of both receptors with fibronectin at focal contacts.

Recently, Bernardi et al., 1987, supra; Liao et al., 1987, Exp. Cell, Res., 171:306–320; Liao et al., 1989, Exp. Cell Res., 181:348–361 reported that some B lymphocyte cell lines bind to a region of plasma fibronectin located within the carboxy terminal Hep II domain. Liao et al., 1987, supra identified an integrin-like receptor on B cells. However, it is not clear whether the protein they described was α4β1, α2β1 or α5β1. Bernardi et al., 1987, supra also identified fibronectin receptors expressed by B lymphocytes. Interestingly, in this study, B cells which attached to fragments containing Hep II expressed a receptor similar to α4β1 while cells which attached to the RGD containing cell adhesion domain expressed a receptor similar to α5β1. However, from these data it was also not possible to clearly identify the receptor involved in binding. Together, the results of these previous reports and the present findings provide clear evidence in support of i) the existence of an alternative adhesion domain present in the carboxy terminal region of plasma fibronectin and ii) a role for α4β1 as the receptor for this alternative adhesion site. It will be interesting to determine the precise amino acid sequences responsible for α4β1 interaction with fibronectin. Since neither the 38 or 58 kDa fragments or CS-1 contain an RGD sequence (Kornblihtt et al., 1985, supra; Garcia-Pardo, 1987, supra; Humphries et al., 1986, supra; and Humphries et al., 1987, supra), it is clear that characterization of the ligand for α4β1 will identify a new amino acid sequence important for cell adhesion to fibronectin. Since the 38 kDa fragment does not contain CS-5 (Garcia-Pardo, 1987, supra) the minimal amino acid sequence responsible for T lymphocyte adhesion to 38 kDa and therefore the ligand for α4β1 in these cells is not arg-glu-asp-val or REDV (SEQ ID NO: 19) (Humphries et al., 1986, supra).

Like α2β1, the α4 subunit is weakly associated with the β1 subunit. The data presented here (FIG. 2) and our previous findings (Wayner, E. A. and Carter, W. G., 1987, supra and Wayner et al., 1988, supra) show that the functionally defined monoclonal antibodies to α2β1 and α4β1 selectively interact with epitopes present on the α subunits, based on immune precipitated of α2 or α4 without β1 after subunit dissociation. These results suggest that the unique α subunit is responsible for determining the ligand-binding specificity of each α-β complex. This concept is now further support by the observations presented here that α5 and α4, which are both complexed with β1, mediate adhesion to distinct sites on fibronectin. This is not to suggest that the β subunit is not important in binding, but that the specificity of receptor-ligand interactions is determined by a or a unique α-β complex.

It is interesting that while LAK cells expressed abundant cell surface α4β1 it did not appear to be a functional receptor; P1D6 completely inhibited LAK cell adhesion to fibronectin. The reason for this could be that LAK cells express a degraded form of α4 (see FIG. 2). In addition, because they are activated, LAK cells over express α5β1 when compared to resting peripheral blood or leukemic T cells (Table VIII). In other cells which express larger quantities of α5β1 relative to α4β1 (K562-1 and HT1080) adhesion to the 80 kDa RGD (SEQ ID NO: 7) containing domain via α5β1 is dominant (see K562-1 cells, FIG. 6). This implies that regulation of receptor expression determines the ability of a cell to recognize and bind to different sites on fibronectin. Furthermore, it is also possible that co-expression of the two receptors for fibronectin could increase the avidity of cell binding, for example, Jurkat and RD cells express relatively promiscuous adhesion to fibronectin when compared to YT cells which express only α4β1.

The regulation of cell adhesion of fibronectin is potentially complex even under the simplest possible conditions, which assume that α5β1 and α4β1 function independently of each other and do not overlap during interaction with the two binding sites on fibronectin. Variation from this simple state provides opportunities for exquisitely sensitive regulation of cell adhesion. At the least complex level, this regulation can be roughly categorized as i) processes that control the synthesis and/or exposure of the binding sites on the ligand and (ii) regulation of functional expression of the receptors. Examples of regulation at both levels are currently available and include, the observation that lymphokines and specific antigen induce α5β1 expression on T lymphocytes followed by increased cell adhesion to fibronectin (Wayner et al., 1988, supra). In addition, the control of mRNA splicing in the IIICS region of fibronectin (Kornblihtt et al., 1985, supra) during wound healing or inflammation may dictate the specificity of receptor-ligand binding in resting or activated T cells. Variations from the simple state are intriguing but require additional experimentation to even begin to identify the multitude of potential mechanisms.

In conclusion, these findings show clearly that cultured T lymphocytes use two independent receptors during attachment to fibronectin and that i) α5β1 is the receptor for the RGD containing cell adhesion domain, and ii) α4β1 is the receptor for a carboxy terminal cell adhesion region containing the Heparin II and IIICS domains. Furthermore, these data show that T lymphocytes express a clear preference for a region of molecular heterogeneity in IIICS (CS-1) generated by alternative splicing of fibronectin pre-mRNA and that α4β1 is the receptor for this adhesion site.

7. EXAMPLE

Lymphocyte Adhesion to Activated Endothelium is Mediated by the Binding of the Integrin Receptor α4β1 to CS-1 in the Alternatively Spliced IIICS Region of Fibronectin The following experiments demonstrated the role of the α4β1 receptor and its ligand, CS-1, in mediating T cell adhesion to cultured large vessel endothelial cells and endothelial cells which had been activated with a variety of cytokines associated with the inflammatory response, including IL-1, tumor necrosis factor alpha (TNFα), and tumor necrosis factor beta (TNFβ). In addition, the ability of monoclonal antibodies and peptide fragments to block adherence of lymphocytes to endothelium via the α4β1 receptor was demonstrated.

7.1. Materials and Methods Reagents 7.1.1. Reagents

Reagents used were as described in Section 6.1.1, supra.

7.1.2. Cells and Cell Culture

Jurkat (Human T cell leukemia) was obtained from Dr. Paul Conlon (Immunex. Corp., Seattle, Wash.), Ramos (Human B cell Leukemia) was obtained from the American Type Culture Collection (Rockville, Md.). The LAD (leukocyte adhesion deficient) and ST-1 B cell lines were prepared by Epstein-Barr virus transformation of human B lymphocytes.

The LAD cell line was developed from the B cells of a patient with a deficiency in the β2 integrin family of adhesion receptors and was obtained from Dr. John Harlan (Harborview Medical Center, Seattle, Wash.). Human umbilical vein endothelial cells (HUVEs) were purchased from Cell Systems, Seattle, Wash. HUVEs were maintained in defined (serum-free) media also purchased from Cell Systems (CS-100 media).

7.1.3. Activation of HUVEs with Inflammatory Cytokines

HUVEs were incubated with IL-1 β (1 ng/ml) or in some experiments with TNF α (10 ng/ml) for 6–24 hours. At the end of this incubation the HUVE monolayers were washed and used in the adhesion assay.

7.1.4. Synthesis of CS Peptides

Peptides derived from the CS-1 region of plasma fibronectin were synthesized and HPLC purified according to standard protocols by Dr. James Blake at the Oncogen Corp., Seattle, Wash. The CS-1 peptide was conjugated to rabbit serum albumin or KLH also according to standard protocols by Dr. James Blake. The RGDS (SEQ ID NO: 1) control peptide was obtained from Peninsula Laboratories (Belmont, Calif.).

7.1.5. Monoclonal Antibodies

The following antibodies were developed in this laboratory: P1H5, which recognizes the α2β1 receptor (Wayner et al., 1987, J. Cell Biol. 105:1873–11884; Wayner et al. 1988, J. Cell Biol. 107:1881–1891); P1B5, which recognizes the α3β1 receptor (supra); P1D6, which recognizes the α5β1 prototype fibronectin receptor described by Pytela et al. (Cell 40: 191–198); P4C10, which recognizes the β1 subunit; and P4H9 which recognizes β2 (CD18), using methods described fully in Wayner et al. (1987, J. Cell Biol. 105: 1873–1884) and Wayner et al. 1988, J. Cell Biol. 107: 1881–1891) which are incorporated in their entirety by reference herein, and described in Table II.

7.1.6. Endothelial Cell Adhesion Assay

Human umbilical vein endothelial cells (HUVEs) were cultured in 48 well plates as described (supra). To measure adherence of lymphocytes to HUVE monolayer cultures, lymphocytes were labeled with $Na_2\ ^{51}CrO_4$ (50 μCi/ml) for 2–4 hours), washed, and then $10^5$ lymphocytes were incubated with HUVE monolayers in the presence or absence of inhibitory antibodies or CS-1 derived peptides. The lymphocytes were allowed to adhere for 30 minutes at 37°. Non-adherent cells were subsequently removed by washing with PBS, and the adherent cells were dissolved in SDS/NaOH. Bound $^{51}$Cr-cpm were quantitated in a gamma counter. In some experiments, endothelial cells were activated prior to the adhesion assay by incubating with IL-1 β (1 ng/ml) or TNF-β (10 ng/ml) for 6–24 hours in defined CS-100 media (Cell Systems, Seattle, Wash.).

7.2. Results 7.2.1. Surface Phenotype of Lymphocytes from Normal and Lad Patients In order to establish what mechanism lymphocytes use during extravasation we first determined the surface phenotype of normal and LAD lymphocytes with respect to the integrin receptors. These data are in Table VII and show clearly that the LAD cells possess a normal cell surface phenotype with respect to the β1 containing integrins. Since, as expected, the B cells derived from the patient with LAD were negative for β2, this strongly suggests that LAD lymphocytes use the β1 containing integrins during their adhesion to and passage through the endothelium.

TABLE VII

FLUORESCENCE ANALYSIS OF INTEGRIN RECEPTOR EXPRESSION BY NORMAL AND LAD LYMPHOCYTES

| | | Fluorescence Intensity[a] | | | |
|---|---|---|---|---|---|
| Receptor | Antibody | Jurkat (T) | Ramos (B) | ST-1 | LAD |
| $β_2$ | P4H9 | + | + | ++ | − |
| $β_1$ | P4C10 | +++ | ++ | + | + |
| $α_2$ | P1H5 | ++ | + | ++ | + |
| $α_3$ | P1B5 | − | − | − | − |
| $α_4$ | P4G9 | +++ | ++ | ++ | ++ |
| $α_5$ | P1D6 | + | +/− | +/− | +/− |

[a]Flurescence intensity was determined on a three decade log scal and is expressed in arbitrary units with each plus indicating 50 units from 0–255 (channel numbers). A plus/minus indicates a definite and reproducible shift above background (<50 units).

TABLE VIII

ADHESION OF T AND B LYMPHOCYTES RESTING AND ACTIVATED HUVE MONOLAYERS

| | Adhesion (cpm)[b] | |
|---|---|---|
| Cell Line | Basal | IL-1β |
| LAD (B) | 29360 | 94580 |
| ST-1 (B) | 11572 | 143860 |
| Ramos (B) | 1088 | 11168 |
| Jurkat (T) | 74196 | 352028 |
| YT (T) | 43396 | 189384 |

7.2.2. Ability of Lymphocytes to Adhere to Resting and Activated Endothelial Cells Chromium-labeled lymphocytes from various cell lines were tested for their ability to adhere to either resting or activated endothelial cells (Table VII). Although all the cell lines tested were found to adhere to some extent to resting endothelium, adhesion of T and B lymphocytes to endothelium activated by either IL-1 or TNF was observed to be much greater, by a factor of as much as ten-fold. Adhesion of lymphocytes from LAD patients to endothelium was not found to be significantly different from that observed for ST-1 cell lines derived from normal B cells (ST-1). There was no difference observed among cell lines between adhesion to IL-1 versus TNF activated endothelium.

7.2.3. Effects of Anti-Receptor Antibodies on Lymphocyte Adherence to Endothelium When the ability of chromium-labeled lymphocytes to adhere to endothelium was tested in the presence of hybridoma supernatants, only monoclonal antibodies directed toward $α_4β_1$ or β1 were found to inhibit adhesion; monoclonal antibodies directed toward other receptors such as the prototype fibronectin receptor and the α3β1 receptor were found to have virtually no inhibitory effect (Table 8). In the presence of monoclonal antibodies P4C2 (directed toward $α_4β_1$) and P4C10 (directed toward β1), adhesion of labeled lymphocytes to endothelium was completely abrogated. Interestingly, adhesion of LAD cell adhesion was also inhibited by anti-$α_4β_1$ antibody [P4C2], indicating that the CD18 receptor is not involved in the observed adherence properties. In addition, although α2β1, α5β1 (Table VIII) and β2 (not shown) are expressed by lymphocytes, antibodies to these receptors did not inhibit lymphocyte adhesion to either basal or activated HUVEs (see Table IX). These data show that surface expression of an integrin receptor and binding of an inhibitory antibody to it does not necessarily lead to inhibition of lymphocyte binding to endothelium. This implies a specific role for α4β1 in mediating lymphocyte adhesion to the endothelium as the first step in extravasation. Furthermore, since the antibodies against α4β1 inhibited lymphocyte adhesion to endothelial cells this suggested that the ligand for α4β1, the amino acid sequence EILDVPST (SEQ ID NO: 6) (see Table XII) might also be involved in lymphocyte diapedesis via binding of α4β1 to this sequence present in a ligand expressed on the surface of the endothelium.

TABLE IX

EFFECT OF INHIBITORY MONOCLONAL ANTIBODIES ON LYMPHOCYTE ADHESION TO HUVE MONOLAYERS (IL-1β ACTIVATED)

| Cell Line | Antibody | Specificity | Adhesion (cpm) | |
|---|---|---|---|---|
| | | | Basal | +IL-1β |
| LAD (B) | SP2 | — | 19542 | 104672 |
| | P1D6 | α$_5$β$_1$ | 15688 | 113696 |
| | P1B5 | α$_2$β$_1$ | 19064 | 90912 |
| | P4C2 | α$_4$β$_1$ | 6458 | 38132 |
| | P4C10 | β$_1$ | 6360 | 52552 |
| Ramos (B) | SP2 | — | 972 | 12157 |
| | P1D6 | α$_5$β$_1$ | 808 | 11196 |
| | P1B5 | α$_2$β$_1$ | 124 | 10028 |
| | P4C2 | α$_4$β$_1$ | 456 | 3688 |
| | P4C10 | β$_1$ | 604 | 3152 |
| Jurkat (T) | SP2 | — | 83924 | 372159 |
| | P1D6 | α$_5$β$_1$ | 83956 | 417588 |
| | P1B5 | α$_2$β$_1$ | 66580 | 489952 |
| | P4C2 | α$_4$β$_1$ | 23108 | 136632 |
| | P4C10 | β$_1$ | 36892 | 230416 |

7.2.4. The Role of CS-1 as Ligand to α$_4$β$_1$ in Lymphocyte Adhesion to Endothelium The ability of synthetic CS-1 and derivative peptides to inhibit adherence of chromium-labeled lymphocytes to activated endothelial cells was evaluated using various peptides. The synthetic CS-1 peptide was a strong inhibitor of T or B lymphocyte adhesion to basal or activated endothelial cell monolayers (Tables X and XI). Interestingly, the EILDVPST (SEQ ID NO: 6) sequence was the minimal peptide also required to inhibit lymphocyte adhesion to resting or activated HUVEs (Tables X and XI). In some cases, such as with the Ramos B cell line, adhesion of these cells to HUVEs could be completely abrogated with the EILDVPST peptide. In control experiments (Table XI), the RGDS (SEQ ID NO: 1) sequence which is the ligand for the prototype fibronectin receptor, α$_5$β$_1$, did not inhibit lymphocyte adhesion to resting or activated HUVEs.

TABLE X

EFFECT OF CS-1 AND CS-1 DERIVED PEPTIDES ON LYMPHOCYTE ADHESION TO HUVE's

| Cell Line | Peptide # | Sequence | Adhesion (cpm) | |
|---|---|---|---|---|
| | | | Basal | +IL-1β |
| LAD (B) | 293A | Unrelated | 20856 | 74096 |
| | 344 | CS-1 | 17500 | 26172 |
| | 350 | VpST | ND$^c$ | 42728 |
| | 352 | EILDVPST | ND | 29484 |
| | 354 | GPEILDVPST (SEQ ID NO:11) | ND | 27219 |
| Ramos (B) | 293A | Unrelated | 4856 | 11132 |
| | 344 | CS-1 | 1660 | 2828 |
| | 350 | VPST | ND | 4568 |
| | 352 | EILDVPST | ND | 2584 |
| | 354 | GPEILDVPST | ND | 2265 |

TABLE X-continued

EFFECT OF CS-1 AND CS-1 DERIVED PEPTIDES ON LYMPHOCYTE ADHESION TO HUVE's

| Cell Line | Peptide # | Sequence | Adhesion (cpm) | |
|---|---|---|---|---|
| | | | Basal | +IL-1β |
| Jurkat (T) | 293(A) | Unrelated | 58084 | 129864 |
| | 344 | CS-1 | 29568 | 75772 |
| | 350 | VPST | ND | 127544 |
| | 352 | EILDVPST | ND | 93056 |
| | 354 | GPEILDVPST | ND | 89721 |

TABLE XI

EFFECT OF CS-1 AND CS-1 DERIVED PEPTIDES OR RGDS ON LYMPHOCYTE ADHESION TO HUVE's

| Cell Line | Peptide # | Sequence | Adhesion (cpm) | |
|---|---|---|---|---|
| | | | Basal | +IL-1β |
| Jurkat (T) | — | — | 161092 | 314848 |
| | — | RGDS | 298688 | 357616 |
| | 344 | CS-1 | 82404 | 248976 |
| | 350 | VPST | 203716 | 322208 |
| | 351 | LDVPST | 166948 | 326260 |
| | 352 | EILDVPST | 84456 | 234796 |
| LAD (B) | — | — | 44860 | 71408 |
| | — | RGDS | 70652 | 102076 |
| | 344 | CS-1 | 22976 | 51560 |
| | 350 | VPST (SEQ ID NO:12) | 38176 | 98860 |
| | 351 | LDVPST (SEQ ID NO:13) | 39700 | 92792 |
| | 352 | EILDVPST | 29964 | 58784 |
| Ramos (B) | — | — | 2724 | 12936 |
| | — | RGDS | 16920 | 28104 |
| | 344 | CS-1 | 1844 | 5160 |
| | 350 | VPST | 4168 | 15320 |
| | 351 | LDVPST | 3532 | 15092 |
| | 352 | EILDVPST | 1696 | 4964 |

TABLE XII

INHIBITION OF LYMPHOCYTE ADHESION TO FIBRONECTIN WITH PEPTIDES DERIVED FROM CS-1-B12

| Peptide | Sequence | Inhibition |
|---|---|---|
| CS-1 | | +++ |
| A13 | DELPQLVTLPHPN (SEQ ID NO:14) | − |
| B13 | LHGPEILDVPST (SEQ ID NO:15) | +++ |
| 350 | VPST | − |
| 351 | LDVPST | − |
| 352 | EILDVPST | +++ |
| 354 | GPEILDVPST | +++ |

7.3. Discussion

Experimental observations (see Section 6, supra) strongly suggested that the high affinity binding site for T lymphocytes in plasma fibronectin was located in the CS-1 region of the IIICS domain. The CS-1 region is comprised of 25 amino acids DELPQLVTLPJPNLHGPEILDVPSTVQK-TPFVTHPGYDTGNGIQLP (SEQ ID NO:20) (FIG. 9). Therefore, it was important to determine the minimal peptide sequence responsible for the binding of the lymphocyte α$_4$β$_1$ receptor to fibronectin. The initial step we took was to divide the CS-1 peptide into two smaller peptides, A13 and B12 (FIG. 9) and to examine whether either of these peptides could compete with fibronectin for binding to the $\alpha_4\beta_1$ receptor and therefore inhibit lymphocyte adhesion to fibronectin. The data clearly indicate that the inhibitory activity resides in the B12 peptide derived from the carboxy terminal portion of CS-1. The next step we took was to investigate the ability of increasingly longer peptides derived from the carboxy terminal portion of B12 to inhibit lymphocyte adhesion to fibronectin and CS-1 (RSA conjugate) coated-surfaces. These data show that with regard to adhesion of lymphocytes to plasma fibronectin and CS-1 the minimal amino acid sequence required for binding of $\alpha_4\beta_1$ is EILDVPST (SEQ ID NO: 6).

Polymorphonucleated leukocytes (neutrophils) from patients with leukocyte adhesion deficiency (LAD) have a defect in expression of the β2 integrin subunit and therefore cannot use the β2 containing receptors (LFA-1, Mac-1 or p 150/95) in their adhesion to the vascular endothelium. Neutrophils from these patients therefore, do not leave the blood stream to pass into peripheral tissues. LAD lymphocytes, however, do undergo diapedesis to pass through the endothelium and can be found in tissues derived from patients with this disorder. This, therefore, implies that lymphocytes use a mechanism distinct from the β2 containing integrins during their passage from the blood stream into the peripheral tissues. The following series of experiments comprises our attempts to fully understand the mechanisms utilized by peripheral blood lymphocytes during diapedesis.

The experiments described supra have clearly shown the important role played by the $\alpha_4\beta_1$, receptor in the adhesion of lymphocytes to vascular endothelial cells.

All lymphocyte cell lines tested were shown to express $\alpha_4\beta_1$ and/or $\alpha_5\beta_1$ by fluorescence analysis, and were observed to adhere to cultured human umbilical vein endothelial cells. This adhesion was found to be blocked only by monoclonal antibodies directed toward $\alpha_4\beta_1$; antibodies directed toward other receptors were not found to have essentially any inhibitory effect, revealing the importance of the $\alpha_4\beta_1$ receptor in the adhesive interaction between lymphocytes and endothelium.

In addition, synthetic CS-1 and derivative peptides (Tables 9, 10, and 11) were found to inhibit adhesion of lymphocytes to endothelium. The amino acid sequence EILDVPST (SEQ ID NO: 6) was found to be particularly important for the interaction. It must be emphasized that it has not been determined whether the lymphocyte $\alpha_4\beta_1$ receptor is, in fact, interacting with fibronectin on the endothelial cell surface. It is also possible that $\alpha_4\beta_1$ is recognizing the peptide EILDVPST or a similar sequence, in the context of another, non-fibronectin protein.

8. EXAMPLE

Activation Dependent Recognition by Hematopoietic Cells of the LDV Sequence in the V Region of Fibronectin "Minimal peptide" and "minimal peptide ligand" are used herein interchangeably to mean a peptide of about 2 to about 12 amino acids in length, especially about 3 to about 8 amino acids in length, and most preferably about 3 to about 5 amino acids in length, wherein the peptide is either a) capable of inhibiting stable cell adhesion of one cell via a β1-containing integrin receptor either to another cell or to a substrate containing an LDV (SEQ ID NO: 3) amino acid sequence; or, b) capable of supporting stable cell adhesion to the substrate through the receptor when the peptide is coupled to a suitable carrier (e.g., rabbit serum albumin, RSA, or a liposome or antibody). Representative minimal peptides are provided by LDV (SEQ ID NO: 3), EILDV (SEQ ID NO: 14), LDVPST (SEQ ID NO: 11); GPEILDVPST (SEQ ID NO: 9), and LHGPEILDVPST (SEQ ID NO: 13), although those skilled in the art will recognize that various routine chemical modifications can be made (e.g., methylation, acylation, acetylation, sulfation, and the like) that will increase (or decrease) the binding affinity of the minimal peptide for the disclosed integrin receptors. Antibodies to these functionally different receptors can be readily raised, screened and selected pursuant to this disclosure.

"Substrate," "surface coated with an LDV minimal peptide," "LDV-coated surfaces," and "coated styrene substrates" are used herein interchangeably to refer to minimal peptide ligands capable of binding to a β1-containing integrin receptor on a cell surface such that the cell becomes stably adherent to the surface substrate. Representative examples of surface substrates include LDVPST-RSA, EILDVPST-RSA, EILDV-RSA, LDV-RSA, and protein substrates synthesized by cells (e.g., endothelial cells) that contain the LDV minimal peptide sequence.

8.1. Background

8.1.1. Cell Populations with Receptors for Adhesion Sequences

Various cell populations can interact with adhesion sequences in the carboxy terminal cell binding domain (CTCBD) of fibronectin (McCarthy et al., 1986, J. Cell Biol. 102: 179–188; Bernardi et al., 1987, J.C. Biol. 105: 489–498; Humphries et al., 1986, J. Cell Biol. 103: 2637–2647; Humphries et al., 1987, J. Biol. Chem. 262: 6886–6892; Liao et al., 1989, Exp. Cell. Res. 171: 306–320; Mould et al., 1990, J. Biol. Chem. 265: 4020–4024; Wayner et al., 1989, J. Cell. Biol. 109: 1321–1330; Garcia-Pardo et al., 1990, J. Immunol. 144: 3361–3366; Guan and Hynes, 1990, Cell 60: 53–61), in addition to the arg-gly-asp-ser (RGDS) adhesion sequence located in the central cell binding domain (CCBD) of fibronectin (Pierschbacher and Ruoslahti, 1983, Nature 309: 30–33). Lymphocytes in particular, bind with high affinity to a 38 kDa chymotryptic fragment of fibronectin (Garcia-Pardo et al., 1987, Biochem. J. 241: 923–928; Garcia-Pardo, 1990, supra; Wayner et al. 1989, supra) which contains the Heparin 2 (Hep 2) domain and 67 (out of 120) amino acid residues of the alternatively spliced type III connecting segment or V (for variable) region (Schwarzbauer et al., 1983, Cell 35: 421–431; Schwarzbauer et al., 1985, Proc. Natl. Acad. Sci. (USA) 82: 1424–1428; Kornblihtt et al., 1985, EMBO J. 4: 1755–1759; Paul et al., 1986, J. Biol. Chem. 261: 12258–12265). The 67 amino acids of this fragment (Garcia-Pardo et al., 1987, supra) which are derived from alternative splicing of the fibronectin gene, span the CS-1, CS-2 and CS-3 regions defined by Humphries et al. (1986, 1987, supra). Experiments described above (supra) indicated that it was the CS-1 sequence that acted as a high affinity binding site for lymphocytes (Wayner et al., 1989, supra; Garcia-Pardo et al., 1990, supra). Interestingly, in human fibronectin two splice sites exist in V120 cDNA (Kornblihtt et al., 1985, supra; Paul et al., 1986, supra), one at the C-terminal end of CS-1 and another just N-terminal to the CS-5 region. Therefore, the entire CS-1 region can either be present or absent in V+ fibronectins.

8.1.2. Integrin Receptor for CS-1

Monoclonal antibody (Mab) inhibition studies (supra) reported that it was the α4β1 integrin receptor that mediated the binding of lymphocyte α4β1 to CS-1 (described above; Wayner et al., 1989, supra; Garcia-Pardo et al., 1990, supra).

This finding was later confirmed by affinity chromatographic isolation of the α4β1 integrin from hematopoietic and melanoma cell populations on CS-1 SEPHAROS (a beaded agarose matrix) (Mould et al., 1990, supra; Guan and Hynes, 1990, supra). It has been reported that certain melanoma cells may bind the LDV (SEQ ID NO: 3) sequence located in the C-terminal portion of CS-1 suggesting that LDV may be a peptide ligand for certain α4β1 receptors (Mould et al., 1991, J. Biol. Chem. 266: 3579–3585). Two recent studies have reported that certain hematopoietic cells may interact with LDV-containing peptides derived from the C-terminal portion of CS-1 (Garcia-Pardo et al., 1990, supra; Guan and Hynes, 1990, supra). However, this invention has identified the minimal sequence in CS-1 capable of promoting stable hematopoietic cell adhesion.

8.1.3. The Minimal Peptide Ligand

In the experiments described herein, the minimal peptide ligand in CS-1 that is capable of supporting stable hematopoietic cell adhesion via α4β1 has been identified. Surprisingly, this ligand varied according to the cell population examined. Although the minimal peptide for melanoma cell adhesion was leu-asp-val (or LDV), many hematopoietic cell lines required larger portions of the C-terminal end of CS-1, while still other populations could be identified that required the entire length of CS-1 to form stable attachments. This suggests that the LDV sequence may be recognized by some cell populations only in the context of intact CS-1 and that the recognition may be regulated in a cell-type specific manner. Further studies herein reveal that LDV recognition is determined by the avidity of the α4β1 complex expressed by an individual cell population. A low avidity receptor, expressed on Jurkat, Ramos, U937 or PHA activated T cells, does not bind LDV minimal peptides but does bind LDV in the context of CS-1. A high avidity receptor, expressed by HUT 78 or A375 melanoma cells, binds LDV-peptide coated surfaces. The avidity of the low avidity α4β1 receptor complex is altered by a monoclonal antibody (Mab) to β1, 8A2. 8A2 was selected for its ability to promote α4β1 dependent binding to fibronectin (Kovach, N. L., and J. M. Harlan, personal communication). Other anti-β1 antibodies suitable for increasing the avidity of a low avidity α4β1 receptor complex include 4B4 (commercially available through Coulter Immunologics), and certain other antibodies to β1 described by Springer (supra) and by others. Suitability of a particular antibody for increasing the avidity of a low avidity α4β1 receptor complex can be determined empirically by coating a surface with an LDV minimal peptide (e.g., an LDVPST-protein conjugate) and testing for the ability of the antibody to β1 to increase the adherence of a suitable test cell (e.g., Jurkat, Ramos, a T lymphocyte PHA blast cell and the like) to the coated surface. Antibodies to β1 that are not suitable for increasing avidity will either block binding of the test cell to the coated surface, or have no effect. Surface expression of α4β1 on cells treated with 8A2 remained unchanged (herein, see below). Therefore, in the presence of Mab 8A2 certain hematopoietic cells (e.g., Jurkat) could be induced to form stable attachments to LDV-coated surfaces. This suggests that recognition of the LDV (SEQ ID NO: 3) sequence in CS-1 may require a change in the α4β1 receptor complex that involves β1. Finally, PHA-stimulated, but not resting T cells, could be induced by Mab 8A2 to bind LDV, suggesting that resting T cells require an additional signal(s) for LDV recognition.

8.1.4. Regulation

Together, the data herein strongly suggests that hematopoetic cell interactions with the carboxy terminal cell binding domain (CTCBD) of fibronectin may be regulated at least at the levels of: 1) α4β1 expression; or, 2) activation of α4β1; or, 3) the expression of the LDV minimal peptide in the CS-1 sequence of V+ fibronectin isoforms. The data presented herein also suggests that multiple signals may be required for T lymphocyte activation and LDV recognition.

8.2. Identification and Characterization of the Minimal CS-1 Sequence 8.2.1. Materials and Methods 8.2.1.1. Materials.

Fibronectin was purified from human plasma as previously described (Wayner and Carter, 1987, J. Cell Biol. 105: 1873–1884). Fragments of fibronectin were the same as previously described (Wayner et al., 1989, supra; Garcia-Pardo et al., 1987, supra). $^{51}$Cr-Sodium chromate was from New England Nuclear (Boston, Mass.). Rabbit serum albumin (RSA), bovine serum albumin (BSA) and Protein A-agarose were from Sigma Chemical Co. (St. Louis, Mo.). Protein G-agarose is commercially available (Pharmacia, La Jolla, Calif.).

8.2.1.2. Peptides and Peptide Conjugates.

A series of peptides spanning the entire CS-1 region were synthesized by using an Applied Biosystems 430A peptide synthesizer and were a generous gift from the Bristol Myers Squibb Pharmaceutical Research Institute, Oncogen Division (Seattle, Wash.). Peptides are routinely synthesized by those skilled in the art and can be purchased from contract manufacturers (e.g., Penninsula Laboratories, Inc., Burlingame, Calif.). Synthetic peptides were HPLC-purified and tested for direct toxicity and growth inhibitory activity. Some peptides were synthesized with an N-terminal cysteine at the end of a gly-gly-gly tail and were chemically conjugated to SMCC-derivatized rabbit serum albumin (RSA) for use in cellular adhesion assays. None of the peptides, either inhibitory or non-inhibitory (or any of the peptide conjugates), were toxic or growth inhibitory.

8.2.1.3. Cells and Cell Culture.

The A375 (human melanoma) and the Jurkat (human T lymphoblastoid) cell lines are widely available (e.g., Jurkat cell line ATCC-CRL8163; A375 CRL 1619; American Type Culture Collection, Rockville, Md.). The HT1080, RD, Ramos, HSB-2 and HUT 78 cells were obtained from the American Type Culture Collection (Rockville, Md.). All cell culture conditions were as previously described (Wayner and Carter, 1987, supra). PHA stimulated T cell blasts were prepared as described from normal fresh human blood (Wayner et al., 1989, supra).

8.2.1.4. Monoclonal Antibodies.

Monoclonal antibodies (Mabs) to adhesion receptors were produced and characterized as described (Wayner and Carter, 1987, supra; Wayner et al., 1988, J. Cell Biol. 107: 1881–1891; Wayner et al., 1989, supra; Kovach, N. L., and J. M. Harlan, personal communication). The 8A2 Mab has been shown to recognize an epitope in the integrin β1 subunit (Kovach, N. L. and J. M. Harlan, personal communication). Anti-β1, PAC10 that blocks cell adhesion is described herein (above), and in Wayner 1989, (supra). The anti-α4 Mab P4C2 has been previously described (Wayner et al., 1989, supra). Control antibody consisted of Protein G purified non-immune mouse IgG.

8.2.1.5. Activation of β1 with Mab 8A2.

The β1 subunit was activated with Mab 8A2 in several ways. In some experiments, cell adhesion assays were carried out in the presence of 8A2. In other experiments, cells were pre-treated with 8A2 Mab for 30 min, washed and then used in cell adhesion assays. The effects of 8A2 Mab could be measured with 10 min with as little as 0.1 ug/ml 8A2 being able to stimulate increased avidity of a low avidity α4β1 receptor complex for fibronectin, CS-1, or LDV minimal peptides.

8.2.1.6. Inhibition of Cell Adhesion to Intact Fibronectin, Fibronectin Fragments and CS-1 Peptide-RSA Conjugates with Mabs.

Antibodies that could alter adhesion of test cells to fibronectin, fibronectin fragments or CS-1 peptide RSA conjugates were identified as previously described (Wayner and Carter, 1987, supra; Wayner et al., 1989, supra). Briefly, a 48 well virgin styrene plate (Costar #3547) was coated with 5 ug/ml plasma fibronectin, fragment or peptide conjugate (with the final concentration of peptide being 5 ug/ml). $Na_2\ ^{51}CrO_4$-labeled cells were incubated with monoclonal antibodies to adhesion receptors for 15 min at room temperature and were then allowed to attach to the coated styrene substrates in the presence of the test antibodies for 30–60 min at 37° C. In some cases test antibodies to adhesive ligands were pre-incubated with the substrates for 15 min before the test cells were added. At the end of the incubation, non-adherent test cells were removed by washing with PBS, and the adherent test cells were dissolved in 0.1N NaOH/0.25% SDS and bound $^{51}Cr$ counts per minute (cpm) were quantitated in a gamma counter.

8.2.1.7. Inhibition of Cell Adhesion to Fibronectin with CS-1 Derived Peptides.

For peptide inhibition studies, $^{51}Cr$-labeled test cells were pre-incubated with CS-1 derived peptides at various concentrations for 15 min at room temperature. The test cells were then allowed to attach to fibronectin-coated surfaces in the presence of exogenous test peptides for 30–60 min. The assay then proceeded as described above.

8.2.2. Results 8.2.2.1. α4β1 is the Receptor for the CS-1 Sequence Located in the Carboxy Terminal Cell Binding Domain of Fibronectin.

The inventor and others have previously reported that antibodies specific for epitopes on the α4 subunit of the α4β1 receptor complex inhibit T or B lymphocyte adhesion to plasma fibronectin, fragments of fibronectin containing adhesion sites in the Hep 2 domain, and fragment containing the first 25 amino acids (CS-1) or V (for variable) region (Wayner et al., 1989, supra; Garcia-Pardo et al., 1990, supra; Guan and Hynes, 1990, supra). Other workers have reported that the receptor complex containing α4 with β1 can be affinity purified on immobilized CS-1 (Mould et al., 1990, supra; Guan and Hynes, 1990, supra) confirming that the cellular receptor for CS-1 is α4β1. However, the contribution of β1 in mediating adhesion to fragments of fibronectin containing Hep 2 (58 kDa derived from the B chain of plasma fibronectin) or the high affinity CTCBD (38 kDa derived from the A chain of fibronectin and contains Hep 2 and CS-1) has not yet been elucidated. Therefore, the inventor examined the adhesion of T (Jurkat, FIG. 1) or B lymphoblastoid cell lines to surfaces coated with various fragments of fibronectin; in the presence of Mabs to inhibitory epitopes on α4 or β1. The data in FIG. 10 show that Jurkat cell adhesion to plasma fibronectin, CS-1 (SEQ ID NO: 15), or fragments of fibronectin containing Hep 2 (58 kDa) and the entire CTCBD fragment (38 kDa) can be inhibited by Mabs to α4 (P4C2) or β1 (P4C10). This confirms the role of β1 in mediating adhesion of cells to the Hep 2 site as well as to CS-1. As disclosed herein (above), adhesion to the CCBD (80 kDa fragment) that contains the RGDS (SEQ ID NO: 1) sequence is inhibited by Mabs directed to α5 (P1D6) or β1 (P4C10).

8.2.2.2. Identification of the Minimal Peptide Ligand for the Lymphocyte α4β1 Receptor in CS-1.

The first step taken to define a minimal peptide ligand in CS-1 for the α4β1 integrin receptor was to divide CS-1 into two smaller peptides, an N-terminal (A13) (SEQ ID NO: 15) and a C-terminal (B12) (SEQ ID NO: 13) peptide. The ability of these (and smaller) peptides to inhibit Jurkat cell adhesion to substrates coated with intact fibronectin was examined (Table XIII). As disclosed herein (supra), and by others (Humphries et al., 1986 and 1987, supra; Garcia-Pardo et al., 1990, supra; Guan and Hynes, 1990, supra) CS-1 is a potent inhibitor of cell adhesion to fibronectin (Table I). Interestingly, only the carboxy terminal B12 peptide is relatively effective in inhibiting T cell adhesion to intact fibronectin (Table XIII).

For these experiments in Table XIII $^{51}Cr$-labeled Jurkat cells ($10^5$/well) were incubated in the presence of the varying concentrations (starting at 2 mg/ml) of the indicated peptides for 15 min. The Jurkat cells were then allowed to adhere to plasma fibronectin-coated surfaces (5 ug/ml) in the presence of the peptides for 30 min. Adhesion to fibronectin was graphically depicted as cpm bound to the fibronectin surface (Y axis), plotted as a function of molar peptide concentration (X axis). The 50% inhibition point was determined from the plotted data for each peptide and the results are presented in Table XIII.

TABLE XIII

MOLAR CONCENTRATION OF CS-1 PEPTIDES REQUIRED FOR 50% INHIBITION OF JURKAT CELL ADHESION TO PLASMA FIBRONECTIN

| Peptide | Sequence | Molar Concentration (mM) |
|---|---|---|
| CS-1 | DELPQLVTLPHPNLHGPEILDVPST (SEQ ID NO:17) | 0.18 |
| B12 | LHGPEILDVPST | 0.40 |
| | GPEILDVPST | 0.45 |
| | EILDVPST | 0.55 |
| | LDVPST | >1.60 |
| | VPST | >2.50 |
| | EILDV | 0.66 |
| | LDV | >2.70 |
| A13 | DELPQLVTLPHPN | >1.00 |

The findings in Table XIII with CS-1, B12, and A13 are consistent with studies by others with human B lymphocytes (Garcia-Pardo et al., 1990, supra) as well as the findings in another report where GPEILDVPST (SEQ ID NO: 9) was reported to be an active peptide for murine hematopoietic cell adhesion (Guan and Hynes, 1990, supra). Next, a series of smaller peptides derived from B12 (SEQ ID NO: 13) were tested for their ability to inhibit Jurkat cell adhesion to intact fibronectin (Table XIII). The results show clearly that deletion of the N-terminal LHGP (SEQ ID NO: 18) or C-terminal PST (SEQ ID NO: 19) residues had little effect on the ability of a particular B12 derived peptide to inhibit Jurkat adhesion to fibronectin. In fact, several of these truncated B12 peptides (Table XIII) were similar in their ability to inhibit T cell fibronectin interaction as long as the minimal EILDV (SEQ ID NO: 14) sequence was present (Table XIII). Interestingly, although LDV (SEQ ID NO: 3) has been reported to be the minimal peptide for the melanoma α4β1 receptor (Mould et al., 1991, supra; Komoriya et al., 1991, J. Biol. Chem. 266: 15075–15079), LDV was not as effective as B12 in inhibiting Jurkat-fibronectin adhesion. The data in Table XIII suggest that the minimal peptide ligand in CS-1 for the T lymphocyte α4β1 receptor is glu-iso-leuasp-val or EILDV. Identical results were obtained with a B lymphoblastoid cell line, Ramos and an identical pattern was observed for peptide inhibition of Jurkat or Ramos cell adhesion to CS-1-coated surfaces; deletion of the N-terminal glutamic acid and isoleucine residues resulted in a peptide with no inhibitory activity.

8.2.2.3. CS-1 Minimal LDV Peptides Support Stable Cell Adhesion and Spreading.

It was of interest to determine if CS-1 or derivative peptides were capable of inducing stable hematopoietic cell adhesion and spreading. Therefore, peptide-conjugates were prepared using rabbit serum albumin (rsa) as a carrier and the conjugates were tested for their ability to support cell adhesion. The relative avidity of binding was examined and compared to intact fibronectin and CTCBD fragments of fibronectin (Table XIV and FIGS. 11 and 12). The adhesion experiments presented in Table XIV were conducted as follows:

$^{51}$Cr-labeled Jurkat cells (105/well) were incubated on surfaces coated with varying concentrations of peptide-rsa conjugates starting at 50 ug/ml (w/v) fragment or peptide (based on peptide not peptide-conjugate weight). Adhesion was evaluated by plotting cpm bound to the surfaces (Y axis), as a function of fragment or peptide concentration (X axis) and the molar concentration of a peptide required to support 50% (of total input cpm) adhesion was determined graphically, and the results are presented in Table XIV. (No adhesion=no measurable adhesion above negative controls.)

TABLE XIV

MOLAR CONCENTRATION OF CS-1 PEPTIDE CONJUGATES REQUIRED FOR 50% ADHESION OF JURKAT CELLS

| Peptide or Fragment | Molar Concentration (nM) |
| --- | --- |
| rsa-CS-1 | 115.0 |
| rsa-B12 | 492.0 |
| rsa-EILDVPST | 1007.0 |
| rsa-EILDV | 1129.0 |
| rsa-LDV | >2000.0 |
| rsa-A13 | No Adhesion |

Adhesion of Jurkat T lymphoblastoid cells to plasma fibronectin, fragments of plasma fibronectin, or CS-1-rsa peptide-coated surfaces was tested in the presence of inhibitory anti-integrin monoclonal antibodies (Mabs) as follows (FIG. 10): namely, 51Cr-labeled cells were incubated in the presence of the indicated Mabs (10 ug/ml purified antibody) for 10 min at ambient temperature and then allowed to attach to the protein or peptide coated-surfaces for 30 min (still in the presence of the inhibitory Mabs). Adhesion is expressed as % of control (i.e., a Protein G-purified non-immune mouse IgG). The plasma fibronectin and the plasma fibronectin-fragments used are the same as those described herein (above).

Adhesion of Jurkat (FIG. 11, Panel A) or A375 melanoma cells (FIG. 11, Panel B) to plasma fibronectin (pFN), CS-1 (SEQ ID NO: 15), A13 (SEQ ID NO: 12) or EILDVPST-coated surfaces was tested as follows: Plasma fibronectin (pFN) CS-1, A13 or EILDVPST-rsa conjugates were coated on virgin styrene surfaces (5 ug/ml). The A375 or Jurkat cells were allowed to adhere for 1 hr. Non-adherent cells were washed off and the resulting monolayers were photographed with an inverted microscope; using phase contrast. These photomicrographs show that A375 cells spread on the surfaces coated with LDV-containing peptides. Evidence for spreading of Jurkat cells can also be seen with surfaces coated with CS-1 (FIG. 12A, top right).

Adhesion of various hematopoetic cell lines to CS-1 (open bars; FIG. 12) or LDV minimal peptide-coated surfaces (cross-hatched bars; FIG. 12) was tested as follows: Jurkat (T lymphoblastoid), A375 (melanoma), U937 (monocytic), Ramos (B lymphoblastoid), and ST-1 (EBV transformed B lymphoblastoid) cells were allowed to adhere to CS-1-rsa or LDVPST-rsa (5 ug/ml peptide) coated surfaces for 30 min at 37° C. At the end of this time the non-adherent cells were washed off and the adherent cells were solubilized in NaOH/SDS and quantitated in a gamma counter. The results are expressed as bound counts per minute.

As expected CS-1 and a peptide containing EILDV were able to support the adhesion of Jurkat and A375 melanoma cells (FIG. 11, Panel A and Panel B). Interestingly, peptide conjugates containing EILDV (FIG. 11, Panel B) or LDV also supported melanoma cell spreading. However, on a molar basis there were significant differences in the ability of CS-1 versus CS-1 derivative peptides to promote Jurkat cell adhesion (Table XIV). In general, truncated CS-1 peptides were inefficient mediators of hematopoietic cell adhesion and none of the truncated CS-1 peptide conjugates could support the adhesion of PHA activated T cell blasts. The minimal peptide sequence required to support melanoma cell adhesion has been reported to be LDV (SEQ ID NO: 3) (Mould et al., 1991, supra; Komoriya et al., 1991, supra). The results presented in FIG. 12 show that A375 melanoma cells adhered to LDVPST-coated surfaces, and of the hematopoietic cell lines tested only Jurkat cells adhered, and then only slightly, to surfaces coated with the LDVPST-RSA conjugate (FIG. 12). Furthermore, some of the hematopoietic cell lines we examined, such as U937 or ST-1 cells adhered relatively poorly to surfaces coated with intact CS-1 (SEQ ID NO: 15) (FIG. 12). The reason for the apparent inability of some cell populations to adhere to CS-1 or LDVPST-coated surfaces was not immediately obvious. Flow cytometry analysis revealed that cell surface expression of α4 or β1 could not account for the functional differences we observed in the ability of a particular cell population to adhere to CS-1 or LDV-coated surfaces. As disclosed herein, supra, U937 (monocytic) and ST-1 (B lymphoblastoid) cells express high levels of cell surface α4 and β1 which are equivalent to the levels expressed by Jurkat and A375 melanoma cells (Wayner et al., 1989, supra). Together, the data in Table XIV and FIG. 12 suggested that CS-1 or LDV minimal-peptide recognition and binding avidity might be regulated in a cell-type specific manner; with melanoma cells possessing the highest affinity/avidity receptor.

8.2.2.4. Activation of the α4β1 Complex Enhances Hematopoietic Cell Recognition of CS-1 Peptides.

The results of the preceding experiments suggested that adhesion of cells to CS-1 might involve the LDV (SEQ ID NO: 3) sequence and that interaction of α4β1 with this sequence outside the context of intact CS-1 may be regulated in a cell-type specific manner. Several reports have suggested that the interaction of cells with ECM proteins (i.e., other than α4β1) may require "activation" of the cells or the integrin receptors (Neugebauer and Reichardt, 1991, Nature 350: 68–71; Shimizu et al., 1990, Nature 345: 250–253). Monoclonal antibody to β1, 8A2, that upregulates α4β1 dependent lymphocyte adhesion to VCAM-1 (Kovach, N. L., and J. M. Harlan, personal communication) was used to examine the effects of activation of the α4β1 receptor complex on adhesion of hematopoietic cells to CS-1 and derivative peptides. These results are shown in FIGS. 13A and 13B (Jurkat); FIGS. 14A and 14B (U937 cells) and FIGS. 15A and 15B (HUT 78).

In a first series of experiments, adhesion of Jurkat cells to surfaces coated with pFN, CS-1 (SEQ ID NO: 15), A13 (SEQ ID NO: 12) or B12 (SEQ ID NO: 13) derived peptide-rsa conjugates was tested in the presence of monoclonal antibody 8A2. The results are shown in FIGS. 13A and 13B. In FIG. 13A adhesion was tested in the presence of purified non-immune mouse IgG (5 ug/ml); and, in FIG. 13B adhesion was tested in the presence of Mab 8A2 (5 ug/ml). These experiments were conducted as follows:

48 well plates were coated with 5 ug/ml (based on peptide weight) peptide-rsa conjugates overnight in PBS at 4° C. $^{51}$Cr-labeled Jurkat cells were allowed to adhere to the peptide-coated surfaces in the presence of IgG or 8A2 for 30 min at 37° C. The rest of the adhesion assay proceeded as for FIG. 12, supra. The results in FIGS. 13A and 13B are expressed as counts per minute extracted from adherent cells.

In a second series of parallel experiments, adhesion of U937 cells to surfaces coated with pFN, CS-1 (SEQ ID NO: 15), A13 (SEQ ID NO: 12) or B12 (SEQ ID NO: 13) derived peptide-rsa conjugates was tested in the presence of monoclonal antibody 8A2. The results are shown in FIGS. 14A and 14B. In FIG. 14A adhesion was tested in the presence of purified non-immune mouse IgG (5 ug/ml); and, in FIG. 14B adhesion was tested in the presence of Mab 8A2 (5 ug/ml). These experiments were conducted as follows: 48 well plates were coated with 5 ug/ml (based on peptide weight) peptide-rsa conjugates overnight in PBS at 4° C. $^{51}$Cr-labeled U937 cells were allowed to adhere to the peptide-coated surfaces in the presence of IgG or 8A2 for 30 min at 37° C. The rest of the adhesion assay proceeded as for FIG. 12, supra. Results are expressed as counts per minute extracted from adherent cells. U937 cells do not adhere to B12 peptides without activation.

In a third series of parallel experiments, adhesion of HUT 78 cells to surface coated with pFN, CS-1, A13 or B12 derived peptide-rsa conjugates was tested in the presence of Mab 8A2. The results are presented in FIGS. 15A and 15B. In FIG. 15A adhesion was tested in the presence of purified non-immune mouse IgG (5 ug/ml); and, in FIG. 15B adhesion was tested in the presence of Mab 8A2 (5 ug/ml). These experiments were conducted as follows: 48 well plates were coated with 5 ug/ml (based on peptide weight) peptide-rsa conjugates overnight in PBS at 4° C. $^{51}$Cr-labeled HUT 78 cells were allowed to adhere to the peptide-coated surfaces in the presence of IgG or 8A2 for 30 min at 37° C. The rest of the adhesion assay proceeded as for FIG. 12. Results are expressed as counts per minute extracted from adherent cells. Unlike U937 cells (above), HUT 78 cells adhere to LDV-coated surfaces without activation.

As can be seen from these combined data, more cells in the Jurkat (FIGS. 13A–B) or U937 (FIGS. 14A–B) cell populations are capable of interacting with CS-1 (SEQ ID NO: 15) and LDV (SEQ ID NO: 3) containing derivative peptides only after activation of the α4β1 receptor complex with the 8A2 monoclonal antibody. Relatively few U937 cells, in fact, appear to adhere to any of the B12 (SEQ ID NO: 13) derived peptides without activation of the α4β1 receptor complex (FIGS. 14A–B). Since pretreatment of cells with 8A2 does not up-regulate expression of either β1 or α4 on U937 cells (supra), these data strongly suggest that recognition of the LDV sequence by α4β1 requires an activation signal which can be transduced through β1. As we have previously shown (Tables XIII and XIV) VPST-rsa conjugates are relatively inactive in inducing stable cell adhesion (FIGS. 13A–B, 14A–B, and 15A–B). These data suggest that the minimal essential adhesion sequence in CS-1 for hematopoietic cells with an activated α4β1 receptor complex is LDV. Interestingly, HUT 78 cells appeared to possess an activated α4β1 receptor complex; resting HUT 78 cells adhered to LDV and this adhesion was not significantly up-regulated by 8A2.

The adhesion of 8A2-activated Jurkat or U937 cells to LDV peptide-coated surfaces could be nearly completely abrogated by inhibitory monoclonal antibodies to α4 (P4C2) or β1 (P4C10) showing clearly that it is the receptor complex of α4 with β1 that is involved in the LDV adhesion (FIG. 16). In these experiments specificity of adhesion of 8A2-activated Jurkat or U937 cells to LDVPST-coated surfaces was tested in the presence of inhibitory monoclonal antibodies to α4 (P4C2) or β1 (P4C10) and the results are shown in FIG. 16. The experiments were conducted as follows: $^{51}$Cr-labeled Jurkat (open bars) or U937 (cross-hatched bars) cells were pre-incubated with 8A2 for 30 min at 37° C. for 30 min. At the end of this time, they were washed free of unbound 8A2, and incubated in the presence of non-immune mouse IgG (10 ug/ml=Control) or inhibitory Mabs to β1 (P4C10, 10 ug/ml) or α4 (P4C2, 10 ug/ml) on the LDVPST-rsa coated surfaces for 30 min at 37° C. Thus, the Control, as well as P4C10 or P4C2 treated cells were activated with 8A2.

P4C10 anti-β1 and 8A2 anti-β1 antibodies recognize functionally distinct epitopes on β1 (Kovach, N. L., and J. M. Harlan, personal communication): i.e., 8A2 stimulates β1-mediated adherence to VCAM-1 and P4C10 inhibits β1-mediated binding to VCAM or fibronectin. Kinetic analysis of 8A2 activation of α4β1 receptor complexes revealed that 8A2 induces rapid and stable U937 (or Jurkat) cell adhesion to LDV peptide-coated surfaces. Within 5 min. significant adhesion can be measured which peaks at 10–20 min. In some cell populations, such as Jurkat cells LDV recognition peaks within 5 min. exposure to 8A2. U937 cells were not observed to adhere to LDV-coated surfaces; even after 90 min. of incubation. The data herein clearly indicates that the effects of 8A2 are not simply on the rate of adhesion, but also are effective to alter the function of LDV recognition by the α4β1 receptor complex, presumably via an alteration in conformation of the receptor, and possibly resulting in increased α4β1 receptor complex avidity and LDV recognition.

Kinetic analysis of U937 cell adhesion to LDV-peptide coated surfaces was tested in the presence of Mab 8A2 and the results are presented in FIG. 17. These experiments were conducted as follows: $^{51}$Cr-labeled U937 cells (2×10$^5$) were applied to triplicate wells of separate 48 well plates (one for each time point) which had been coated with 5 ug/ml LDVPST-rsa. At Time 0, 5 ug/ml purified 8A2 was added to the wells designated as activated (triplicate control wells to which 5 ug/ml non-immune mouse IgG was added were included for each time point). Separate individual plates were harvested at each time point as described above. The results are expressed as counts per minute extracted from adherent cells. In this experiment total cell input was 28,796±1389.

The results presented in FIG. 17 show that nearly maximal LDV-dependent adhesion was achieved after 5–10 min activation with 8A2.

8.2.2.5. Resting T Lymphocytes Require Two Signals for Adhesion to LDV.

Interestingly, resting PBL did not adhere to CS-1 or LDV-coated surfaces even after pre-incubation with 8A2. Peripheral blood derived T lymphocytes required prior activation with PHA (72 hr. culture) in order to interact with LDV coated surfaces in the presence of 8A2 (FIG. 18).

Adhesion of 72 hr PHA stimulated T cell blasts to pFN, CS-1, A13 or B12 and derivative peptide-coated surfaces was tested and the results are shown in FIGS. 18A and 18B. In FIG. 18A adhesion was tested in the presence of purified non-immune mouse IgG (5 ug/ml); and, in FIG. 18B adhesion was tested in the presence of Mab 8A2 (5 ug/ml). These experiments were conducted as follows: 48 well plates were coated with 5 ug/ml (based on peptide weight) peptide-rsa conjugates overnight in PBS at 4° C. $^{51}$Cr-labeled PHA blasts were allowed to adhere to the peptide-coated surfaces in the presence of IgG or 8A2 for 30 min at 37° C. The rest of the adhesion assay proceeded as for FIG. 12. Results are expressed as counts per minute extracted from adherent cells. Human PHA stimulated T cell blasts were derived as previously described (Wayner et al., 1989, supra).

PHA activation can increase α4β1 expression on T lymphocytes (supra.). However, treatment with 8A2 does not increase surface expression of either α4 or β1 on resting PBL or PHA activated T cell blasts. Therefore, the effects of 8A2 on LDV (SEQ ID NO: 3) recognition by PHA-activated T lymphocytes cannot be the result of increased α4β1 expression. This strongly suggests that resting PBL, unlike cultured hematopoietic cell lines, require at least two signals for CS-1 (LDV) recognition, one of which is transduced through β1 (8A2) while the other is transduced through the T cell receptor (PHA).

8.2.3. Discussion

Recently, it has been reported by several laboratories that lymphocyte integrin receptors (reviewed by Springer, 1990, Nature 346: 425–434) can be activated to bind ligand with high avidity (Neugebauer and Reichardt, 1991, supra; Kovach, N. L., and J. M. Harlan, personal communication). Activation of integrins in T lymphocytes can reportedly be achieved by cross-linking the T cell receptor (Dustin and Springer, 1989, Nature 341: 619–624; Shimizu et al., 1990, supra) or by incubating cells with monoclonal antibodies to β1 (Kovach, supra.). Therefore, hematopoietic cell adhesion to CS-1 (SEQ ID NO: 15) and derivative peptides was examined, herein, in the presence or absence of an antibody known to activate β1. Resting hematopoietic cells that expressed the α4β1 receptor complex bound the LDV peptide relatively poorly. Such cell populations were, however, able to bind LDV in the context of CS-1 or in some cases CS-1-B12. After activating β1 with a monoclonal antibody that up-regulates β1 function (i.e., 8A2; Kovach, supra) the minimal peptide ligand for the α4β1 receptor complex in hematopoietic cells was determined (herein) to be LDV. Furthermore, when the β1 complex was in the high avidity state, the molar concentration of LDV peptide required to support stable cell adhesion was similar to intact CS-1. Crosslinking of β1 by 8A2 is not required to up-regulate β1 dependent function, because Fab fragments are as effective as intact antibody (Kovach, supra). Furthermore, 8A2 activation is energy dependent and does not result in the upregulation of surface expression of α4 or β1. Together these data strongly suggest that the adhesion of some cell populations to the LDV sequence in CS-1 is regulated in a cell-type specific manner and requires an activation signal transduced through β1.

In conclusion, the studies herein identify the LDV tripeptide as the minimal adhesive peptide in the CS-1 portion of the V region of fibronectin. However, cells that express the high avidity form of the receptor appear to bind more readily to LDV-coated surfaces. The high avidity state of the receptor can be induced by preincubating cells with an activating monoclonal antibody to β1 (e.g., 8A2 or P4B4; Coulter Immunologics). 8A2 activation of β1 was rapid and did not result in an increase in cell surface β1 expression. Resting peripheral blood T cells were not induced (under the present conditions) with 8A2 to bind LDV, while PHA stimulated T cells blasts could be. This implies that LDV recognition by normal T cell may require at least two signals, e.g., one transduced through the T cell receptor (PHA activation) and the other via the integrin β1 subunit (8A2). Since resting T cells, PHA blasts, HUT 78, and Jurkat cells do not demonstrate the same pattern or level of CS-1 (SEQ ID NO: 15) peptide recognition, the findings herein suggest that malignant or activated T cells may express receptor complexes that can also vary in terms of basal α4β1 activation. These findings are of significance to malignant T lymphocyte transformation and infiltration of organs such as the bone marrow, skin or brain in neoplastic or chronic inflammatory disease.

9. DEPOSIT OF CELL LINES

The following cell lines have been deposited with the American Type Culture Collection (ATCC), 12301 Parklawn Drive, Rockville, Md. 20852, on Sep. 1, 1989, and have been assigned the following accession numbers:

| Cell Line | Accession Number |
|---|---|
| P4C2 | HB10215 |
| P4G9 | HB10213 |
| P3E3 | HB10212 |
| P4C10 | HB10214 |

The present invention is not to be limited in scope by the genes and proteins exemplified or deposited microorganisms which are intended as but single illustrations of one aspect of the invention. Indeed, various modifications of the invention in addition to those shown and described herein will become apparent to those skilled in the art from the foregoing description and accompanying figures. Such modifications are intended to fall within the scope of the appended claims.

What is claimed is:

1. A method for inhibiting the adherence of lymphocytes to cytokine activated endothelial cells comprising exposing the lymphocytes to an effective amount of a peptide that binds to $\alpha_4\beta_1$, the peptide consisting of from three to about twelve contiguous amino acid residues of the CS-1 region of fibronectin, and wherein said peptide comprises the amino acid sequence Leu Asp Val (SEQ ID NO: 3).

2. The method of claim 1 in which the peptide is conjugated to an antibody targeted toward endothelial cells.

3. The method according to claim 1 in which the peptide comprises at least the sequence Glu Ile Leu Asp Val Pro Ser Thr (SEQ ID NO:6).

4. The method according to claim 1 in which the peptide comprises at least the sequence Glu Ile Leu Asp Val (SEQ ID NO:14).

5. The method according to claim 1 in which the peptide comprises at least the sequence Leu Asp Val Pro Ser Thr (SEQ ID NO:11).

6. The method according to claim 1 in which the peptide comprises at least the sequence Leu Asp Val (SEQ ID NO:3).

7. A pharmaceutical composition comprising an effective concentration of a peptide which binds to $\alpha_4\beta_1$ and which inhibits the adherence of lymphocytes to cytokine activated endothelial cells, in a pharmacologically suitable carrier, the peptide consisting of from three to about twelve contiguous amino acid residues of the CS-1 region of fibronectin, and wherein said peptide comprises the amino acid sequence Leu Asp Val (SEQ ID NO: 3).

8. The pharmaceutical composition of claim 7 in which the peptide comprises the sequence Glu Ile Leu Asp Val Pro Ser Thr (SEQ ID NO:6).

9. The pharmaceutical composition of claim 7 in which the peptide comprises the sequence Glu Ile Leu Asp Val (SEQ ID NO:14).

10. The pharmaceutical composition of claim 7 in which the peptide comprises the sequence Leu Asp Val Pro Ser Thr (SEQ ID NO:11).

11. The pharmaceutical composition of claim 7 in which the peptide comprises the sequence Leu Asp Val (SEQ ID NO:3).

12. A method of preventing lymphocyte migration into tissues comprising administering an effective amount of a peptide binding to $\alpha_4\beta_1$ in a pharmacologically suitable carrier, which prevents lymphocyte adhesion to cytokine activated endothelial cells, to a subject in need of such treatment, the peptide consisting of from three to about twelve contiguous amino acid residues of the CS-1 region of fibronectin, and wherein said peptide comprises the amino acid sequence Leu Asp Val (SEQ ID NO: 3).

13. The method according to claim 12 in which the peptide comprises the sequence Glu Ile Leu Asp Val Pro Ser Thr (SEQ ID NO:6).

14. The method according to claim 12 in which the peptide comprises the sequence Glu Ile Leu Asp Val (SEQ ID NO:14).

15. The method according to claim 12 in which the peptide comprises the sequence Leu Asp Val Pro Ser Thr (SEQ ID NO:11).

16. The method according to claim 12 in which the peptide sequence comprises the sequence Leu Asp Val (SEQ ID NO:3).

\* \* \* \* \*

SEQUENCE LISTING

<160> NUMBER OF SEQ ID NOS: 19

<210> SEQ ID NO 1
<211> LENGTH: 4
<212> TYPE: PRT
<213> ORGANISM: Homo sapiens

-continued

```
<400> SEQUENCE: 1

Arg Gly Asp Ser
1

<210> SEQ ID NO 2
<211> LENGTH: 4
<212> TYPE: PRT
<213> ORGANISM: Homo sapiens

<400> SEQUENCE: 2

Arg Gly Asp Val
1

<210> SEQ ID NO 3
<211> LENGTH: 3
<212> TYPE: PRT
<213> ORGANISM: Homo sapiens

<400> SEQUENCE: 3

Leu Asp Val
1

<210> SEQ ID NO 4
<211> LENGTH: 10
<212> TYPE: PRT
<213> ORGANISM: Homo sapiens

<400> SEQUENCE: 4

Ser Asp Val Pro Ser Pro Arg Leu Gln Phe
1               5                   10

<210> SEQ ID NO 5
<211> LENGTH: 15
<212> TYPE: PRT
<213> ORGANISM: Homo sapiens

<400> SEQUENCE: 5

Thr Ala Gly Pro Asp Gln Thr Glu Met Thr Ile Glu Gly Leu Gln
1               5                   10                  15

<210> SEQ ID NO 6
<211> LENGTH: 8
<212> TYPE: PRT
<213> ORGANISM: Homo sapiens

<400> SEQUENCE: 6

Glu Ile Leu Asp Val Pro Ser Thr
1               5

<210> SEQ ID NO 7
<211> LENGTH: 3
<212> TYPE: PRT
<213> ORGANISM: Artificial Sequence
<220> FEATURE:
<223> OTHER INFORMATION: Description of Artificial Sequence: Peptide
      substantially homologous to SEQ ID NO 6

<400> SEQUENCE: 7

Arg Gly Asp
1

<210> SEQ ID NO 8
<211> LENGTH: 8
<212> TYPE: PRT
<213> ORGANISM: Artificial Sequence
```

```
<220> FEATURE:
<223> OTHER INFORMATION: Description of Artificial Sequence: Peptide
      substantially homologous to SEQ ID NO 6.
<221> NAME/KEY: VARIANT
<222> LOCATION: (1)
<223> OTHER INFORMATION: Glu or Asp
<221> NAME/KEY: VARIANT
<222> LOCATION: (2)
<223> OTHER INFORMATION: Ile, Ala, Leu, Val, Pro, Phe, Trp or Met
<221> NAME/KEY: VARIANT
<222> LOCATION: (3)
<223> OTHER INFORMATION: Ile, Ala, Leu, Val, Pro, Phe, Trp, or Met
<221> NAME/KEY: VARIANT
<222> LOCATION: (4)
<223> OTHER INFORMATION: Glu or Asp
<221> NAME/KEY: VARIANT
<222> LOCATION: (5)
<223> OTHER INFORMATION: Ile, Ala, Leu, Val, Pro, Phe, Trp or Met
<221> NAME/KEY: VARIANT
<222> LOCATION: (6)
<223> OTHER INFORMATION: Ile, Ala, Leu, Val, Pro, Phe, Trp or Met
<221> NAME/KEY: VARIANT
<222> LOCATION: (7)
<223> OTHER INFORMATION: Ser, Glu, Thr, Cys, Tyr, Asn or Glu
<221> NAME/KEY: VARIANT
<222> LOCATION: (8)
<223> OTHER INFORMATION: Ser, Glu, Thr, Cys, Tyr, Asn or Gln

<400> SEQUENCE: 8

Xaa Xaa Xaa Xaa Xaa Xaa Xaa Xaa
 1               5

<210> SEQ ID NO 9
<211> LENGTH: 10
<212> TYPE: PRT
<213> ORGANISM: Homo sapiens

<400> SEQUENCE: 9

Gly Pro Glu Ile Leu Asp Val Pro Ser Thr
 1               5                  10

<210> SEQ ID NO 10
<211> LENGTH: 4
<212> TYPE: PRT
<213> ORGANISM: Homo sapiens

<400> SEQUENCE: 10

Val Pro Ser Thr
 1

<210> SEQ ID NO 11
<211> LENGTH: 6
<212> TYPE: PRT
<213> ORGANISM: Homo sapiens

<400> SEQUENCE: 11

Leu Asp Val Pro Ser Thr
 1               5

<210> SEQ ID NO 12
<211> LENGTH: 13
<212> TYPE: PRT
<213> ORGANISM: Homo sapiens

<400> SEQUENCE: 12

Asp Glu Leu Pro Gln Leu Val Thr Leu Pro His Pro Asn
 1               5                  10

<210> SEQ ID NO 13
```

```
<211> LENGTH: 12
<212> TYPE: PRT
<213> ORGANISM: Homo sapiens

<400> SEQUENCE: 13

Leu His Gly Pro Glu Ile Leu Asp Val Pro Ser Thr
 1               5                  10

<210> SEQ ID NO 14
<211> LENGTH: 5
<212> TYPE: PRT
<213> ORGANISM: Homo sapiens

<400> SEQUENCE: 14

Glu Ile Leu Asp Val
 1               5

<210> SEQ ID NO 15
<211> LENGTH: 25
<212> TYPE: PRT
<213> ORGANISM: Homo sapiens

<400> SEQUENCE: 15

Asp Glu Leu Pro Gln Leu Val Thr Leu Pro His Pro Asn Leu His Gly
 1               5                  10                  15

Pro Glu Ile Leu Asp Val Pro Ser Thr
            20                  25

<210> SEQ ID NO 16
<211> LENGTH: 4
<212> TYPE: PRT
<213> ORGANISM: Homo sapiens

<400> SEQUENCE: 16

Leu His Gly Pro
 1

<210> SEQ ID NO 17
<211> LENGTH: 3
<212> TYPE: PRT
<213> ORGANISM: Homo sapiens

<400> SEQUENCE: 17

Pro Ser Thr
 1

<210> SEQ ID NO 18
<211> LENGTH: 46
<212> TYPE: PRT
<213> ORGANISM: Homo sapiens

<400> SEQUENCE: 18

Asp Glu Leu Pro Gln Leu Val Thr Leu Pro His Pro Asn Leu His Gly
 1               5                  10                  15

Pro Glu Ile Leu Asp Val Pro Ser Thr Val Gln Lys Thr Pro Phe Val
            20                  25                  30

Thr His Pro Gly Tyr Asp Thr Gly Gln Gly Ile Gln Leu Pro
            35                  40                  45

<210> SEQ ID NO 19
<211> LENGTH: 4
<212> TYPE: PRT
<213> ORGANISM: Homo sapiens
```

-continued

```
<400> SEQUENCE: 19

Arg Glu Asp Val
 1
```